(12) United States Patent
Fischer et al.

(10) Patent No.: US 9,416,416 B2
(45) Date of Patent: *Aug. 16, 2016

(54) BIOLOGICAL SPECIMEN COLLECTION/TRANSPORT COMPOSITIONS AND METHODS

(75) Inventors: Gerald W. Fischer, Bethesda, MD (US); Luke T. Daum, San Antonio, TX (US)

(73) Assignee: Longhorn Vaccines and Diagnostics, LLC, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/328,992

(22) Filed: Dec. 16, 2011

(65) Prior Publication Data

US 2012/0088231 A1    Apr. 12, 2012

Related U.S. Application Data

(63) Continuation of application No. 12/426,890, filed on Apr. 20, 2009, now Pat. No. 8,080,645, which is a continuation-in-part of application No. 12/243,949, and a continuation-in-part of application No. PCT/US2008/078499, filed on Oct. 1, 2008, now Pat. No. 8,084,443.

(60) Provisional application No. 60/976,728, filed on Oct. 1, 2007.

(51) Int. Cl.
   *C12Q 1/68* (2006.01)
   *C12Q 1/70* (2006.01)
   *C12N 15/10* (2006.01)

(52) U.S. Cl.
   CPC .......... *C12Q 1/6876* (2013.01); *C12N 15/1003* (2013.01); *C12Q 1/6806* (2013.01); *C12Q 1/6848* (2013.01); *C12Q 1/6851* (2013.01); *C12Q 2600/166* (2013.01)

(58) Field of Classification Search
   None
   See application file for complete search history.

(56) References Cited

U.S. PATENT DOCUMENTS

| | | |
|---|---|---|
| 4,116,777 A | 9/1978 | Takátsy et al. |
| 4,196,265 A | 4/1980 | Koprowski et al. |
| 4,235,244 A | 11/1980 | Abele et al. |
| 4,315,073 A | 2/1982 | Brown et al. |
| 4,355,102 A | 10/1982 | Quash |
| 4,356,170 A | 10/1982 | Jennings et al. |
| 4,372,945 A | 2/1983 | Likhite |
| 4,474,757 A | 10/1984 | Arnon et al. |
| 4,529,702 A | 7/1985 | Bryan |
| 4,554,101 A | 11/1985 | Hopp |
| 4,559,231 A | 12/1985 | Bjerre et al. |
| 4,578,770 A | 3/1986 | Mitani |
| 4,588,680 A | 5/1986 | Bucher et al. |
| 4,596,792 A | 6/1986 | Vyas |
| 4,599,230 A | 7/1986 | Milich et al. |
| 4,601,903 A | 7/1986 | Frasch |
| 4,608,251 A | 8/1986 | Mia |
| 4,634,664 A | 1/1987 | Oestberg |
| 4,634,666 A | 1/1987 | Engleman et al. |
| 4,668,476 A | 5/1987 | Bridgham et al. |
| 4,683,195 A | 7/1987 | Mullis et al. |
| 4,683,202 A | 7/1987 | Mullis |
| 4,707,450 A | 11/1987 | Nason |
| 4,744,982 A | 5/1988 | Hunter et al. |
| 4,746,490 A | 5/1988 | Saneii |
| 4,749,490 A | 6/1988 | Smyth et al. |
| 4,800,159 A | 1/1989 | Mullis et al. |
| 4,803,998 A | 2/1989 | Kezes et al. |
| 4,816,513 A | 3/1989 | Bridgham et al. |
| 4,883,750 A | 11/1989 | Whiteley et al. |
| 4,954,449 A | 9/1990 | Hunter et al. |
| 4,981,782 A | 1/1991 | Judd et al. |
| 4,996,143 A | 2/1991 | Heller et al. |
| 5,091,316 A | 2/1992 | Monthony et al. |
| 5,108,927 A | 4/1992 | Dorn |
| 5,136,019 A | 8/1992 | Judd et al. |

(Continued)

FOREIGN PATENT DOCUMENTS

| | | |
|---|---|---|
| CN | 1310235 | 8/2001 |
| EP | 0 313 224 A1 | 4/1989 |
| EP | 320308 | 6/1989 |
| EP | 0 621 339 A2 | 10/1994 |
| EP | 0 675 199 A2 | 10/1995 |
| EP | 0 726 316 A2 | 8/1996 |
| EP | 1 081 496 A1 | 3/2001 |
| RU | 2150281 C1 | 10/2000 |
| WO | WO 91/02740 | 3/1991 |
| WO | WO 92/03454 | 3/1992 |

(Continued)

OTHER PUBLICATIONS

Canadian Office Action for application No. 2697373, dated Feb. 19, 2013.
CA Office action for PCT/US08/78499, dated Mar. 29, 2012.
CA Office action for PCT/US2007/078025, dated Jan. 4, 2011.
EPO Exam Report for PCT/US2007/078025, dated Dec. 30, 2011.
EPO Exam Report for PCT/US2007/078025, dated Aug. 26, 2010.

(Continued)

*Primary Examiner* — David Thomas
(74) *Attorney, Agent, or Firm* — Remenick PLLC

(57) ABSTRACT

Disclosed are compositions for collecting, storing, and transporting populations of nucleic acids from biological specimens, and clinical, forensic, or environmental samples. Also disclosed are methods for using these compositions as one-step formulations for killing pathogens, inactivating nucleases, and releasing polynucleotides from other cellular components within the sample, and stabilizing the nucleic acids prior to further processing or assay. In particular embodiments, the invention provides a single, one-step, sample collection/transport/storage formulation containing a known quantity of a non-genomic, nucleic acid carrier molecule that serves as an internal reference control to monitor the fidelity of the collection/transportation medium, and measure the integrity of nucleic acids subsequently isolated and purified from the processed sample.

40 Claims, 26 Drawing Sheets

(56) References Cited

U.S. PATENT DOCUMENTS

| | | |
|---|---|---|
| 5,145,684 A | 9/1992 | Liversidge et al. |
| 5,149,653 A | 9/1992 | Roser |
| 5,163,441 A | 11/1992 | Monthony et al. |
| 5,168,039 A | 12/1992 | Crawford et al. |
| 5,182,109 A | 1/1993 | Tamura et al. |
| 5,186,898 A | 2/1993 | Bridgham et al. |
| 5,187,060 A | 2/1993 | Cerutti et al. |
| 5,234,809 A | 8/1993 | Boom |
| 5,243,030 A | 9/1993 | Judd et al. |
| 5,252,458 A | 10/1993 | Liav et al. |
| 5,290,686 A | 3/1994 | Kendal et al. |
| 5,316,910 A | 5/1994 | Rota et al. |
| 5,399,363 A | 3/1995 | Liversidge et al. |
| 5,482,856 A | 1/1996 | Fell, Jr. et al. |
| 5,503,841 A | 4/1996 | Doyle et al. |
| 5,543,158 A | 8/1996 | Gref et al. |
| 5,545,555 A | 8/1996 | Racioppi et al. |
| 5,552,157 A | 9/1996 | Yagi et al. |
| 5,565,213 A | 10/1996 | Nakamori et al. |
| 5,565,322 A | 10/1996 | Heller |
| 5,567,434 A | 10/1996 | Szoka, Jr. |
| 5,571,511 A | 11/1996 | Fischer |
| 5,589,174 A | 12/1996 | Okuno et al. |
| 5,627,071 A | 5/1997 | Triva |
| 5,631,350 A | 5/1997 | Okuno et al. |
| 5,641,515 A | 6/1997 | Ramtoola |
| 5,656,016 A | 8/1997 | Ogden |
| 5,663,055 A | 9/1997 | Turner et al. |
| 5,679,356 A | 10/1997 | Bonnem et al. |
| 5,691,299 A | 11/1997 | Fabry |
| 5,697,899 A | 12/1997 | Hillman et al. |
| 5,702,944 A | 12/1997 | Racioppi et al. |
| 5,719,020 A | 2/1998 | Liav et al. |
| 5,736,333 A | 4/1998 | Livak et al. |
| 5,738,868 A | 4/1998 | Shinkarenko |
| 5,741,516 A | 4/1998 | Webb et al. |
| 5,766,841 A | 6/1998 | Liav et al. |
| 5,770,219 A | 6/1998 | Chiang et al. |
| 5,779,708 A | 7/1998 | Wu |
| 5,783,208 A | 7/1998 | Venkateshwaran et al. |
| 5,785,975 A | 7/1998 | Parikh |
| 5,795,582 A | 8/1998 | Wright |
| 5,795,587 A | 8/1998 | Gao et al. |
| 5,797,898 A | 8/1998 | Santini, Jr. et al. |
| 5,800,810 A | 9/1998 | Doyle et al. |
| 5,849,489 A | 12/1998 | Heller |
| 5,891,624 A | 4/1999 | Huang |
| 5,945,515 A | 8/1999 | Chomczynski ............... 530/412 |
| 5,955,074 A | 9/1999 | Fischer |
| 5,958,379 A | 9/1999 | Regenold et al. |
| 6,015,664 A | 1/2000 | Henrickson et al. |
| 6,033,673 A | 3/2000 | Clements |
| 6,060,068 A | 5/2000 | Doyle et al. |
| 6,136,585 A | 10/2000 | Ball et al. |
| 6,162,603 A | 12/2000 | Heller |
| 6,168,915 B1 | 1/2001 | Scholl et al. |
| 6,242,582 B1 | 6/2001 | Reece et al. |
| 6,280,928 B1 | 8/2001 | Scholl et al. |
| 6,306,404 B1 | 10/2001 | LaPosta et al. |
| 6,306,582 B1 | 10/2001 | Scholl et al. |
| 6,312,395 B1 | 11/2001 | Tripp et al. |
| 6,376,172 B1 | 4/2002 | Scholl et al. |
| 6,406,842 B2 | 6/2002 | Scholl et al. |
| 6,440,423 B1 | 8/2002 | Clements et al. |
| 6,451,325 B1 | 9/2002 | Van Nest et al. |
| 6,458,577 B1 | 10/2002 | Huang |
| 6,495,316 B1 | 12/2002 | Scholl et al. |
| 6,500,432 B1 | 12/2002 | Dalemans et al. |
| 6,503,745 B1 | 1/2003 | Chand et al. |
| 6,534,065 B1 | 3/2003 | Makin et al. |
| 6,572,866 B1 | 6/2003 | Torcia |
| 6,573,080 B2 | 6/2003 | Scholl et al. |
| 6,602,510 B1 | 8/2003 | Fikes et al. |
| 6,603,908 B2 | 8/2003 | Dallas et al. |
| 6,603,998 B1 | 8/2003 | King et al. |
| 6,610,293 B1 | 8/2003 | Fischer et al. |
| 6,610,474 B1 | 8/2003 | Huang |
| 6,627,396 B1 | 9/2003 | Swanson et al. |
| 6,632,432 B1 | 10/2003 | Fischer |
| 6,680,308 B1 | 1/2004 | Hassan |
| 6,689,363 B1 | 2/2004 | Sette et al. |
| 6,713,068 B1 | 3/2004 | Audonnet et al. |
| 6,720,409 B2 | 4/2004 | Okuno et al. |
| 6,734,292 B1 | 5/2004 | Omura et al. |
| 6,759,241 B1 | 7/2004 | Hone et al. |
| 6,780,421 B1 | 8/2004 | Haensler et al. |
| 6,793,928 B1 | 9/2004 | van Scharrenburg et al. |
| 6,811,971 B2 | 11/2004 | Klepp et al. |
| 6,855,321 B1 | 2/2005 | Rappuoli et al. |
| 6,875,600 B2 | 4/2005 | Scholl et al. |
| 6,881,835 B2 | 4/2005 | Bai et al. |
| 6,893,814 B2 | 5/2005 | Swanson et al. |
| 6,939,543 B2 | 9/2005 | Fischer et al. |
| 6,946,245 B2 * | 9/2005 | Baumann et al. .................. 435/5 |
| 6,946,291 B2 | 9/2005 | Scholl et al. |
| 7,090,853 B2 | 8/2006 | Kapp et al. |
| 7,122,640 B2 | 10/2006 | Gjerde et al. |
| 7,223,409 B2 | 5/2007 | Nagata et al. |
| 7,279,162 B1 | 10/2007 | Fischer |
| 7,311,671 B2 | 12/2007 | Jung et al. |
| 7,351,413 B2 | 4/2008 | Page et al. |
| 7,357,936 B1 | 4/2008 | Garcon |
| 7,361,352 B2 | 4/2008 | Birkett et al. |
| 7,371,531 B2 * | 5/2008 | Hellyer et al. ............... 435/6.11 |
| 7,438,919 B2 | 10/2008 | Dowling |
| 7,494,771 B2 | 2/2009 | Picard et al. |
| 7,541,194 B2 | 6/2009 | Mink et al. |
| 7,547,512 B2 | 6/2009 | Peiris |
| 7,648,681 B2 | 1/2010 | Meyer et al. |
| 7,718,402 B2 | 5/2010 | Gayral et al. |
| 7,767,804 B2 | 8/2010 | Bair, Jr. et al. |
| 7,794,001 B2 | 9/2010 | Blackwell et al. |
| 8,080,645 B2 | 12/2011 | Fischer et al. |
| 8,084,443 B2 | 12/2011 | Fischer et al. |
| 8,097,419 B2 | 1/2012 | Fischer et al. |
| 8,293,467 B2 | 10/2012 | Fischer et al. |
| 2001/0021501 A1 | 9/2001 | Scholl et al. |
| 2001/0023065 A1 | 9/2001 | Lee |
| 2001/0034022 A1 | 10/2001 | Scholl et al. |
| 2001/0036628 A1 | 11/2001 | Scholl et al. |
| 2002/0054882 A1 | 5/2002 | Okuno et al. |
| 2002/0055094 A1 | 5/2002 | Reece et al. |
| 2002/0081567 A1 | 6/2002 | Henrickson et al. |
| 2002/0082395 A1 | 6/2002 | Fischer et al. |
| 2002/0169140 A1 | 11/2002 | Prendergast |
| 2003/0119209 A1 | 6/2003 | Kaylor et al. |
| 2003/0143566 A1 | 7/2003 | Helftenbein |
| 2003/0203357 A1 | 10/2003 | Huang |
| 2003/0215796 A1 | 11/2003 | Scholl et al. |
| 2003/0219442 A1 | 11/2003 | Mikayama et al. |
| 2004/0009126 A1 | 1/2004 | Pilkiewicz et al. |
| 2004/0013673 A1 | 1/2004 | Fischer et al. |
| 2004/0071757 A1 | 4/2004 | Rolf |
| 2004/0082549 A1 | 4/2004 | Jomaa |
| 2004/0086849 A1 | 5/2004 | Shimasaki et al. |
| 2004/0101869 A1 | 5/2004 | Berg et al. |
| 2004/0126789 A1 | 7/2004 | Park et al. |
| 2004/0142319 A1 | 7/2004 | Yu et al. |
| 2004/0170965 A1 | 9/2004 | Scholl et al. |
| 2004/0214272 A1 | 10/2004 | La Rosa et al. |
| 2004/0223976 A1 | 11/2004 | Bianchi et al. |
| 2005/0009008 A1 | 1/2005 | Robinson et al. |
| 2005/0042229 A1 | 2/2005 | Yang et al. |
| 2005/0090009 A1 | 4/2005 | Cormier et al. |
| 2005/0112656 A1 | 5/2005 | Iwaki |
| 2005/0169941 A1 | 8/2005 | Lees |
| 2005/0170334 A1 | 8/2005 | Mikayama et al. |
| 2005/0181357 A1 | 8/2005 | Peiris et al. |
| 2005/0187213 A1 | 8/2005 | Lang et al. |
| 2005/0227269 A1 | 10/2005 | Lloyd, Jr. et al. |
| 2006/0002939 A1 | 1/2006 | Fischer et al. |
| 2006/0014177 A1 * | 1/2006 | Hogan et al. ...................... 435/6 |
| 2006/0014185 A1 | 1/2006 | Ollikka et al. |
| 2006/0105468 A1 | 5/2006 | Winkler et al. |

(56) References Cited

U.S. PATENT DOCUMENTS

| | | | |
|---|---|---|---|
| 2006/0121468 | A1 | 6/2006 | Allnutt et al. |
| 2006/0134648 | A1 | 6/2006 | Chou et al. |
| 2006/0286557 | A1 | 12/2006 | Basehore et al. |
| 2007/0102946 | A1 | 5/2007 | Blackwell et al. |
| 2007/0172835 | A1 | 7/2007 | McBride et al. |
| 2007/0196388 | A1 | 8/2007 | Dowling et al. |
| 2007/0202497 | A1 | 8/2007 | Renuart et al. ............... 435/6 |
| 2007/0202511 | A1 | 8/2007 | Chen et al. |
| 2007/0286871 | A1 | 12/2007 | Hickle et al. |
| 2008/0032921 | A1 | 2/2008 | Alexander et al. |
| 2008/0050737 | A1 | 2/2008 | Arieli et al. |
| 2008/0069821 | A1 | 3/2008 | Yang et al. |
| 2008/0075708 | A1 | 3/2008 | Yu et al. |
| 2008/0107665 | A1 | 5/2008 | Suckow et al. |
| 2008/0107687 | A1 | 5/2008 | Poulet |
| 2008/0118531 | A1 | 5/2008 | Hoffmann et al. |
| 2008/0139789 | A1 | 6/2008 | Fischer |
| 2008/0145373 | A1 | 6/2008 | Arumugham et al. |
| 2008/0181914 | A1 | 7/2008 | Eichhorn |
| 2008/0260763 | A1 | 10/2008 | Felgner et al. |
| 2009/0081202 | A1 | 3/2009 | Fischer et al. |
| 2009/0098527 | A1 | 4/2009 | Fischer et al. |
| 2009/0233309 | A1 | 9/2009 | Fischer et al. |
| 2009/0312285 | A1 | 12/2009 | Fischer et al. |
| 2010/0009343 | A1 | 1/2010 | Fischer |
| 2010/0055672 | A1 | 3/2010 | Saghbini |
| 2010/0151477 | A1 | 6/2010 | Cawthon |
| 2010/0221822 | A1 | 9/2010 | Fischer et al. |
| 2010/0311739 | A1 | 12/2010 | Gunaratnan et al. |
| 2011/0159497 | A1 | 6/2011 | Lee et al. |
| 2011/0281754 | A1 | 11/2011 | Fischer et al. |
| 2012/0088231 | A1 | 4/2012 | Fischer et al. |
| 2012/0100529 | A1 | 4/2012 | Fischer et al. |
| 2012/0107799 | A1 | 5/2012 | Daum |
| 2012/0115126 | A1 | 5/2012 | Fischer et al. |
| 2012/0244527 | A1 | 9/2012 | Trinh et al. |

FOREIGN PATENT DOCUMENTS

| | | |
|---|---|---|
| WO | WO 92/16619 | 10/1992 |
| WO | WO 94/09035 | 4/1994 |
| WO | WO 94/17106 | 8/1994 |
| WO | WO95/08348 | 3/1995 |
| WO | WO 95/08348 | 3/1995 |
| WO | WO 97/05248 A2 | 2/1997 |
| WO | WO97/46707 | 12/1997 |
| WO | WO97/46712 | 12/1997 |
| WO | WO97/46714 | 12/1997 |
| WO | WO 98/40099 | 9/1998 |
| WO | WO01/16163 | 3/2001 |
| WO | WO01/16163 | 8/2001 |
| WO | WO 03/053462 | 3/2003 |
| WO | WO 03/026567 A2 | 4/2003 |
| WO | WO03/053462 | 7/2003 |
| WO | WO03/095646 | 11/2003 |
| WO | WO2004/002451 | 1/2004 |
| WO | WO 2004/004658 A2 | 1/2004 |
| WO | WO2004/043407 | 5/2004 |
| WO | WO 2004/043407 | 5/2004 |
| WO | WO 2004/055205 | 7/2004 |
| WO | WO2004/002451 | 8/2004 |
| WO | WO 2004/072270 A1 | 8/2004 |
| WO | WO 2004/084876 A2 | 10/2004 |
| WO | WO 2005010186 | 2/2005 |
| WO | WO 2005/042784 | 5/2005 |
| WO | WO 2005/075642 A1 | 8/2005 |
| WO | WO 2005/085274 A1 | 8/2005 |
| WO | WO2006/041933 | 4/2006 |
| WO | WO 2006/138444 | 12/2006 |
| WO | WO2006/138444 | 12/2006 |
| WO | WO 2007/051036 | 3/2007 |
| WO | WO2007/051036 | 5/2007 |
| WO | WO 2007/056266 | 5/2007 |
| WO | WO2007/056266 | 5/2007 |
| WO | WO2007051036 | 5/2007 |
| WO | WO2007056266 | 5/2007 |
| WO | WO 2007/091030 | 8/2007 |
| WO | WO2007/091030 | 8/2007 |
| WO | WO 2007/133682 | 11/2007 |
| WO | WO2008079463 | 3/2008 |
| WO | WO2008079463 | 7/2008 |
| WO | WO2009085355 | 7/2009 |
| WO | WO2009085355 | 9/2009 |

OTHER PUBLICATIONS

EPO Exam Report for PCT/US2007/078025, dated Jul. 6, 2009.
EPO Exam Report for PCT/US2007/078025, dated May 18, 2009.
AU Exam Report for PCT/US2007/078025, dated Nov. 19, 2010.
IL Exam Report for PCT/US2007/078025, dated Mar. 16, 2011.
NZ Exam Report for PCT/US2007/078025, dated Jul. 7, 2010.
Israel Office Action of Jul. 19, 2012.
EPO Supplementary Search Report for PCT/US10/31761, dated Jul. 13, 2012.
CA Office Action for PCT/US2008/078499, dated Mar. 29, 2012.
PCT Written Opinion for PCT/US2008/078499, dated Jul. 4, 2010.
"Monolithic Silica Extraction Tips for Sample Preparation," CP-Analytica, available at http://cp-analytica (last visited Oct. 25, 2010).
Barnard, et al., "Suitability of new chlamydia transport medium for transport of herpes simplex virus," J. of Clin. Microbiol., 24(5): 692-695 (1986).
Eroglu, et al., "Successful cyropreservation of mouse oocytes by using low concentrations of trehalose and dimethylsylfoxide," Biol. of Rep. 80:70-78 (2009).
Gelmi, et al., "Bacertial survival in different transport media," European Congress of Clinical Microbiology and Infectious Diseases (ECCMID), May 28-31, 2000 (poster).
Higashiyama, T., "Novel functions and applications of terhalose," Pure Appl. Chem. 74(7): 1263-1269.
H1N1 RTPCR Primer/Probe Sets, Intergrated DNA Technologies—H1N1, available at http://www.idtdna.com/catalog/h1n1/page1.aspx.
Johnson, F.B., "Transport of viral specimens," Clin. Microbiol. Rev. 3(2): 120-131 (1990).
Sponseller, et al., "Influenza A pandemic (H1N1) 2009 virus infection in domestic cat," Emerg. Infect. Dis. (e-publication) (2010).
PCT Patentability Report for PCT/US2010/043546, dated Jan. 31, 2012.
PCT Search Report and Patentability Report for PCT/US2008/074521, dated Mar. 2, 2010.
Master Your PCR Domain.
Buck et al. BioTechniques vol. 27, pp. 528-536, Sep. 1999.
Characterization of Novel Influenza 2005.
Daum, et al., Abstract and Poster—"Development of a Real Time Reverse-Transcription PCR (RRT-PCR) Assay for Detection of Influenza A H1N1 2009 from Clinical Respiratory Specimens," Pediatric Infectious Disease Conference ESPID, Nice, France, May 5-8, 2010.
De Silva at al. Influenza A virus (A/Nonthaburi/102/2009(H1N1)) segment 4 hemagglutinin (HA) gene, partial cds. Genbank Accession No. GQ 132184.1, submitted May 9, 2009.
Hindiyeh et al. Journal of Clinical Microbiology, vol. 43, No. 2, pp. 589-595, Feb. 2005.
"Adamantane Resistance Among Influenza, etc.", JAMA, Feb. 22, 2006, vol. 295, No. 8, pp. 891-894.
Lowe et al. A computer program for selection of oligonucleotide primers for polymerase chain reactions. Nucleic Acids Research (1990) vol. 18, No. 7, pp. 1757-1761.
Luke T. Daum et al., "Portugal Meeting Poster (Introduction, Materials, and Methods, Results, Discussion)," (2008).
Denhart, M., and Doraiswamy, V., "Master Your PCR Domain!" Promega Notes, 78: 9-12 (2001).
http://www.ncbi.nlm.nih.gov/genomes/FLU/SwineF1u2009.html.
NCBI Influenza Virus Resource "CLE I. GenBank Sequence from Pandemic (H1N1) 2009 Viruses". 1237 pages.
Pamphlet—"Prime PCR System"—Longhorn Vaccines & Disagnostics.

(56) References Cited

OTHER PUBLICATIONS

Magari, R.T., Assessing shelf life using real-time and accelerated stability tests, BioPharm Nov. 2003.
"Taq PCR Master Mix (2x)," USB Corp., (2007).
"Immunoflourescence and Fluorescent-Antibody Techniques", Tortora, et al., Microbiology—An Introduction, Fourth Edition, 1992, pp. 461-463.
World Health Organization, "CDC protocol of realtime RTPCR for influenza A (H1N1)," Apr. 28, 2009.
Wiecek, A., "Pocket PCR: The Whole Chain Reaction in His Hand," Biotechniques.com, Oct. 26, 2010.
Danila Valmori et al. "Use of human universally antigenic tetanus toxin T cell epitopes as carriers for human vaccination" Journal of Immunology Jul. 15, 1992.
PCT Search Report for PCT/US2008/074521 dated Feb. 13, 2009.
PCT Written Opinion for PCT/US2008/074521 dated May 3, 2009.
PCT Search Report for PCT/US10/43546 dated Nov. 16, 2010.
De Folette et al. Vaccine Jun. 12, 2006, vol. 24, No. 44-46, pp. 6597-6601.
Galarza et al. Viral Immunity 2005, vol. 18, No. 2, pp. 365-372.
Arend et al. Infection and Immunity, 2000, vol. 68, No. 6, pp. 3314-3321.
Tolman, et al., "Cyclic V3-Loop Related HIV-1 Conjugate Vaccines," Int. J. Peptide Protein Res., 41, pp. 455-466 (1993).
Conley, et al., "Immunogenicity of Synthetic HIV-1 Gp120 V3-Loop Peptide-Conjugate Immunogens," Vaccine, 12(5), pp. 445-451 (1994).
Schneider, et al., "Induction of CD8+T Cells Using Heterologous Prime-Boost Immunisation Strategies," Immunol. Rev., 170, pp. 29-38 (1999).
Tanghe, et al., "Improved Immunogenicity and Protective Efficacy of a Tuberculosis DNA Vaccine Encoding Ag85 by Protein Boosting," Infect. and Immun., 69(5), pp. 3041-3047 (2001).
Gonzalo, et al., "A Heterologous Prime-Boost Regime Using DNA and Recombinant Vaccinia Virus Expressing the Leishmania infantum P36/Lack Antigen Protects BALB/c Mice from Cutaneous Leishmaniasis," Vaccine, 20, pp. 1226-1231 (2002).
Meyer, et al., "Complement-Mediated Enhancement of Antibody Function for Neutralization of Pseudotype Virus Containing Hepatitis C Virus E2 Chimeric Glycoprotein," J. of Virol., 76(5) pp. 2150-2158 (2002).
Robinson, "New Hope for an AIDS Vaccine," Nat. Rev. Immunol., 2, pp. 239-250 (Apr. 2002).
Lu, et al., "Multiepitope Trojan Antigen Peptide Vaccines for the Induction of Antitumor CTL and Th Immune Responses," J. of Immunol., 172, pp. 4575-4582 (2004).
Westerfield, et al., "Peptides Delivered by Immunostimulating Reconsituted Influenza Virosomes," J. of Peptide Sci., 11(11), pp. 707-712 (2005).
Gerhard, et al., "Prospects for Universal Influenza Virus," Emerging Infectious Diseases, 12(4), pp. 569-574 (Apr. 2006).
Luo, "Structural Biology: Antiviral Drugs Fit for a Purpose," Nature, 443, pp. 37-38 (Sep. 1, 2006).
PepTcell Ltd., "Technology," http://www.peptcell.com/technology.aspx (2007).
Stoloff, et al., "Synthetic Multi-Epitope Peptides Idenitifed in Silico Induce Protective Immunity Against Multiple Influeza Serotypes," Eur. J. of Immunol., 37(9), pp. 2441-2449 (Aug. 2, 2007).
Depla, et al., "Rational Design of a Multiepitope Vaccine Encoding T-Lymphocyte Epitopes for Treatment of Chronic Hepatitis B Virus Infections," J. of Virol., 82(1), pp. 435-450 (Jan. 2008).
Chien et al. J. Clin. Microbiol. 1999, vol. 37, No. 5, 1393-1397.
Ishioka et al. J. Immunol. vol. 162, pp. 3915-3925.
Lederman et al. Molecular Immunology 1991, vol. 28, No. 11, pp. 1171-1181.
PCT Search Report for PCT/US2007/078025 dated Oct. 28, 2008.
PCT Written Opinion for PCT/US2007/078025 dated Mar. 17, 2009.
PCT Search Report for PCT/US2008/078499 dated Jul. 23, 2009.

Miyazaki, et al., "Development of a monolithic silica extraction top for the analysis of proteins," J. Chromatogr. A., 1043(1): 19-25 (2004) [abstract only].
PCT Patentability Report for PCT/US2012/35253, dated Sep. 21, 2012.
Taiwan Office Action dated Aug. 20, 2012.
PCT Search Report for PCT/US10/31716 dated Jul. 28, 2010.
PCT Written Opinion for PCT/US10/31716 dated Oct. 25, 2011.
Kutyavin et al. 3'-Minor groove binder-DNA probes increase sequence specifity at PCR extension temperatures. Nucleic Acids Res. (2000) vol. 28, No. 2, pp. 655-661.
Morrë, et al., "RNA Amplification by Nucleic Acid Sequence-Based Amplification with an Internal Standard Enables Reliable Detection of *Chlamydia trachomatis* in Cervical Scrapings and Urine Samples," J. of Clinical Microbial., 34(12): 3108-3114 (1996).
Rosenstraus, et al., "An Internal Control for Routine Diagnostic PCR: Design, Properties, and Effect on Clinical Performance," J. of Clinical Microbial., 36(1): 191-197 (1998).
Daum, et al., Abstract and Poster—"Development of a Real Time Reverse-Transcription PCR (RRT-PCR) Assay for Detection of Influenza A H1N1 2009 From Clinical Respiratory Specimens," *Pediatric Infectious Disease Conference ESPID*, Nice, France, May 5-8, 2009.
Daum, et al., Abstract—"A Molecular Transport Medium (MTM) for Pathogen Inactivation, Ambient Transport and Preservation of RNA from Clinical Samples," *ICAAC*, Boston, MA, Sep. 12-15, 2010.
U.S. Appl. No. 12/243,949, filed Oct. 1, 2008, Fischer et al.
U.S. Appl. No. 12/426,890, filed Apr. 20, 2009, Fischer et al.
Chomczynski, P. and Sacchi, N., "Single-Step Method of RNA Isolation by Acid Guanidinium Thiocyanate-Phenol-Chloroform Extraction," Anal. Biochem., 162:156-9 (1987).
Tortora, et al., "Tools of Biochemistry 5A—Ways to Isolate and Purify Proteins and Other Macromolecules," *Microbiology—An Introduction*, pp. 152-155, 4$^{th}$ Ed., The Benjamin/Cummings Publishing Company, Inc., United States (1992).
Ramanujam. R. et al., "Room-Temperature-Stable PCR Reagents." Cold Spring Harbor Laboratory Press. *PCR Methods and Appl.*, 3:75-76 (1993).
Wolff, C. et al, "Single-Tube Nested PCR With Room-Temperature-Stable Reagents," Cold Spring Harbor Laboratory Press, *PCR Methods and Appl.*, 4:376-79 (1995).
Matthews, et al., "Immunofluorescence and Fluorescent Antibody Techniques," *Biochemistry*, pp. 461-463, 2$^{nd}$ Ed., The Benjamin/Cummings Publishing Company, Inc., United States (1996).
Schultz, C.L. et al.. "A Lysis, Storage, and Transportation Buffer for Long-Term, Room-Temperature Preservation of Human Clinical Lymphoid Tissue Samples Yielding High Molecular Weight Genomic DNA Suitable for Molecular Diagnosis," Am. J. Clin. Pathol., 111(6):748-52 (1999).
Daum, L.T. et al., "Genetic and Antigenetic Analysis of the First A/New Caledonia/20/99-Like H1N1 Influenza Isolates Reported in the Americas," *Emerg. Infect. Dis.*, 8(4):408-12 (Apr. 2002).
De Moreau de Gerbehaye, A.I. et al., "Stable Hepatitis C Virus RNA Detection by RT-PCR During Four Days Storage," BioMed Central, *BMC Infectious Diseases*, 2:22 (2002).
Daum, L.T. et al., "A Rapid, Single-Step Multiplex Reverse Transcription-PCR Assay for the Detection of Human H1N1, H3N2 and B Influenza Viruses," J. of Clinic. Virol., 25(3): 345-50 (2002).
Spackman, E. et al., "Development of a Real-Time Reverse Transcriptase PCR Assay for Type A Influenza Virus and the Avian H5 and H7 Hemagglutinin Subtypes," J. of Clinic. Microbiol., 40(9): 3256-60 (2002).
Blacksell, S.D. et al., "The Effect of Sample Degradation and RNA Stabilization on Classical Swine Fever Virus RT-PCR and ELISA methods," J. Virol. Methods, 118(1):33-7 (2004).
Canas, L.C., "Clinical Laboratory: Selection, Collection, and Transport of Specimens for Viral Cultures," Department of the Air Force, Air Force Institute of Operational Health (AFIOH), Epidemiological Surveillance Division, SDE O1 44/5001, *Virol. Proc. Man.*, 1-8 (2005).
Fouchier, R.A.M. et al., "Characterization of a Novel Influenza A Virus Hemagglutinin Subtype (H16) Obtained From Black-Headed Gulls," J. of Virol., 79(5):2814-22 (Mar. 2005).

(56) References Cited

OTHER PUBLICATIONS

Krafft, A.E. et al.. "Evaluation of PCR Testing of Ethanol-Fixed Nasal Swab Specimens as an Augmented Surveillance Strategy for Influenza Virus and Adenovirus Identification," *J. of Clinic. Microbiol.*, 43(4):1768-75 (Apr. 2005).
Pheng, O.C. et al., "Temperature Related Storage Evaluation of an RT-PCR Test Kit for the Detection of Dengue Infection in Mosquitoes," (Research Note), *Tropical Biomedicine*, 22(1):73-6 (2005).
"USB Taq PCR Master Mix in qPCR," USB Corporation, *Tech Tips*, 207 (2005).
Bright, R.A., et al., "Adamantane Resistance Among Influenza A Viruses Isolated Early During the 2005-2006 Influenza Season in the United States," *JAMA*, 295(8):891-4 (Feb. 22, 2006).
"Collecting, Preserving and Shipping Specimens for the Diagnosis of Avian Influenza A (H5N1) Virus Infection: Guide for Field Operations," WHO/CDS/EPR/ARO/2006.1 (2006).
Das, A. et al., "Development of an Internal Positive Control for Rapid Diagnosis of Avian Influenza Virus Infections by Real-Time Reverse Transcription-PCR with Lyophilized Reagents," *J. of Clinic, Microbiol.*, 44(9):3065-73 (Sep. 2006).
Daum, L.T., et al., "Molecular Analysis of Isolates From Influenza B Outbreaks in the U.S. and Nepal, 2005," *Arch. of Virol.*, 151:1863-1874 (2006).
Lin, B. et al., "Broad-Spectrum Respiratory Tract Pathogen Identification Using Resequencing DNA Microarrays," *Genome Res.*, 16(4): 527-35 (2006).
Mohany, J. et al., "Multiplex RT-PCR for Detecting Nineteen Respiratory Viruses," *J. of Clinic. Virol.*, 36: S9 (2006).
Daum, L.T. et al., "Real-Time RT-PCR Assays for Type and Subtype Detection of Influenza A and B Viruses," *Influenza & Other Resp. Viruses*, 1(4): 167-75 (2007).
"PCR-Ready Clear Supreme™," Syntezza Bioscience Ltd., available at http://www.syntezza.com/egt/PCR-Ready_Clear_Supreme.pdf (2006).
Wang, Z., et al., "Identifying Influenza Viruses with Resequencing Microarrays," *Emerg. Infect. Dis.* 12(4):638-46 (2006).
"TechNotes Newsletter," *Applied Biosystems*, 14(4):1-37 (2007).
Blow, J.A. et al., "Viral Nucleic Acid Stabilization by RNA Extraction Agent," *J. of Virol. Meth.*, 150:41-4 (2008).
Daum, L.T., et al., "Poster—A Rapid, Simplified Collection-to-Detection System for Typing and Subtyping Influenza Viruses Using Real-Time RT-PCR and Culture," *American Society for Microbiology (ASM) Conference on Emerging Technologies of Medical Importance for the Diagnosis of Infectious Diseases and the Detection of Pathogenic Microbes*, Beijing, China, (2008).
Daum, L.T., et al., "Abstract—Quantitation of Influenza A Virus From Nasal and Lung Tissue of Cotton Rats Using Real-Time RT-PCR and Culture," 26th *Annual Meeting of the European Society for Pediatric Infectious Diseases*, Graz, Austria, (2008).
Daum, L.T., et al., "Abstract—Development and Clinical Evaluation of Rapid Real-Time RT-PCR Assays for Detection of Influenza A and B Viruses," 26th *Annual Meeting of the European Society for Pediatric Infectious Diseases*, Graz, Austria, (2008).
Daum, L.T., et al., "Poster—A Novel Specimen Collection Solution for Molecular Diagnostic Applications," *The Pediatric Academic Societies (PAS) Annual Meeting*, Honolulu, HI (2008).
Daum, L.T., et al., "Poster—Real-Time RT-PCR Detection of Influenza A Virus in Asymptomatic Culture-Negative Cotton Rats," *The Pediatric Academic Societies (PAS) Annual Meeting*, Honolulu, HI (2008).
Daum, L.T., et al., "Poster—Detection and Molecular Characterization of Clinical Influenza A and B Viruses from Original Nasal Wash Specimens Preserved in PrimeStore™," *The 3*[th] *European Conference on Influenza*, Vilamoura, Portugal (2008).
Daum. L.T., et al., "Real-Time RT-PCR Detection of Influenza Virus Within Symptomatic and Asymptomatic Family Members," *The 48*[th] *Annual IDSA/ICAAC*, Washington D.C. (2008).
European Patent Office, "PCT International Search Report, PCT Written Opinion of the International Searching Authority—Application No. PCT/US2007/078025," Oct. 28, 2008, 9 pages.

"Abstracts—27th Annual Meeting of the European Society for Paediatric Infectious Disease, Brussels, Belgium, Jun. 9-13, 2009," *The Ped. Infect. Dis. J.*, 28(6):e1, e75, e202, d229 (Jun. 2009).
Borns, M. et al, "Most Accurate PCR Enzyme Inproved With Hot Start Feature," Biocompare, available at http://www.biocompare.com/technicalarticle/212/Most-Accurate-PCR-Enzyme-Improved-With-Hot-Start-Feature-from-Stratagene.html (last visited Aug. 24, 2009).
"KOD Hot Start DNA Polymerase," Novagen, available at http://www.emdbiosciences.com/Products/ProductDisplay.asp?catno=71086 (last visited Aug. 24, 2009).
"R.A.P.I.D® System," Idaho Technology Inc., available at http://www.idahotech.com/RAPID/Rapid-Water.html (last visited Aug. 24, 2009).
"AgPath-ID™ One-Step RT-PCR Kit," Applied Biosystems, available at http://www.abion.com/techlib/prot/bp_1005.pdf (last visited Aug. 24, 2009).
"PCR Optimization: Reaction Conditions and Components," Applied Biosystems, Part No. 4371091, Revision C, pp. 1-6 available at http://www3.appliedbiosystems.com/cms/groups/mcb_marketing/documents/generaldocuments/cms_042520.pdf.(last visited Aug. 24, 2009).
"Single Tube PCR Kit Manual," Takara Bio Inc., Cat. #RR021, V.02.09, pp. 1-6 available at http://www.takara-bio.us/files/manuals/TAK_RR021_TM.pdf (last visited Aug. 24, 2009).
"Luminex Confirms Effectiveness of xTAG® Respiratory Viral Panel for Swine Flu Surveillance," *Medical News Today*, available at http://www.medicalnewstoday.com/printerfriendlynews.php?newsid=148498 (May 1, 2009).
"Luminex Receives FDA Clearance for an Update to the xTAG® Respiratory Viral Panel Package Insert Package Insert to Include Data from Two New Publications on 2009 Influenza A/H1N1," available at http://phx.corporate-ir.net/phoenix.zhtml?c=79403&p=irol-newsArticle&ID=1307416&highlight= (Jul. 14, 2009).
European Patent Office, "PCT International Search Report, PCT Written Opinion of the International Searching Authority—Application No. PCT/US2008/078499," Aug. 4, 2009, 13 pages.
U.S. Appl. No. 12/510,968, filed Jul. 28, 2009, Fischer.
http://www.ncbi.nim.nih.gov/genomes/FLU/SwineFLU2009.html. NCBI Influenza Virus Resource "CLE I. GenBank Sequence from Pandemic (H1N1) 2009 Viruses". 1237 pages.
De Folette et al. Vaccine Jun. 12, 2006 vol. 24, No. 44-46, pp. 6597-6601.
Geysen, et al., "Use of Peptide Synthesis to Probe Viral Antigens for Epitopes to a Resolution of a Single Amino Acid," Proc. Natl. Acad. Sci., 81, pp. 3998-4002 (1984).
Valmori, et al., "Use of Human Universally Antigenic Tetanus Toxin T Cell Epitopes as Carriers for Human Vaccination," J. of Immunol., 149(2), pp. 717-721 (1992).
Henke et al., "Betaine Improves the PCR Amplification of GC-Rich DNA Sequences," Nucleic Acids Research 25(19): 3957-3958 (1997).
Yue et al., "Detection of rifampin-resistant Mycobacterium tuberculosis strains by using a specialized oligonucleotide microarray," Diagnostic Microbiology and Infectious Disease, 48(1): 47-54 (2004).
U.S. Appl. No. 12/243,949, filed Dec. 17, 2009, Fischer et al.
U.S. Appl. No. 13/332,204, Fischer et al.
IL Exam Report for PCT/US2007/078025, dated Mar. 7, 2013.
EPO Exam Report for EP12180376, dated Feb. 8, 2013.
Canadian Office Action for application No. 2759028, dated Apr. 12, 2013.
PCT Search Report for PCT/US13/32354, dated May 31, 2013.
Chinese Office Action for Application No. 201080028416.4.
Chinese Search Report for Application No. 201080028416.4.
Austalian Exam Report for Application No. 2012239385, dated Oct. 9, 2013.
Austalian Exam Report for Application No. 2012211365, dated Oct. 9, 2013.
Max, et al Reliability of PCR-based detection of occult tumour cells: lessons from real-time RT-PCR.

(56) References Cited

OTHER PUBLICATIONS

EP Search Report for Application No. 13175959, dated Nov. 18, 2013.
PCT Search and Patentability Report for PCT/US2013/077038, dated Mar. 10, 2014.
CA Office Action for CA Application No. 2701168, dated Mar. 4, 2014.
Anderson, et al, "DNA and RNA-derived assessments of fungal community composition in soil amended with sewage sludge rich in cadmium, copper and zinc," Soil Biology and Biochemistry, Pegamon, Oxford, GB, vol. 40, No. 9, Sep. 1, 2008.
Liao, J et al, "Telomerase activity in oral and maaxillofacial tumors," Oral Oncology, Elsevier Science, Oxford, GB, vol. 36, No. 4, Jul. 1, 2000.
Daum, L, et al, "A clinical specimen collection and transport medium for molecular diagnostic and genomic applications," Epidemiology and Infection, Cambridge University Press, Cambridge, GB, vol. 139, No. 11, Dec. 16, 2010.
Daum, L. et al, "A rapid, collection-to-detection PCR system of the universal detection of mycobacterium tuberculosis," Jun. 29, 2011, pp. 1-1.
Papagrigorakis, M. et al, "DNA examination of ancient dental pulp incriminates typhoid fever as a probable cause of the plague of Athens," International Journal of Infectious Diseases, Hamilton, CA, vol. 10, No. 3, May 1, 2006.
Buys, et al, "Applying AFLPs in Aizoaceae: the Delosperma herbeum complex as a case study," Biochemical Systematics and Ecology, Pergamon Press, GB, vol. 36, No. 2, Dec. 13, 2007.

* cited by examiner

| | Qiagen Viral Mini | | Ambion RNaqueous Mini | | Ambion AI/NCD MagMax | |
|---|---|---|---|---|---|---|
| | One Step− | One-Step+ | One Step− | One-Step+ | One Step− | One-Step+ |
| Real-Time CT Value | 19.25 | 19.08 | 32.83* | 30.39* | 23.95 | 21.26 |
| Viral Copies Detected | $4.7 \times 10^9$ | $5.5 \times 10^9$ | $2.5 \times 10^5$ | $6.2 \times 10^{5*}$ | $1.12 \times 10^{10}$ | $2.10 \times 10^{10}$ |

FIG.2

| Sample | Day 1 | Day 3 | Day 4 |
|---|---|---|---|
| One-Step Solution | 23.97 | 21.37 | 31.38 |
| RNA Storage Solution (Ambion) | 25.35 | 32.70 | 32.20 |
| Water | 24.39 | 32.17 | 32.27 |

|  | Blood Tube | | | |
|---|---|---|---|---|
|  | EDTA | NaCitrate | LiHeparin | NaHeparin |
| PrimeStore™ | 33.7804 | 31.9677 | 32.5538 | 33.118 |
|  | 34.7485 | 32.0509 | 32.8927 | 32.984 |
| AVG: | 34.26445 | 32.0093 | 32.72325 | 33.051 |
| Qiagen | 35.3054 | 33.4051 | 34.4903 | 34.6428 |
|  | 34.7485 | 33.4051 | 35.0378 | 35.3937 |
| AVG: | 35.02695 | 33.4051 | 34.76405 | 35.01825 |

FIG. 14B

| PrimeStore™-Blood Extraction | | |
|---|---|---|
| 1pg | 0.1pg | |
| 32.7715 | 36.434 | |
| 33.2488 | 37.0442 | |
| 33.01015 | 36.7391 | AVG |
| 0.337502067 | 0.431476558 | STDEV |

| Qiagen-Blood Extraction | | |
|---|---|---|
| 1pg | 0.1pg | |
| 35.8461 | 37.5771 | |
| 37.01 | 38.1878 | |
| 36.42805 | 37.88245 | AVG |
| 0.823001583 | 0.431830111 | STDEV |

FIG.14C

SEQUENCE LISTING

```
<160> NUMBER OF SEQ ID NOS: 26

<210> SEQ ID NO 1
<211> LENGTH: 100
<212> TYPE: DNA
<213> ORGANISM: Artificial Sequence
<220> FEATURE:
<223> OTHER INFORMATION: Synthetic Oligonucleotide

<400> SEQUENCE: 1
gtgcagtcag tccctcggtt aaagtctcga gtcgctctgt caaaatatcc gtaccgtagt      60
cgatgcgagc gagtccgatc agtccaggtt tcaaagtcaa                           100

<210> SEQ ID NO 2
<211> LENGTH: 110
<212> TYPE: RNA
<213> ORGANISM: Artificial Sequence
<220> FEATURE:
<223> OTHER INFORMATION: Synthetic Oligonucleotide

<400> SEQUENCE: 2
cccuuagcag cacgucaguc agggagccaa uuucagagcu cagcgagaca guuuuauagg      60
cauggcauca gcuacgcucg cucaggcuag ucagguccaa aguuucaguu                110

<210> SEQ ID NO 3
<211> LENGTH: 104
<212> TYPE: RNA
<213> ORGANISM: Artificial Sequence
<220> FEATURE:
<223> OTHER INFORMATION: Synthetic Oligonucleotide

<400> SEQUENCE: 3
cuuagcagca cgucagucag ggagccaauu cagagcucag cgagacaguu uauagcaugg      60
caucagcuac gcucgcucag gcuagucagg uccaaaguuu cagu                      104
```

```
<210> SEQ ID NO 4
<211> LENGTH: 100
<212> TYPE: RNA
<213> ORGANISM: Artificial Sequence
<220> FEATURE:
<223> OTHER INFORMATION: Synthetic Oligonucleotide

<400> SEQUENCE: 4
uuagcagcac gucagucagg gagccaauca gagcucagcg agacaguuau aggcauggca      60
ucagcuacgc ucgcucaggc uagucaggguc caaaguuuca                          100

<210> SEQ ID NO 5
<211> LENGTH: 100
<212> TYPE: RNA
<213> ORGANISM: Artificial Sequence
<220> FEATURE:
<223> OTHER INFORMATION: Synthetic Oligonucleotide

<400> SEQUENCE: 5
ccuagcagca cgucagucag ggagccauuc agagcucagc gagacaguua uaggcauggc      60
aucagcuacg cucgcucagg cuagucaggu ccaaguucag                           100

<210> SEQ ID NO 6
<211> LENGTH: 102
<212> TYPE: RNA
<213> ORGANISM: Artificial Sequence
<220> FEATURE:
<223> OTHER INFORMATION: Synthetic Oligonucleotide

<400> SEQUENCE: 6
agcagcacgu cagucaggga gccaauuuca gagcucagcg agacaguauu uaggcaugca      60
ucagcuacgc ucgcucagcc uagucacguc caauguauca gu                        102

<210> SEQ ID NO 7
<211> LENGTH: 101
<212> TYPE: RNA
<213> ORGANISM: Artificial Sequence
<220> FEATURE:
<223> OTHER INFORMATION: Synthetic Oligonucleotide

<400> SEQUENCE: 7
cuagcagcag ucagcaggga gccaauuuca gaucagcgag acaguuuaua gccgcaugcc      60
aucagcuacg cucgcuucag cuagucaguc aaguuuucag u                         101

<210> SEQ ID NO 8
<211> LENGTH: 99
<212> TYPE: RNA
<213> ORGANISM: Artificial Sequence
<220> FEATURE:
<223> OTHER INFORMATION: Synthetic Oligonucleotide

<400> SEQUENCE: 8
uagcagcacg ucagucaggg agccaauuca gagcucagcg agacaguuag gcaugccauc      60
aacuacgcuc gcucagccua gucacguccca aguucagaa                            99

<210> SEQ ID NO 9
<211> LENGTH: 95
<212> TYPE: RNA
<213> ORGANISM: Artificial Sequence
<220> FEATURE:
<223> OTHER INFORMATION: Synthetic Oligonucleotide
```

```
<400> SEQUENCE: 9
ccuagcagca cgucgucagg agccaauuca gagcucagga gacaguuuau agcaugcauc    60
agcuagcucg cucagcuagu cagucaaguu caguu                              95

<210> SEQ ID NO 10
<211> LENGTH: 104
<212> TYPE: RNA
<213> ORGANISM: Artificial Sequence
<220> FEATURE:
<223> OTHER INFORMATION: Synthetic Oligonucleotide

<400> SEQUENCE: 10
cuuacgcagc accggucagu auucgcggag ccuauucaga gcucagcgag acaguuauag    60
caugcaucag cuacccucgc ucaggcuguc aggucaguuc gauu                    104

<210> SEQ ID NO 11
<211> LENGTH: 93
<212> TYPE: RNA
<213> ORGANISM: Artificial Sequence
<220> FEATURE:
<223> OTHER INFORMATION: Synthetic Oligonucleotide

<400> SEQUENCE: 11
uagcagcacg ucagucagag caucagagcu cagcgagaca gaauuaaagc ccaugcauca    60
gcugcugcuc agcuagucag uccaagucca gcu                                93

<210> SEQ ID NO 12
<211> LENGTH: 97
<212> TYPE: RNA
<213> ORGANISM: Artificial Sequence
<220> FEATURE:
<223> OTHER INFORMATION: Synthetic Oligonucleotide

<400> SEQUENCE: 12
cccuuagcag cacgucaguc agggagccaa uuucagagcu cagcaguuau aggcauggca    60
ucagcuacgc ucgcaguagu cagguccaaa guucagu                            97

<210> SEQ ID NO 13
<211> LENGTH: 89
<212> TYPE: RNA
<213> ORGANISM: Artificial Sequence
<220> FEATURE:
<223> OTHER INFORMATION: Synthetic Oligonucleotide

<400> SEQUENCE: 13
cagcacguca gucagagcau cagagcucag cgagacagua uaggcaugca ucagcacgcu    60
cucaggcuag ucagcucgaa agucagaau                                     89

<210> SEQ ID NO 14
<211> LENGTH: 126
<212> TYPE: DNA
<213> ORGANISM: Artificial Sequence
<220> FEATURE:
<223> OTHER INFORMATION: Synthetic Oligonucleotide  N = any nucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
```

```
<220> FEATURE:
<221> NAME/KEY: misc_feature
<222> LOCATION: (126)..(126)
<223> OTHER INFORMATION: n is a, c, g, or t

<400> SEQUENCE: 14
ntattaatac gactcactat agggngtgca gtcagtccct cggttaaagt ctcgagtcgc    60
tctgtcaaaa tatccgtacc gtagtcgatg cgagcgagtc cgatcagtcc aggtttcaaa  120 gtcaan                                                             126

<210> SEQ ID NO 15
<211> LENGTH: 141
<212> TYPE: DNA
<213> ORGANISM: Artificial Sequence
<220> FEATURE:
<223> OTHER INFORMATION: Synthetic Oligonucleotide

<400> SEQUENCE: 15
atcgtattaa tacgactcac tagggaat cgtcgtgcag tcagtccctc ggttaaagtc     60
tcgagtcgct ctgtcaaaat atccgtaccg tagtcgatgc gagcgagtcc gatcagtcca  120
ggtttcaaag tcaaatgact a                                            141

<210> SEQ ID NO 16
<211> LENGTH: 141
<212> TYPE: DNA
<213> ORGANISM: Artificial Sequence
<220> FEATURE:
<223> OTHER INFORMATION: Synthetic Oligonucleotide

<400> SEQUENCE: 16
atcgtattaa tacgactcac tagggaat cgtcgtgcag tcagtccctc ggttaaagtc     60
tcgagtcgct ctgtcaaaat atccgtaccg tagtcgatgc gagcgagtcc gatcagtcca  120
ggtttcaaag tcaaatgact a                                            141

<210> SEQ ID NO 17
<211> LENGTH: 141
<212> TYPE: DNA
<213> ORGANISM: Artificial Sequence
<220> FEATURE:
<223> OTHER INFORMATION: Synthetic Oligonucleotide

<400> SEQUENCE: 17
atcgtattaa tacgactcac tagggaat cgtcgtgcag tcagtccctc ggttaaagtc     60
tcgagtcgct ctgtcaaaat atccgtaccg tagtcgatgc gagcgagtcc gatcagtcca  120
ggtttcaaag tcaaatgact a                                            141

<210> SEQ ID NO 18
<211> LENGTH: 127
<212> TYPE: DNA
<213> ORGANISM: Artificial Sequence
<220> FEATURE:
<223> OTHER INFORMATION: Synthetic Oligonucleotide

<400> SEQUENCE: 18
atattaatac gactcactat agggagtgca gtcagtccct cggttaaagt ctcgagtcgc    60
tctgtcaaaa tatccgtacc gtagtcgatg cgagcgagtc cgatcagtcc aggtttcaaa  120
gtcaaat                                                            127
```

<210> SEQ ID NO 19
<211> LENGTH: 127
<212> TYPE: DNA
<213> ORGANISM: Artificial Sequence
<220> FEATURE:
<223> OTHER INFORMATION: Synthetic Oligonucleotide

<400> SEQUENCE: 19
atattaatac gactcactat agggagtgca gtcagtccct cggttaaagt ctcgagtcgc    60
tctgtcaaaa tatccgtacc gtagtcgatg cgagcgagtc cgatcagtcc aggttttcaaa   120 gtcaaat                                                             127

<210> SEQ ID NO 20
<211> LENGTH: 127
<212> TYPE: DNA
<213> ORGANISM: Artificial Sequence
<220> FEATURE:
<223> OTHER INFORMATION: Synthetic Olignonucleotide

<400> SEQUENCE: 20
atattaatac gactcactat agggagtgca gtcagtccct cggttaaagt ctcgagtcgc    60
tctgtcaaaa tatccgtacc gtagtcgatg cgagcgagtc cgatcagtcc aggttttcaaa   120 gtcaaat                                                             127

<210> SEQ ID NO 21
<211> LENGTH: 123
<212> TYPE: DNA
<213> ORGANISM: Artificial Sequence
<220> FEATURE:
<223> OTHER INFORMATION: Synthetic Oligonucleotide

<400> SEQUENCE: 21
tattaatacg actcactata ggggtgcagt cagtccctcg gttaaagtct cgagtcgctc    60
tgtcaaaata tccgtaccgt agtcgatgcg agcgagtccg atcagtccag gtttcaaagt   120
caa                                                                 123

<210> SEQ ID NO 22
<211> LENGTH: 123
<212> TYPE: DNA
<213> ORGANISM: Artificial Sequence
<220> FEATURE:
<223> OTHER INFORMATION: Synthetic Oligonucleotide

<400> SEQUENCE: 22
tattaatacg actcactata ggggtgcagt cagtccctcg gttaaagtct cgagtcgctc    60
tgtcaaaata tccgtaccgt agtcgatgcg agcgagtccg atcagtccag gtttcaaagt   120
caa                                                                 123

<210> SEQ ID NO 23
<211> LENGTH: 123
<212> TYPE: DNA
<213> ORGANISM: Artificial Sequence
<220> FEATURE:
<223> OTHER INFORMATION: Synthetic Oligonucleotide

<400> SEQUENCE: 23
tattaatacg actcactata ggggtgcagt cagtccctcg gttaaagtct cgagtcgctc    60
tgtcaaaata tccgtaccgt agtcgatgcg agcgagtccg atcagtccag gtttcaaagt   120
caa                                                                 123

```
<210> SEQ ID NO 24
<211> LENGTH: 21
<212> TYPE: DNA
<213> ORGANISM: Artificial Sequence
<220> FEATURE:
<223> OTHER INFORMATION: Synthetic Oligonucleotide Forward Primer

<400> SEQUENCE: 24
gtgcagtcag tccctcggtt a                                            21

<210> SEQ ID NO 25
<211> LENGTH: 24
<212> TYPE: DNA
<213> ORGANISM: Artificial Sequence
<220> FEATURE:
<223> OTHER INFORMATION: Synthetic Oligonucleotide Reverse Primer

<400> SEQUENCE: 25
ttgactttga aacctggact gatc                                         24

<210> SEQ ID NO 26
<211> LENGTH: 20
<212> TYPE: DNA
<213> ORGANISM: Artificial Sequence
<220> FEATURE:
<223> OTHER INFORMATION: Synthetic Olignonucleotide Probe

<400> SEQUENCE: 26
aaatatccgt accgtagtcg                                              20
```

BIOLOGICAL SPECIMEN COLLECTION/TRANSPORT COMPOSITIONS AND METHODS

CROSS-REFERENCE TO RELATED APPLICATIONS

The present application is a continuation of U.S. patent application Ser. No. 12/426,890, filed Apr. 20, 2010, which is a continuation-in-part of U.S. patent application Ser. No. 12/243,949, and International Application No. PCT/US2008/078499, both filed Oct. 1, 2008, now pending, and claims the benefit of U.S. Provisional Application No. 60/976,728, filed Oct. 1, 2007, now expired, the entire contents of each of which is specifically incorporated herein by express reference thereto.

FIELD OF THE INVENTION

The invention relates to compositions and methods for collection, transport, and storage of a biological sample containing a population of nucleic acids, which can subsequently be isolated, purified and/or characterized using one or more conventional methods or assays.

BACKGROUND OF THE INVENTION

In the field of molecular and diagnostic analysis, the ability to keep nucleic acids in a biological sample (and in particular, those contained in diagnostic samples obtained from human patients) stable, whether the specimen is taken in a remote field location, a doctor's office or in a laboratory, often determines whether the nucleic acids can be successfully analyzed. Nucleic acids in a biological sample quickly degrade and/or denature at room temperature and must generally be stored under freezing temperatures to remain stable; however, some degree of degradation still occurs over time. This problem is magnified when a specimen is collected at a remote field site, or a significant distance from a doctor's office or laboratory environment, and especially where there may be limited, or no, access to consistent and constant cooler/refrigerator/freezer conditions until the sample is analyzed, such as where access to electrical power, or refrigerator/freezer equipment is either unreliable, or non-existent. The problems associated with the collection and handling of biological specimens from which it is desirable to obtain nucleic acids are further exacerbated when the desired nucleic acids for downstream analysis include ribonucleic acid (RNA), which is particularly susceptible to degradation by endogenous or exogenous nuclease activity. Commercially-available specimen transport methods often use special transport media for biological samples for transport from point of collection to point of analysis, and in particular, packaging that imposes limitations on the time a sample may be stored, requires continual sample maintenance at low temperatures, even during transport or extended storage, and practically limits the time and distances possible between the collection site and the diagnostic laboratory.

In addition to concerns regarding specimen stability, there are often additional concerns regarding the handling and/or storage of reagents used in storing and transporting the collected samples. For example, the reagents themselves frequently require cold temperatures or other special care to maintain stability. Due to these stability issues, for example, transport of the reagents to a field site, storage at the field site before use, and transport of the biological specimens and reagents back to a testing site is a primary concern.

Another significant concern when working with biological specimens is the potential inoculation, release, or dissemination of live infectious pathogens or biological agents from the specimen into the environment. Specific protocols currently exist that are employed when handling samples that may be infectious or otherwise pose health or safety risks. If the sample is kept viable and/or biologically intact to preserve its integrity for testing, individuals involved in the collection, transfer, and testing process are potentially exposed to highly dangerous contagions. Additionally, innocent bystanders nearby a field or sample collection site (or nearby during transport) can be exposed if a release of the contagion occurs. As a result, the required safety measures typically increase the expense and effort required to move such samples from one location to another.

Until recently, clinical laboratory methods for pathogen detection were labor-intensive, expensive processes that required highly knowledgeable and expert scientists with specific experience. The majority of clinical diagnostic laboratories employed the use of traditional culturing methods that typically require 3 to 7 days for a viral culture—and even longer for some other bacterial targets. Furthermore, traditional culturing requires collection, transport, and laboratory propagation and handling of potentially infectious biological agents such as Ebola, avian influenza, severe acute respiratory syndrome (SARS), etc.

The field of clinical molecular diagnostics changed drastically with the advent of polymerase chain reaction (PCR) in the mid eighties, however, and shortly thereafter with real-time PCR in the mid 90's. Nucleic-acid based detection platforms employing e.g., quantitative real-time PCR (qPCR) or reverse transcriptase PCR (RT-PCR) and quantitative, real-time, reverse transcriptase PCR (qRT-PCR) assays can deliver results in hours versus days required for traditional culture and isolation methods making molecular detection methods the mainstay of modern diagnostic laboratory analysis. Recent improvements in detection chemistries, such as new and improved reporting/quenching fluors, minor groove binders (MGB) (TaqMan MGB™, Applied Biosystems; for a general reference, see also e.g., Baraldi et al., *Pure Appl. Chem.*, 75(2-3):187-194, 2003), and stabilized amplification reagents have paved the way for more sensitive and highly-specific nucleic acid detection assays, and have proved more timely, robust, and economical than antiquated cell culture-based methods. Advances in other nucleic acid detection strategies such as transcription-mediated amplification, ligase chain reaction (LCR), and so-called "laboratory-on-a-chip" multiplexed assays, have also contributed to the transition from culture vials to microarrays in the clinical laboratory.

Several commercial companies (e.g., Qiagen [Valencia, Calif., USA], Roche Applied Science [Indianapolis, Ind., USA], Gen-Probe [San Diego, Calif., USA], and bioMérieux [Durham, N.C., USA]) have developed instruments to automate the nucleic acid extraction process from sample isolation to molecular analysis. For example, the Tigris DTS® (Gen-Probe, San Diego, Calif., USA) automates the entire detection process, and in late 2004 was approved by the U.S. Food and Drug Administration (FDA) for simultaneously detecting *Chlamydia trachomatis* and *Neisseria gonorrhoeae* using Gen-Probe's APTIMA COMBO-2® amplified nucleic acid test (NAT) assay.

In view of the requirement for high-quality nucleic acid samples in contemporary detection and assay systems, there is now a need in the art for safe and facile collection, storage and transport systems that maintain the integrity and quality of nucleic acids contained within a variety of biological samples and specimens. Moreover, there is also now a need for collecting, preserving, and transporting samples (and particularly those containing harmful or pathogenic organisms) in remote or field locations under ambient environmental (i.e., non-ideal) conditions for extended periods of time without refrigerating, freezing, or otherwise special handling of the collection reagent(s), the biological sample itself, or the population of nucleic acids contained therein. Furthermore, there is now a need for less-expensive, and more-convenient collection/transport/storage media that minimize risk of pathogen exposure to workers or innocent bystanders, allow for the use of single-step formulations, and facilitate convenient ambient transportation of biological specimens over long distances or extended periods of time that contain high-fidelity, high-quality nucleic acid populations.

BRIEF SUMMARY OF THE INVENTION

The present invention encompasses new and useful compositions, as well as methods of making and employing them, that may advantageously improve conventional collection, lysis, transport and storage methods for the preparation of nucleic acids from one or more biological sources. Accordingly, the present invention advantageously provides a collection and preservation formulation to inactivate and lyse a biological specimen containing nucleic acids, and preserve nucleic acids (e.g., RNA or DNA) within the biological specimen, preferably all in a single reaction vessel, such that the integrity of the nucleic acids is at least substantially maintained, and preferably entirely maintained, so that a portion of the nucleic acids are readily available for molecular diagnostic analysis. An additional advantage of the present invention is that the formulation can enable the separated or released nucleic acids to remain at least substantially stable, without requiring consistent and constant cooler temperatures, such as refrigeration or freezing.

The one-step formulations disclosed herein accomplish the following principal functions: inactivation or killing of pathogens within the sample; lysis of cells and separation or release of nucleic acids from the cells; inactivation of endogenous or exogenous nucleases and other cellular enzymes to prevent degradation of the nucleic acids present in the sample; and facilitation of collection and handling of the sample at ambient temperatures, stabilization of the nucleic acids during subsequent transport and storage of the sample, preservation of sample integrity through the use of extra-genomic, non-sense RNA carrier molecules that also serve as an internal positive control (IPC) to monitor fidelity of the processed samples.

The ability to achieve all of these desirable functions in a single-step formulation, preferably in a single reaction zone or reaction vessel, is a particularly marked advantage over that presently available. Presently existing technologies do not include a single-step composition that provides for inactivation of biological components containing nucleic acids, release of nucleic acids through lysis of cells and separation or release of nucleic acids, maintenance of the integrity of the liberated population of nucleic acids, and convenient IPCs to quantitate specimen fidelity. The present invention both stabilizes and preserves the integrity of nucleic acids present in the specimen for diagnostic testing, while also providing convenient methods for monitoring the fidelity of the collection medium that employ a readily-detectable, quantifiable RNA carrier molecule.

The one-step formulations of the present invention allow for preferably simultaneous inactivation of biological components containing nucleic acids, lysis and separation or release of nucleic acids, stabilization, and preservation. In one embodiment, some or all of the inactivation, lysis and separation or release, stabilization, and preservation, are sequential. In a preferred embodiment, however, a majority or preferably all of these functions occur simultaneously. In all embodiments, the one-step formulation is combined with the sample to initiate these functions. This is in contrast to previous technology in which inactivation did not necessarily occur, and lysis, stabilization, and preservation occurred in a succession of separate steps, each step typically using one or more distinct reagents and protocols that were separately added.

Unlike prior nucleic acid isolation methods that required numerous sequential steps to minimize errors, avoid reagent incompatibility, and provide stepwise control of results, the present invention provides all these benefits in a single one-step formulation, and also adds the further benefits of maintaining the integrity of the nucleic acids, monitoring the fidelity of the storage/collection/transport process through the use of an internal nonsense RNA carrier molecule, facilitating both higher extraction and purification efficiencies of the sample nucleic acids, and improving their ultimate yield. The one-step formulations of the present invention preferably facilitate simultaneous inactivation of biological components containing nucleic acids, lysis and release of nucleic acids from cellular debris, stabilization, and preservation of nucleic acids reduces the chance for degradation of the population of nucleic acids contained within the biological sample that may occur before, during, or after lysis.

The disclosed compositions were developed and optimized: 1) to facilitate preparation of high-quality nucleic acids from clinical or environmental specimens, 2) to inactivate, kill, or otherwise neutralize potentially infectious pathogens in a biological sample to facilitate safe handling and transport of the collected specimens, and 3) to stabilize released (i.e., 'naked') DNA/RNA for prolonged periods without hydrolysis or nuclease degradation of the released nucleic acids.

The compositions described herein are ideal for clinical, field and deployment use, or for high volume sample collection/extraction. Specimens collected in one or more of the disclosed compositions are biologically inactivated, and may be safely shipped, typically even without refrigeration or dry ice.

In certain embodiments, the addition of nucleic acids (e.g., RNA and/or DNA) is contemplated to be beneficial for a variety of purposes and applications of the disclosed methods: a) as a "carrier" (The addition of small amounts of supplemental RNA/DNA has been previously been shown to augment/increase the overall yield of samples/specimens, particularly original specimens that may contain low amounts of target, i.e., cells, viruses, bacteria); b) as an IPC for downstream molecular processes and to track or monitor the fidelity of the nucleic acid preparation from sample collection to detection; and c) for comparison to a 'calibrator' for downstream quantitative analysis, e.g., qRT-PCR and the like. In such embodiments, one or more known or "control" nucleic acids could be added to the compositions in a final concentration of from about 1 ag to about 1 mg, more preferably from about 1 fg to about 1 µg, and more preferably still, from about 1 pg to about 1 ng.

In an illustrative embodiment, the invention provides an isolated single-stranded (ss) or double-stranded (ds) RNA, DNA, PNA, or hybrid thereof that is useful: (a) as a carrier molecule for aiding in the recovery of polynucleotides from a biological sample suspected of containing nucleic acids, and/or (b) as an IPC (i.e., a "known," "reporter," "control," "standard," or "marker") sequence to monitor the integrity and fidelity of specimen collection and polynucleotide isolation/stabilization. In certain embodiments, the invention provides an isolated ds-RNA, ds-DNA, ds-PNA, or a hybrid thereof that is useful as a carrier molecule and/or an IPC. In other embodiments, the invention provides an isolated ssRNA, ssDNA, ssPNA, or a hybrid thereof that is useful as a carrier molecule and/or as an IPC sequence. In exemplary embodiments, the invention provides an isolated ssRNA molecule that is useful as both a carrier molecule and an IPC sequence.

Such molecules can be isolated from natural sources, prepared in the laboratory, or alternatively, a hybrid containing both native- and non-native sequences. As noted herein, because the compositions of the invention are particularly useful for the isolation and characterization of biological specimens obtained from mammalian (and in particular, human) sources that are suspected of containing polynucleotides of pathogen-origin, it is preferable that the sequence(s) employed as carrier and/or positive control compounds substantially contain a primary nucleotide sequence that is not ordinarily found within the genome of a mammal, or within the genome of an organism that is pathogenic to such a mammal. Exemplary mammals include, without limitation, bovines, ovines, porcines, lupines, canines, equines, felines, ursines, murines, leonines, leporines, hircines, and non-human primates.

Preferably, this non-mammalian, non-pathogen-specific carrier/reporter sequence is not cross-reactive, i.e., does not substantially, or preferably, do(es) not, hybridize to, mammalian or pathogen-specific sequences, and as such, non-coding, non-degenerate (i.e., nonsense) sequences are particularly preferred in the formulation of control/carrier sequences to minimize hybridization of the control/carrier sequence to a member of the isolated population of polynucleotides obtained from the collected specimen. Exemplary carrier/control sequences therefore, do not substantially, or preferably, do(es) not, bind (e.g., hybridize under stringent hybridization conditions) to a population of polynucleotides isolated from a mammalian genome, or to a population of polynucleotides isolated from the genome of a bacterium, fungus, virus that is pathogenic to a mammal. Exemplary stringent hybridization conditions known to those of ordinary skill in the art include, without limitation, (a) pre-washing in a solution containing about 5×SSC, 0.5% SDS, and 1.0 mM EDTA (pH 8.0); (b) hybridizing at a temperature of from about 60° C. to about 70° C. in 5×SSC overnight; and (c) subsequently washing at about 65 to about 70° C. for 20 min. with each of 2×, 0.5× and 0.2×SSC containing 0.1% SDS), or equivalent hybridization conditions thereto.

While any practical length of carrier molecule may be utilized in the compositions of the invention, and in particular, in the formulations (e.g., PSS formulations) disclosed herein, preferably, the length of the carrier molecule is about 40 to about 900 nucleotides in length; more preferably, about 50 to about 800, or alternatively about 60 to about 700, nucleotides in length; still more preferably, about 70 to about 600, or alternatively, about 80 to about 500 nucleotides in length; and even more preferably still, about 90 to about 400 nucleotides, or alternatively, about 100 to about 300 or so nucleotides in length.

As such, all intermediate lengths of polynucleotides are contemplated to fall within the scope of the present disclosure, including, without limitation, carrier molecule sequences that are about 45 nucleotides in length, about 50 nucleotides in length, about 55 nucleotides in length, about 60 nucleotides in length, about 65 nucleotides in length, about 70 nucleotides in length, about 75 nucleotides in length, about 80 nucleotides in length, about 85 nucleotides in length, about 90 nucleotides in length, about 95 nucleotides in length, about 100 nucleotides in length, about 120 nucleotides in length, about 140 nucleotides in length, about 160 nucleotides in length, about 180 nucleotides in length, about 200 nucleotides in length, about 220 nucleotides in length, about 240 nucleotides in length, about 260 nucleotides in length, about 280 nucleotides in length, or even about 300 nucleotides or so in length.

While any practical, nonsense/minimally cross-hybridizing polynucleotide sequence is contemplated to be useful in the preparation of a carrier sequence to facilitate improved isolation of the target population of polynucleotides, in circumstances where a control sequence is desired, additional requirements of the primary nucleic acid sequence of the molecule are imposed, namely that the sequence must be detectable and/or quantifiable using one or more conventional molecular biology techniques.

To that end, the invention provides carrier/reporter molecules that contain at least a first sequence domain that specifically hybridizes (i.e., binds) to a suitably-detectable probe, including, without limitation, molecularly-labeled probes and derivatives thereof. Exemplary labeled probes are those that include radioactive, luminescent, chemiluminescent, fluorescent, enzymatic, magnetic, or spin-resonance labels known to those of ordinary skill in the molecular arts. In illustrative embodiments, the labeled probe contains at least a first minor groove binder.

In certain embodiments, to facilitate the binding of conventional detectable-label probes, the carrier/reporter molecules of the invention will contain at least a first sequence domain of from about 10 to about 60 nucleotides in length that specifically binds to at least a first detectable probe.

While the first sequence domain may be of any practical length within the entirety of the carrier sequence, preferably, the first sequence domain will be from about 12 to about 50 nucleotides in length; more preferably, from about 14 to about 45 nucleotides in length; still more preferably, from about 16 to about 40 or so nucleotides in length, and more preferably still, from about 18 to about 30 or so nucleotides in length.

As such, all intermediate lengths of probe-hybridizing sequence domains are contemplated to fall within the scope of the present disclosure, including, without limitation, probe-binding domains that are about 13 nucleotides in length, about 14 nucleotides in length, about 15 nucleotides in length, about 16 nucleotides in length, about 17 nucleotides in length, about 18 nucleotides in length, about 19 nucleotides in length, about 20 nucleotides in length, about 21 nucleotides in length, about 22 nucleotides in length, about 23 nucleotides in length, about 24 nucleotides in length, about 25 nucleotides in length, about 26 nucleotides in length, about 27 nucleotides in length, about 28, or even about 29 or 30 or so nucleotides in length.

Where it is desirable that the carrier/reporter sequence be detectable by one or more amplification-based methodologies (including, without limitation, PCR-based methodologies), additional molecular characteristics for the carrier/reporter sequence are desirable, namely that the sequence, or at least a portion thereof, be amplifiable using one or more polymerase chain-based assays. For PCR or FRET-based methodologies, for example, it is desirable that the carrier/reporter molecule contains at least a second sequence domain that specifically binds to a forward PCR amplification primer (typically of from about 20 to about 40 nucleotides in length) and a third sequence domain that specifically binds to a reverse PCR amplification primer of (also typically of from about 20 to about 40 nucleotides in length). Preferably, the second and third sequence domains are operably positioned to facilitate a PCR-directed amplification of at least a first portion of the nucleic acid segment from the forward and reverse primers under conditions effective to amplify at least a first portion.

When it is desirable that the carrier/reporter sequence be detectable by one or more non-symmetric amplification-based methodologies (including, without limitation, asymmetric PCR, molecular hybridization, affinity-label-based methodologies, and the like), it is not essential that a pair of forward and reverse primer binding domains are required—only a single second sequence domain may be sufficient to detect that carrier sequence using appropriate diagnostic assays. In such embodiments, a single detection/replication primer (or polymerase-binding domain) may be employed. Typically, such sequence domains will be from about 15 to about 35 or so nucleotides in length, although any conventional targeting domain may be employed using conventional analytical methods. The design and primary sequence of such domains is considered routine in the molecular arts, and as such, is within the purview of the ordinarily-skilled artisan.

Depending upon the length and primary nucleotide of the IPC sequence, in certain embodiments, the first sequence domain shares at least a first common nucleotide sequence region with the second, third, or even both the second and third sequence domains. The overlap of such sequences may be only one or more nucleotides, or alternatively, larger regions of overlap consisting of 5 to 10 or more nucleotides.

In exemplary embodiments, the IPC sequence may be prepared by one or more suitable molecular biology techniques, including, e.g., by the in vitro transcription of a polynucleotide that comprises the sequence of the control, or alternatively, comprises a nucleic acid sequence that is complementary to the sequence of the control itself. As described in the following examples, one method of preparing the control sequence involves the preparation of a DNA duplex, from which a single-stranded RNA control sequence may be synthesized.

Exemplary single-stranded RNA control sequences include, but are not limited to, those that contain at least about 105, at least about 95, at least about 85, at least about 75, at least about 65, at least about 55, at least about 45, at least about 35, or at least about 25 or so contiguous nucleotides from the RNA sequence: 5'-CCCUUAGCAGCACGU-CAGUCAGGGAGCCAAUUUCAGAGCUCAGCGAGA-CAGUUUUAUAGGCAUGGCAUCAGCUACGCUCGCU-CAGGCUAGUCAGGUCCAAAGUUUCAGUU-3' (SEQ ID NO:2). In illustrative embodiments, the isolated single-stranded ribonucleic acid molecule is preparable by a process that includes the in vitro transcription of a polynucleotide that comprises, consists essentially of, or alternatively, consists of, the nucleic acid sequence of SEQ ID NO:2.

In one such embodiment, the single-stranded RNA control sequence may be synthesized in vitro from a DNA sequence that contains at least about 90, at least about 80, at least about 70, at least about 60, at least about 50, at least about 40, at least about 30, or at least about 20 or fewer contiguous nucleotides from the sequence: 5'-CCCUUAGCAGCACGUCAGU-CAGGGAGCCAAUUUCAGAGCUCAGCGAGACAGU-UUUAUAGGCAUGGCAUCAGCUACGCUCGCUCAGG-CUAGUCAGGUCCAAAGUUUCAGUU-3' (SEQ ID NO:1). In exemplary embodiments, the isolated single-stranded ribonucleic acid molecule is preparable by a process that includes the in vitro transcription of a polynucleotide that comprises, consists essentially of, or alternatively, consists of the nucleic acid sequence of SEQ ID NO:1.

In one aspect of the invention, there is provided a method for detecting the presence or absence of the RNA carrier molecule within a plurality of polynucleotides obtained from a biological sample prepared using a disclosed sample collection/storage formulation, including, without limitation, one or more formulations as described herein, including, without limitation, PSS formulations. There is also a method for quantitating the amount of RNA carrier molecule within the sample and monitoring the efficacy of the formulations at stabilizing and protecting the molecular fidelity of the isolated polynucleotides. By comparing the amount of carrier molecule remaining in the sample after an elapsed period of time to that of the known quantity of carrier molecule present in the initial solution, one may determine the amount of degradation the carrier molecule has undergone while in the presence of the biological sample. One may use this correlation as an estimation of the extent of degradation that has taken place over time in the population of polynucleotides liberated from the original sample.

In another aspect, the present invention provides a method for rapidly detecting in a biological sample, a particular polynucleotide sequence, such as that of the IPC sequence. In an overall and general sense, this method comprises amplification of a population of nucleotides suspected of containing the particular sequence using conventional methods such as PCR and forward and reverse primers that are specific for the target sequence, hybridization of a specific probe set with the resulting single-stranded PCR product, performing melting curve analysis and analyzing the $T_m$ change of the hybrid of the single-stranded PCR product with the hybridization probes.

In one embodiment, the present invention provides a method for rapidly detecting the presence of a polynucleotide (such as a carrier IPC sequence), using a PCR-based methodology, which generally comprises the steps of: (a) isolating polynucleotides from the sample to be analyzed; (b) amplifying the polynucleotides by PCR using a primer set that is specific to the target sequence; (c) hybridizing one or more labeled probes that are specific for the polynucleotide of interest with the single-stranded PCR product obtained from step (b); and (d) detecting the presence of the labeled probe in the sample, indicative of the presence of the specific target sequence within the population of isolated polynucleotides.

One such method for the detection of polynucleotides using a labeled "probe" sequence utilizes the process of fluorescence resonance energy transfer (FRET). Exemplary FRET detection methodologies often involve pairs of fluorophores comprising a donor fluorophore and acceptor fluorophore, wherein the donor fluorophore is capable of transferring resonance energy to the acceptor fluorophore. In exemplary FRET assays, the absorption spectrum of the donor fluorophore does not substantially overlap the absorption spectrum of the acceptor fluorophore. As used herein, "a donor oligonucleotide probe" refers to an oligonucleotide that is labeled with a donor fluorophore of a fluorescent resonance energy transfer pair. As used herein, "an acceptor oligonucleotide probe" refers to an oligonucleotide that is labeled with an acceptor fluorophore of a fluorescent resonance energy transfer pair. As used herein, a "FRET oligonucleotide pair" will typically comprise an "anchor" or "donor" oligonucleotide probe and an "acceptor" or "sensor" oligonucleotide probe, and such pair forms a FRET relationship when the donor oligonucleotide probe and the acceptor oligonucleotide probe are both hybridized to their complementary target nucleic acid sequences. Acceptable fluorophore pairs for use as fluorescent resonance energy transfer pairs are well known to those skilled in the art and include, but are not limited to, fluorescein/rhodamine, phycoerythrin/

Cy7, fluorescein/Cy5, fluorescein/Cy5.5, fluorescein/LC Red 640, and fluorescein/LC Red 705, and the like.

Primers useful in amplification of a particular IPC sequence may be designed using, for example, a computer program such as OLIGO® (Molecular Biology Insights Inc., Cascade, Colo., USA). Typically, oligonucleotide primers are from about 10 to about 60 or so nucleotides in length (including, without limitation, all intermediate integers, e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or even 60 or more nucleotides in length), although primers of any practical length may be useful in the practice of the invention.

The invention also provides a method for increasing the efficiency of obtaining a purified population of polynucleotides from a biological sample suspected of containing such polynucleotides. In an overall and general sense, the method includes contacting the sample with a composition that comprises one or more of the formulations described herein (including, without limitation, PSS formulations), and a carrier and/or IPC nucleic acid segment, in an amount and for a time sufficient to increase the efficiency of obtaining the purified population of polynucleotides from the biological sample.

In exemplary embodiments, the integrity of a population of polynucleotides in the biological sample, and/or the fidelity of at least a first sequence of at least one of the polynucleotides obtained from the sample is at least substantially maintained (i.e., at least 75% of the nucleotides within the population are substantially full-length) when the composition comprising the sample is stored at a temperature of from about −20° C. to about 40° C. for a period of from about 7 to about 14 days or longer; alternatively at a temperature of from about −20° C. to about 40° C. for a period of from about 7 to about 14 days or longer; or alternatively at a temperature of from about 20° C. to about 40° C. for a period of from about 14 to about 30 days or more.

Alternatively, the integrity of a population of polynucleotides in the biological sample is at least substantially maintained such that at least about 80%, at least about 85%, at least about 90%, or at least about 95% or more of the nucleotides within the population are present in the solution when compared to the amount present in the solution when the sample was initially collected. In preferred embodiments, the integrity of the sample will be substantially maintained such that all, or almost all of the polynucleotides present in the initial sample will be maintained (i.e., not detectably degraded) over time.

In the practice of the disclosed methods, preferably from the time of collection to the time of isolating, purifying, or characterizing a population of polynucleotides therein, less than about 20% of the population of polynucleotides originally present in the collected sample will be degraded over time during subsequent storage. Preferably, substantially less than about 15% of the population of polynucleotides originally present in the collected sample will be degraded over time during subsequent storage, more preferably, less than about 10% of the population of polynucleotides originally present in the collected sample will be degraded over time during subsequent storage, and more preferably still, less than about 5% of the population of polynucleotides originally present in the collected sample will be degraded over time during subsequent storage. In particularly preferred embodiments, not more than about 5%, about 4%, about 3%, about 2% or about 1% of the population of polynucleotides originally present in the collected sample will be degraded over time during subsequent storage. Such high-integrity preservation of sample quality is preferable, regardless of the conditions under which the sample is stored, and will be substantially maintained for a period of time of at least about 7 days, at least about 14 days, at least about 21 days, at least about 30 days, at least about 45 days, at least about 60 days, or even at least about 90 days or more.

The disclosed methods for collecting, storing, and/or transporting samples of biological origin from which one or more populations of nucleic acids may be obtained, may also further optionally include one or more steps, including without limitation, (a) analyzing and/or quantitating one or more polynucleotides obtained from the sample; (b) detecting the presence of the carrier molecule (i.e., IPC) in the collected sample; (c) quantitating the amount of the IPC in the collected sample; and/or (d) measuring the sequence fidelity of, or determining the percent degradation of the IPC in the collected sample.

While the presence of, integrity of, or sequence fidelity of, a particular polynucleotide sequence obtained from, or utilized in the practice of the present invention may be determined, using any conventional methodology known to those of ordinary skill in the molecular arts, in one embodiment, PCR amplification is utilized. Likewise, determination of the integrity of a polynucleotide of interest may include determination of the PCR cycle threshold ($C_T$) under given conditions, and determination of the sequence fidelity, qualitative integrity of collected nucleic acids may be determined by conventional DNA or RNA sequencing methods, including, without limitation, the chemical-based methods of Maxam-Gilbert, the dideoxy chain termination method of Sanger et al., the dye fluorophore-based method of Mathies et al., or pyrosequencing techniques as described by Nyren and Ronaghi.

Exemplary formulations of the invention include a one-step collection solution that lyses, stabilizes, and preserves the integrity of nucleic acids prepared from a biological sample for subsequent RNA and/or DNA isolation, detection, quantitation, amplification, and/or analysis.

In certain embodiments, the nonsense, carrier/IPC compositions of the invention will be formulated in a one-step sample collection/storage/transport medium that includes: a) one or more chaotropes (each preferably present in the composition an amount from about 0.5 M to about 6 M); b) one or more detergents (each preferably present in the composition an amount from about 0.1% to about 1%); c) one or more chelators (each preferably present in the composition in an amount from about 0.01 mM to about 1 mM); d) one or more reducing agents (each preferably present in the composition in an amount from about 0.05 M to about 0.3 M); and e) one or more defoaming agents (each preferably present in the composition in an amount from about 0.0001% to about 0.3%).

Exemplary chaotropes include, without limitation, guanidine thiocyanate (GuSCN), guanidine hydrochloride (Gu-HCl), guanidine isothionate, potassium thiocyanate (KSCN), sodium iodide, sodium perchlorate, urea, or any combination thereof. Descriptions of additional exemplary chaotropes and chaotropic salts can be found in U.S. Pat. No. 5,234,809 (specifically incorporated herein in its entirety by express reference thereto).

Exemplary detergents include, without limitation, sodium dodecyl sulfate (SDS), lithium dodecyl sulfate (LDS), sodium taurodeoxycholate (NaTDC), sodium taurocholate (NaTC), sodium glycocholate (NaGC), sodium deoxycholate (NaDC), sodium cholate, sodium alkylbenzene sulfonate (NaABS), N-lauroyl sarcosine (NLS), salts of carboxylic acids (i.e., soaps), salts of sulfonic acids, salts of sulfuric acid, phosphoric and polyphosphoric acid esters, alkylphosphates, monoalkyl phosphate (MAP), and salts of perfluorocarboxylic acids, anionic detergents including those described in U.S. Pat. No. 5,691,299 (specifically incorporated herein in its entirety by express reference thereto), or any combination thereof.

Exemplary reducing agents include, without limitation, 2-mercaptoethanol (β-ME), tris(2-carboxyethyl) phosphine (TCEP), dithiothreitol (DTT), formamide, dimethylsulfoxide (DMSO), or any combination thereof. In a preferred embodiment, the reducing agent includes or is TCEP.

Exemplary chelators include, without limitation, ethylene glycol tetraacetic acid (EGTA), hydroxyethylethylenediaminetriacetic acid (HEDTA), diethylene triamine pentaacetic acid (DTPA), N,N-bis(carboxymethyl)glycine (NTA), ethylenediaminetetraacetic (EDTA), citrate anhydrous, sodium citrate, calcium citrate, ammonium citrate, ammonium bicitrate, citric acid, diammonium citrate, potassium citrate, magnesium citrate, ferric ammonium citrate, lithium citrate, or any combination thereof. In preferred embodiments, the chelator includes EDTA, a citrate, or a combination thereof. In a more preferred embodiment, the chelator includes EDT.

The compositions of the invention can further include a defoaming agent to prevent the formation of bubbles that typically result from the presence of detergents in the formulation. Defoaming agents facilitate pipetting and handling of the disclosed compositions. Exemplary surfactants/defoaming agents include, without limitation, cocoamidopropyl hydroxysultaine, alkylaminopropionic acids, imidazoline carboxylates, betaines, sulfobetaines, sultaines, alkylphenol ethoxylates, alcohol ethoxylates, polyoxyethylenated polyoxypropylene glycols, polyoxyethylenated mercaptans, long-chain carboxylic acid esters, alkonolamides, tertiary acetylenic glycols, polyoxyethylenated silicones, N-alkylpyrrolidones, alkylpolyglycosidases, silicone polymers such as Antifoam A®, or polysorbates such as Tween®, or any combination thereof. In a preferred embodiment, a defoaming agent includes a silicone polymer.

Optionally, the compositions of the invention may further include one or more buffers (each preferably present in the final composition in an amount from about 1 mM to about 1 M). Exemplary buffers include, without limitation, tris(hydroxymethyl)aminomethane (Tris), citrate, 2-(N-morpholino)ethanesulfonic acid (MES), N,N-bis(2-hydroxyethyl)-2-aminoethanesulfonic acid (BES), 1,3-bis(tris(hydroxymethyl)methylamino)propane (Bis-Tris), 3-(cyclohexylamino)-1-propanesuhinic acid (CAPS),3-(cyclohexylamino)-2-hydroxy-1-propanesuhicic acid (CAPSO), 4-(2-hydroxyethyl)-1-piperazineethanesulfonic acid (HEPES),3-(N-morpholino)propanesulfonic acid (MOPS), 3-(N-morpholino)-2-hydroxypropanesulfonic acid (MOPSO), piperazine-N,N\'-bis(2-hydroxypropanesulfonic acid (POPSO), N-[Tris(hydroxymethyl)methyl]-3-amino propanesulfonic acid (TAPS), N-[Tris(hydroxymethyl)methyl]-3-amino-2-hyidroxypropansulfonic acid (TAPSO), N-[Tris(hydroxymethyl)methyl]-2-aminoethanesulfonic acid (TES), N,N-bis(2-hydroxyethyl)glycine (Bicine), N-[tris(hydroxymethyl)methyl]glycine (Tricine), N-2-acetamido-2-iminodiacetic acid (ADA), N-(2-acetamido)-2-aminoethanesulfonic acid (ACES), piperazine-1,4-bis(2-ethanesulfonic acid) (PIPES), bicarbonate, phosphate, or any combination thereof. In a preferred embodiment, the buffer includes a citrate.

The inclusion of one or more of such optional but preferred buffers is desirable to control the pH of the formulations, since it has been found that nucleic acid extraction is optimal in a pH range of about 5 to 7. Preferably, the one or more buffers employed in the disclosed compositions are chosen to provide a significant buffering capacity in the range from a pH of about 6 to a pH of about 8, more preferably within a pH range of about 6 to about 7, and more preferably still, within a pH range of about 6.2 to about 6.8. In exemplary embodiments, the pH of a PrimeStore™ solution (also referred to herein as "PSS") is preferably about 6.9±0.25.

The compositions of the invention may also further optionally include one or more short-chain (preferably from 1- to 6-carbon [i.e., $C_1$-$C_6$] alcohols) alkanols (each preferably present in the composition in an amount from about 1% to about 25%, although higher percentages of the alcohols may be employed if desired). Exemplary short-chain alkanols include linear and branched-chain alcohols, such as, without limitation, methanol, ethanol, propanol, butanol, pentanol, hexanol, or any combination thereof.

The compositions of the invention may also further optionally include one or more additional compounds or reagents including, without limitation, cationic functionalized zwitterionic compounds such as betaines (including, without limitation, N,N,N-trimethylglycine, cocamidopropyl betaine, and the like), albuminoids (including, without limitation, ovalbumin, and the serum albumins of bovine, equine, or human origin), and osmolytes (including, without limitation, trimethylamine N-oxide (TMAO), dimethylsulfoniopropionate, sarcosine, and saccharides or sugar alcohols including, without limitation, trehalose, maltose, rhamnose, sucrose, arabinose, fucose, mannitol, sorbitol, adonitol, and the like).

Preferably, the compositions of the invention provide sufficient buffering capacity to adequately stabilize the populations of polynucleotides obtained from a sample, and will, most preferably, be buffered to a pH of about 6.4 to 6.9 during formulation, and will maintain the isolated populations of polynucleotides in a similar pH range when the sample is contacted with the storage/collection formulations described herein.

The compositions of the present invention will typically at least substantially inactivate, and preferably entirely inactivate, any endogenous or exogenous RNAses or DNAses present in the sample, such that the nucleic acids of the sample are substantially free of any degradation, and preferably do not degrade, or lose integrity, during the collection, lysis, storage, and transport of the sample for subsequent in vitro or in vivo analyses.

Exemplary formulations of the storage/transport/collection compositions of the invention are described in the examples herein, and include, without limitation, a composition that includes about 4 M of a chaotrope (such as guanidine thiocyanate, guanidine hydrochloride, guanidine isocyanate, or any combination thereof), about 10 mM to 30 mM of a chelator (such as EGTA, HEDTA, DTPA, NTA, EDTA, citrate anhydrous, sodium citrate, calcium citrate, ammonium citrate, ammonium bicitrate, citric acid, diammonium citrate, ferric ammonium citrate, lithium citrate, or any combination thereof), about 0.25% of a detergent (such as SDS, LDS, NaTDC, NaTC, NaGC, NaDC, sodium cholate, NaABS, NLS, or any salt or combination thereof), about 0.1 M of a reducing agent (such as β-ME, DTT, DMSO, formamide, TCEP, or any combination thereof), and about 0.1% of a surfactant/defoaming agent (such as a silicone polymer [e.g., Antifoam A®] or a polysorbate [e.g., Tween®], or any combination thereof).

Additional exemplary formulations of the specimen collection compositions of the invention include, without limitation, a composition that includes about 3 M of a chaotrope (such as guanidine thiocyanate, guanidine hydrochloride, guanidine isocyanate, or any combination thereof), about 1 mM of 0.5 M reducing agent (such as, e.g., β-ME, TCEP, formamide, DTT, DMSO, or any combination thereof), about 1 to about 10 mM of a chelator (such as, e.g., EGTA, HEDTA, DTPA, NTA, EDTA, citrate anhydrous, sodium citrate, calcium citrate, ammonium citrate, ammonium bicitrate, citric acid, diammonium citrate, ferric ammonium citrate, lithium citrate, or any combination thereof), about 0.25% of a detergent (such as SDS, LDS, NaTDC, NaTC, NaGC, NaDC, sodium cholate, NaABS, NLS, or any salt or combination thereof), and optionally but preferably about 0.0002% of a defoaming agent (also referred to as an antifoaming agent) (such as a silicone polymer or a polysorbate, or any combination thereof) and about 100 mM of a buffer (such as Tris, MES, BES, Bis-Tris, HEPES, MOPS, bicarbonate, citrate, phosphate, or any combination thereof).

Another exemplary formulation of the disclosed polynucleotide isolation and stabilization compositions include, without limitation, a composition that includes about 1 to about 4 M of a chaotropic agent such as guanidine thiocyanate, guanidine hydrochloride, or guanidine isocyanate; about 0.5 to 100 mM of a chelating agent such as EDTA, or sodium citrate, or both; about 0.1 to about 1% of an anionic detergent such as SDS or N-lauroyl sarcosine, sodium salt; about 0.001 to about 0.0001% of a surfactant or wetting agent such as the silicone polymer, Antifoam A®, e); about 10 to about 500 mM of a buffering agent such as Tris-HCl; and about 10 to about 25% of a short-chain alkanol such as ethanol.

In particular embodiments, the invention provides a composition that includes about 2.5 M guanidine thiocyanate; about 0.5 mM TCEP; about 10 mM sodium citrate; about 0.4% N-lauroyl sarcosine, sodium salt; about 0.0002% Antifoam A, about 100 mM Tris-HCl, about 0.1 mM EDTA; and about 23% ethanol.

The invention also provides a method for obtaining a population of polynucleotides from a sample suspected of containing nucleic acids. The method generally involves associating the sample with an amount of one of the disclosed compositions, under conditions effective to obtain a population of polynucleotides from the sample. The invention does not require separation of the population to "obtain" the sample, as later diagnosis may or may not need such separation.

The invention also provides a method of preparing a one-step aqueous formulation of the collection/lysis/transport/storage compositions described herein for the collection of nucleic acids such as RNA and/or DNA. In an overall sense, the method generally involves combining one or more chaotropes and nuclease-free water at a temperature of about 20° C. to 90° C. in a reaction zone; then combining the dissolved one or more chaotropes with one or more reducing agents, one or more chelators, and one or more detergents in the reaction zone to form an intermediate composition; optionally combining a silicone polymer with the intermediate composition in an amount sufficient to minimize foaming during further preparation of the one-step aqueous formulation; combining a sufficient amount of buffer to the intermediate composition to maintain a pH of about 6 to 6.9; optionally combining a second chelating agent to the reaction zone; then increasing the temperature of the second intermediate composition to about 60 to 95° C. for about 1 to 30 minutes and lowering the temperature to ambient conditions; optionally then combining a $C_{1-6}$ alcohol with the contents of the reaction zone; and optionally adjusting the pH to be about 6.4 to 6.9.

In additional embodiments, the invention provides a method for preparing one-step aqueous formulations adapted to obtain a population of polynucleotides from a biological sample or specimen that is suspected of containing nucleic acids. This method generally involves at least the steps of: a) contacting the sample with an amount of the one-step aqueous formulation effective to:

i) at least substantially kill or inactivate potentially-infectious pathogens in the sample;

ii) at least lyse a portion of cells to release RNAs and/or DNAs from the sample; and iii) at least substantially inhibit or prevent the released polynucleotides in the sample from further hydrolysis or enzymatic degradation, modification, or inactivation, so as to obtain the population of polynucleotides from the sample.

Preferably, the methods of the invention will include at least contacting the sample with an amount of one or more of the disclosed compositions at a temperature of from 0° C. to about 40° C. (more preferably at a temperature of 4° C. to about 35° C., and still more preferably at a temperature of 10° C. to about 30° C.) for a period of time of at least 24 hrs, more preferably, for a period of time of at least 48 hrs, at least 72 hrs, at least 96 hrs, or longer, without causing substantial deterioration, degradation, enzymatic cleavage, and/or nucleolytic digestion, modification, or processing of the nucleic acids contained within a sample contacted with such a composition.

In certain embodiments, the methods of the invention will include at least contacting the sample with an amount of one or more of the disclosed compositions at a temperature from about 0° C. to about 40° C. (more preferably at a temperature from about 4° C. to about 35° C., still more preferably at a temperature from about 10° C. to about 30° C., and more preferably still at a temperature from about 15° C. to about 25° C.) for a period of time of at least 7 days, more preferably, for a period of time of at least 14 days; at least 21 days, at least 28 days, or even longer without causing significant deterioration, degradation, enzymatic cleavage, and/or nucleolytic processing of the nucleic acids contained within a sample so processed. It should be understood that associating a sample with an inventive composition need only occur for a short time, but to avoid the need for immediate separation of the nucleic acids from the sample and the one-step composition of the invention all the materials may remain in contact for the time periods specified above without any substantial, or without any, degradation of the nucleic acids.

Preferably, the integrity of a population of polynucleotides released from the sample into the composition will be substantially maintained, even when the composition comprising the sample is stored at ambient temperatures, and even for prolonged periods of time, including, without limitation, storage for greater than about 10 days, greater than about 20 days, or even greater than about 30 days or more. Likewise, it is desirable that the integrity of a population of polynucleotides released from the sample into the composition will be substantially maintained, even when the composition comprising the sample is stored at subtropical and tropical temperatures—even for prolonged periods of time, including, without limitation, storage for greater than or equal to about 5 days, greater than or equal to about 10 days, greater than or equal to about 15 days, or even greater than or equal to about 20, about 25, about 30, about 35, about 40, about 60, or about 90 days or even greater.

In the practice of the present methods, it is preferable that at least one or more biological cells contained within the sample are substantially lysed to release at least a first population or first plurality of polynucleotides contained within such cells into the composition. Preferably, the components of the disclosed composition are sufficient to release such a population from all or substantially all of the remaining cellular/tissue and/or sample debris (including, without limitation, lipids, phospholipids, peptides, proteins, polysaccharides, lipopolysaccharides, polyols, cellular organelles, membrane components, and such like).

It is also desirable in the practice of the present methods that at least one or more exogenous or endogenous nucleases that may be present in, on, or about the sample itself, will be sufficiently inactivated by one or more components of the composition such that the resulting nucleic acids are not destroyed, damaged, or nucleolytically cleaved when the biological cells contained within the sample are substantially lysed to release the population of polynucleotides from the cells. Preferably, one or more components of the disclosed composition are effective to kill, inactivate, or substantially inhibit the biological activity of a DNAse or an RNAse, when such a protein is present in the sample.

It is also desirable in the practice of the present methods that when one or more microbes, viruses, fungi, and/or other pathogens or organisms of interest are present in, on, or about the sample when collected, such microbes, viruses, fungi, and/or other pathogens or organisms of interest will be lysed, sufficiently inactivated, or substantially killed upon contact with the composition, which facilitates safe handling of the sample by the practitioner. Preferably, one or more components of the disclosed composition are effective to render a pathogenic sample substantially or preferably entirely, non-pathogenic without the need for adding additional components to the composition. However, in certain applications, it may also be desirable to include one or more additional anti-microbial, anti-viral, or anti-fungal agents to the compositions to render them substantially non-pathogenic, and thus, safe for handling by the practitioner.

Preferably, the composition containing the sample is at least sufficiently stable to permit storage of the sample in the composition at ambient, near-ambient, or even colder or warmer conditions at least substantially (or entirely) from the time of specimen or sample collection substantially until the time of analyzing or characterizing at least a first population of polynucleotides from within the sample. As used herein, "ambient temperature" can refer to temperatures of about 18° C. to 25° C., or in some embodiments, more preferably from about 20° C. to about 22° C.

In certain embodiments, the composition containing the sample may be stored at a temperature of about 0° C. to about 40° C., more preferably at a temperature of about 4° C. to about 30° C., more preferably, at a temperature of about 10° C. to about 25° C., at least substantially from the time of collection to the time that the polynucleotides obtained from the sample are further isolated, purified, or characterized using one or more conventional molecular biology methodologies.

In certain embodiments, the composition containing the sample suspected of containing nucleic acids will stabilize the nucleic acids to the extent that they either remain at least substantially non-degraded (i.e., at least substantially stable) even upon prolonged storage of the composition at ambient, refrigerator, or sub-zero temperatures. It will be desirable that this stability provides that at least about 70%, at least about 85%, more preferably at least about 90%, more preferably at least about 95%, or even more preferably, at least about 98% of the polynucleotides contained within the stored sample will not be degraded upon prolonged storage of the sample. In certain embodiments, substantially all of the polynucleotides contained within the sample will be stabilized such that the original integrity of the polynucleotides is preserved during the collection, lysis, storage, and transport of the processed sample.

In certain embodiments, the method will preferably provide a population of nucleic acids prepared from a biological sample in which less than about 15% of the polynucleotides contained in the sample will be degraded during the collection, lysis, storage, and transport of the sample after it has been stored in the composition at a temperature of from −20° C. to about 40° C. for a period of at least 24, 48, 72, or 96 hrs or longer after the sample was initially introduced into the composition.

In related embodiments, the method will preferably provide a population of nucleic acids prepared from a biological sample in which less than about 10% of the polynucleotides contained in the sample will be degraded during the collection, lysis, storage, and transport of the sample after it has been stored in the composition at a temperature of from −20° C. to about 40° C. for a period of at least 24, 48, 72, or 96 hrs or longer after the sample was initially introduced into the composition.

Likewise, in some applications of the methodology disclosed herein, use of the disclosed compositions will preferably provide a population of nucleic acids that are prepared from a biological sample, wherein less than about 5% of the polynucleotides contained in the sample will be degraded during the collection, lysis, storage, and transport of the sample after it has been stored in the composition at a temperature from −20° C. to about 40° C. for a period of at least 24, 48, 72, or 96 hrs or longer after the sample was initially introduced into the composition.

In some instances, the population of nucleic acids prepared by the present methods may be maintained with sufficient integrity such that no more than about 1 or 2% of the sample will be degraded even when the composition is stored at a temperature from 0° C. to about 40° C. for periods of several days to several weeks. In fact, the inventors have shown that samples of nucleic acids isolated using the disclosed methods remain at least substantially stable, preferably stable, in their non-degraded form for periods of several weeks to even several months or more, even when the composition containing the nucleic acids is stored at a temperature from 10° C. to about 40° C. In one preferred embodiment, the upper limit on the above-noted temperature ranges is about 37° C. Thus, the term "stable" as used herein may refer to the various embodiments noted above regarding the integrity of the population of nucleic acids after a particular time lapse at a given temperature.

The polynucleotides of the present invention, and particularly those useful in the preparation of IPCs, preferably contain at least a first polymerase transcription region operably linked to a positive control sequence (PCS). Such regions may be operatively positioned upstream of the PCS, such that the PCS is amplified when a suitable polymerase (e.g., T3, SP6, or T7 polymerase, and the like) is contacted with the PCS under suitable reaction conditions. The construct may further comprise a single primer, or alternatively, two or more primers (e.g., "forward" and "reverse" primers) may be used to facilitate expression of the PCS. Exemplary primers useful in the practice of the invention include, but are in no way limited to, those primer sequences that specifically bind to the PCS itself or to regions immediately upstream (5') and or downstream (3') of the PCS. In illustrative embodiments, the PCS will contain at least a first region to which a first detection probe (including, without limitation, luminescent, fluorescent, chemiluminescent, or FRET probes as described herein) specifically binds.

The polynucleotides useful in the preparation of IPCs may also further optionally comprise one or more native, synthetic, homologous, heterologous, or hybrid promoter(s), enhancer(s), regulatory element(s), linker(s), spacer(s), binding domain(s), or transcription activation site(s), etc.

In illustrative embodiments, the inventors have demonstrated that the disclosed sample collection/transport media may successfully be employed to permit the collection and storage of biological samples for periods of days, to weeks, to months, even when stored at ambient environmental conditions. As such, the disclosed formulations provide effective compositions for maintaining the fidelity and integrity of populations of isolated nucleic acids for about 1, about 2, about 3, about 4, about 5, about 6, about 7, about 8, about 9, or even about 10 weeks or more without significant deterioration in the quality of the polynucleotides contained within the sample. In fact, long-term storage of the samples is even possible under ambient and near-ambient conditions for periods of several months or more—a significant improvement over any conventional commercial formulations examined by the inventors during the present invention.

Data obtained using in vitro analyses of collected specimens have demonstrated that samples collected and stored in one of the disclosed collection/storage/transport formulations remain substantially non-degraded, and functionally-viable when stored in the solution for a period of a few days to a few weeks to a few months or longer. Comparison of results obtained after about 1, about 2, about 3, about 4, about 5, about 6, about 7, or even about 8 weeks or longer demonstrated the effectiveness of the solutions in preventing substantial nuclease activity against the isolated polynucleotides, and protecting the isolated molecules from contamination or molecular degradation.

Commercial Formulations and Kits

The present invention also provides kits and sample collection systems utilizing the disclosed compositions and collection/storage/transport solutions described herein. In particular embodiments, such sample collection systems may include a collection device, such as a swab, curette, or culture loop; and a collection vessel, such as a vial test tube, or specimen cup, that contains one or more of the compositions disclosed herein. The collection vessel is preferably releasably openable, such that it can be opened to insert the one-step compositions and closed and packaged, opened to insert the sample and optionally a portion of the collection device and closed for storage and transport, or both. The collection vessel may use any suitable releasable or openable mechanism, including without limitation a screw cap, snap top, press-and-turn top, or the like. Such systems may also further optionally include one or more additional reagents, storage devices, transport devices, and/or instructions for obtaining, collecting, lysing, storing, or transporting samples in such systems. In a preferred embodiment, the one-step compositions of the invention may already be disposed in the reaction zone into which the sample may be associated. In such embodiments, the invention requires only a collection device and the collection vessel. The kit may also include one or more isolation or extraction devices to help liberate and/or separate one or more populations or pluralities of nucleic acids contained within the sample from one or more other biomolecules or sample components to obtain at least partially, or substantially purified nucleic acids suitable for identification, detection, or further molecular analysis.

Kits may also be packaged for commercial distribution, and may further optionally include one or more collection, delivery, transportation, or storage devices for sample or specimen collection, handling, or processing. The container(s) for such kits may typically include at least one vial, test tube, flask, bottle, cup, or other suitable container or collection device, into which the composition(s) may be placed, and, preferably, suitably aliquotted for individual specimen collection, transport, and/or storage. The kit may also include a larger container, such as a case, that includes the smaller, individual containers noted above, along with other collection devices, equipment, reagents, instructions, and/or the like. The kit may also optionally include one or more additional buffers, compounds, or compositions, and may also further optionally include one or more instructions detailing use(s) of the kit in either the collection or storage of one or more biological, clinical, diagnostic, environmental, or forensic sample. Optionally, the kit may also further provide instructions for the transport of the sample once placed in one or more of the disclosed compositions, and may even include instructions or additional reagents detailing one or more subsequent analytical methods or assays employing the nucleic acids isolated from the sample or specimen. Such kits may also include multiples of the various collection devices and collection vessels and any other components to be included, so that the kits can be used to collect multiple samples from the same source or different sources. In one commercial application, the kits are packaged in sets of five or more for convenient sale and use.

BRIEF DESCRIPTION OF THE DRAWINGS

For promoting an understanding of the principles of the invention, reference will now be made to the embodiments, or examples, illustrated in the drawings and specific language will be used to describe the same. It will, nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The following drawings form part of the present specification and are included to demonstrate certain aspects of the present invention. The invention may be better understood by reference to the following description taken in conjunction with the accompanying drawings, in which like reference numerals identify like elements, and in which:

FIG. 2 shows the extraction efficiency of PSS (ver. 1) compared to commercial kits. Homogenized cotton rat nose (*) challenged with influenza A (H3N2) or a human clinical influenza A (H1N1) samples collected during the 2006-07 season were lysed in the PSS or lysed using the respective lyses solution, protocol, and extraction procedure from three commercially available kits: RNAqueous-Micro Kit (Ambion), QiaAmp™ Viral Mini Kit (Qiagen), and AI/NCD MaxMag™ (Ambion) Kit. Extraction efficiency was evaluated using the Applied Biosystems ABI7500 platform with the comparative $C_T$ method. The relative $C_T$ scores and viral copies detected were optimal when PSS (depicted as the "one-step formulation") was utilized in place of the respective lysis buffer provided in each standard commercially-available kit;

FIG. 3 shows the preservation of naked RNA in PSS vs. Ambion's RNA Storage Solution. Single-stranded Avian H5 RNA was stored in PSS, RNA storage solution (Ambion), or water at ambient temperature (22-24° C.) for 96 hours. A total of 5 pg of RNA was extracted using the RNAqueous®-Micro Kit (Ambion, Cat#AM1931) according to the manufacturer's recommendations, and subsequently analyzed using qRT-PCR on the Applied Biosystems ABI7500 platform (Life Technologies). Values are given as $C_T$ using the absolute quantification method;

FIG. 4 shows an example of a PSS packaging format for clinical diagnostic collection. Directions of sample collection using a clinical collection swab (Copan Diagnostics) and a 5 mL collection tube containing 1.5 mL of PSS;

FIG. 5 shows an exemplary commercial formulation of the PSS. Three exemplary commercial collection solution formats are depicted: a 25 mL bottle, and the 5 mL and 1.5 mL test tubes;

FIG. 6 illustrates the ability of PSS to rapidly kill microorganisms. Shown is a comparison of cell growth of methicillin-resistant *Staphylococcus aureus* (MRSA) either in culture medium (TSB), or in a solution of PS. After 10 seconds in PSS, no viable bacterial pathogens were detected.

FIG. 7A shows the inactivation of chicken cloacal specimens in PSS (ver. 1). PSS (ver. 1) inactivated microbial agents in 1 hr. Four original chicken cloacal samples were immersed in PSS (ver. 1) (top row) or water (bottom row) and subsequently plated on blood agar plates;

FIG. 7B demonstrates that PSS inhibits RNA base hydrolysis for 30 days at room temperature. RNA was incubated at room temperature (22-26° C.) in PSS (gel lane 1 and 3) and water (gel lane 2 and 4), and subsequently RT-PCR amplified (1500 base pairs) at Day 0 and Day 30. PSS preserved collected RNA, and prevented RNA/DNA degradation at room temperature up to 30 days;

FIG. 8A depicts the qRT-PCR analysis of "naked" influenza A avian H5 RNA template preserved in PSS after incubation in RNA/DNA nucleases. H5 cRNA (2 ng) was incubated with ribonuclease A and T1, and DNAseI for 1 hour @ 37° C. and extracted using the RNAaqueous®-MicroKit (Ambion). Triplicate reactions were included for each reaction condition. qRT-PCR $C_T$ values of naked RNA preserved in PSS with added nucleases (average $C_T$: 22.88) were similar to an equal quantity of template cRNA control (average $C_T$: 23.70). Template cRNA reactions subjected to nuclease digestion without PSS were almost completely degraded (average $C_T$ 39.58);

FIG. 8B depicts the qRT-PCR analysis and gel electrophoresis of "naked" influenza A avian H5 RNA template preserved in PSS after incubation in RNA/DNA nucleases at 37° C. for 7 days. Two nanograms of H5 cRNA was incubated with RNase A, RNAse T1, and DNase I, then extracted using the RNAqueous®-Micro Kit (Ambion) after 7 days. Duplicate reactions were included for each reaction. qRT-PCR $C_T$ values of naked RNA preserved in PSS with added nucleases (average $C_T$: 33.51) were detected after 7 days. Template cRNA reactions subjected to nuclease digestion without PSS were completely degraded, and similar to NTC reactions.

FIG. 8C demonstrates that PSS formulations substantially inhibited digestion of the sample polynucleotides by endogenous nucleases. Gel electrophoresis of post-amplified product. Lane 3 is the PCR product from template RNA+PSS at 37° C. for 7 days, and Lane 5 amplification of positive control RNA. Lane 5 (no amplification) contained RNA without PSS; Lanes 2 and 6 are 100-bp ladder, and NTC reactions, respectively.

FIG. 9 illustrates that the preservation of nucleic acids achieved in PSS is superior to that of other solutions. PSS (ver. 2 and ver. 2.2) Preservation of RNA from influenza A virus compared to Qiagen AVL buffer, ethanol, and viral transport medium (VTM) (Becton-Dickinson, Franklin Lakes, N.J., USA) at ambient temperature (22-25° C.) for 30 days.

FIG. 10 shows the extraction efficiency of Influenza A virus preserved in PSS (ver. 2.2) for 30 days at various temperatures. Environmental (21-37° C.); Freeze-thawed (−25° C.; 32×); ambient temperature (22-26° C.); and Lane 5: refrigerated (4° C.).

FIG. 11 is a graph of $C_T$ vs. molar concentration using whole influenza A virus with TCEP as the reducing agent;

Figure 12:
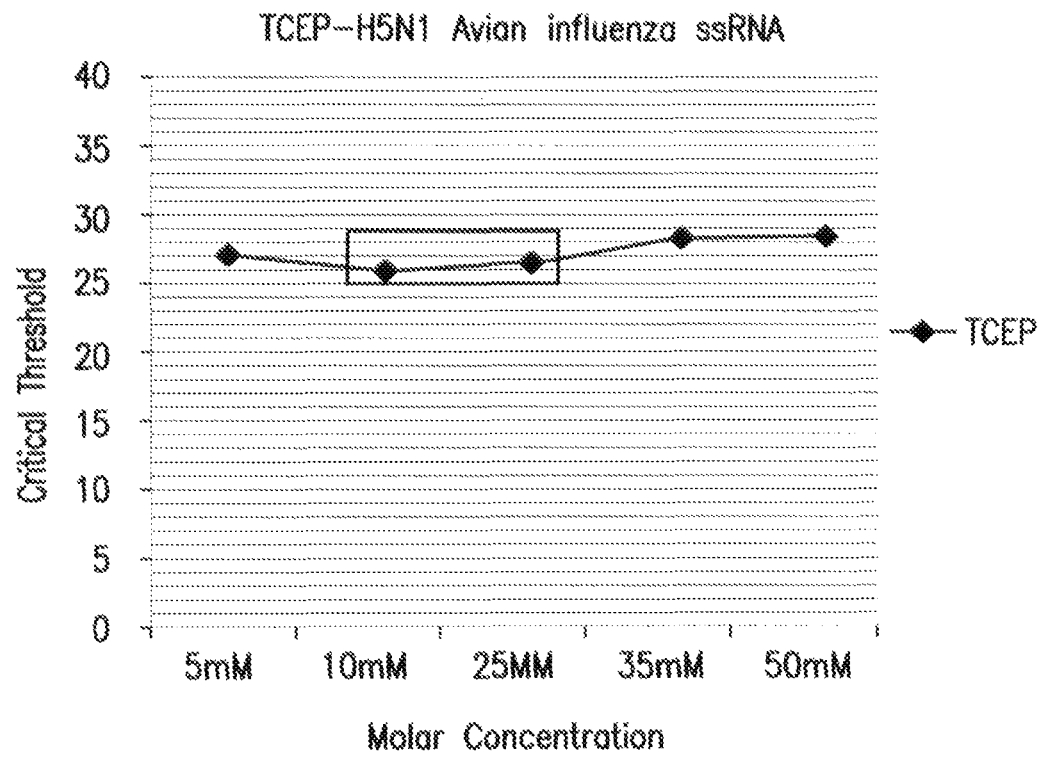

FIG. 12 is a graph of $C_T$ vs. molar concentration using $H_5N_1$ Avian influenza ssRNA with TCEP as the reducing agent;

FIG. 13A and FIG. 13B show the comparison between TCEP and β-ME as reducing agent components in the PSS formulations, with water only serving as a control. In FIG. 13A, H5 avian influenza RNA was employed, while in FIG. 13B, whole virus were used.

FIG. 14A shows the results of a study employing PSS in preserving nucleic acids from blood. PSS extraction efficiency of whole blood spiked with RNA compared to the lysis solution in the QIAamp® DNA Blood Mini Kit. 0.1 pg and 1 pg of influenza A RNA were spiked and extracted using PSS or AL Lysis buffer. At both RNA concentrations, PSS produced superior results as evident by qRT-PCR $C_T$ scores;

FIG. 14B tabulates data from the study shown in FIG. 14A involving the extraction of "naked" H5 avian influenza ssRNA from blood tubes. PSS extraction efficiency of whole blood spiked with RNA compared to the lysis solution in the QIAamp® DNA Blood Mini Kit using different blood anticoagulants. PSS was superior compared to the AL Lysis Buffer from Qiagen using Blood spiked with RNA in common anticoagulant blood-collection tubes; and FIG. 14C tabulates data from the study shown in FIG. 14A involving the comparison of in PSS vs. a commercial extraction kit storage reagent (QIAamp®, Qiagen, Inc.). Shown is the extraction efficiency of PSS for whole blood spiked with RNA compared to the lysis solution in the QIAamp® DNA Blood Mini Kit. 0.1 pg and 1 pg of Influenza A viral RNA were spiked and extracted using PSS or AVL Lysis buffer. At both RNA concentrations, PSS produced superior results as evident by qRT-PCR $C_T$ scores.

FIG. 15A and FIG. 15B show the qPCR amplification of 141 nucleotide single stranded DNA using an assay specific for detecting the IPC. FIG. 15A: Amplification was performed in duplicate reactions using $10^{-6}$ to $10^{-13}$ (i.e., 8-logs) of serially-diluted DNA template. FIG. 15B: IPC standard curve of DNA amplification. The assay slope was −3.39 and the calculated PCR efficiency was 97.23% using $E=10^{(-1/slope)}-1$. qPCR was performed using the Applied Biosystems ABI7500 platform.

FIG. 16A and FIG. 16B show the qRT-PCR amplification of a 130-nucleotide ssRNA carrier molecule capable of serving as an IPC. In FIG. 16A, shown: Amplification was performed in duplicate reactions using 5 picograms (pg) ($2.75\times10^7$ copies) to 5 attograms (ag) (~2-10 copies) of serially-diluted RNA template. In FIG. 16B, shown is the IPC standard curve for amplification of the carrier ssRNA molecule. The assay slope was −3.144 and the calculated PCR efficiency was 100% using $E=10^{(-1/slope)}-1$. qRT-PCR was performed using the Applied Biosystems ABI7500 platform.

FIG. 17 shows PSS containing synthetic ssRNA carrier/IPC molecules enhanced the preservation of naked RNA pathogen target. In this study, a naked influenza A RNA template (1.27 ng/µl) was added to a human nasal wash specimen and preserved PSS with (closed squares) or without (closed circles) synthetic RNA augmentation at 37° C. RNA was extracted, and then subsequently detected via qRT-PCR. The presence of the synthetic ssRNA carrier/IPC molecules in the formulation resulted in both an enhanced initial extraction (on day 0) of sample polynucleotides, and also a stable preservation of the isolated polynucleotides over extended periods of time (see e.g., day 31).

Figure 18:
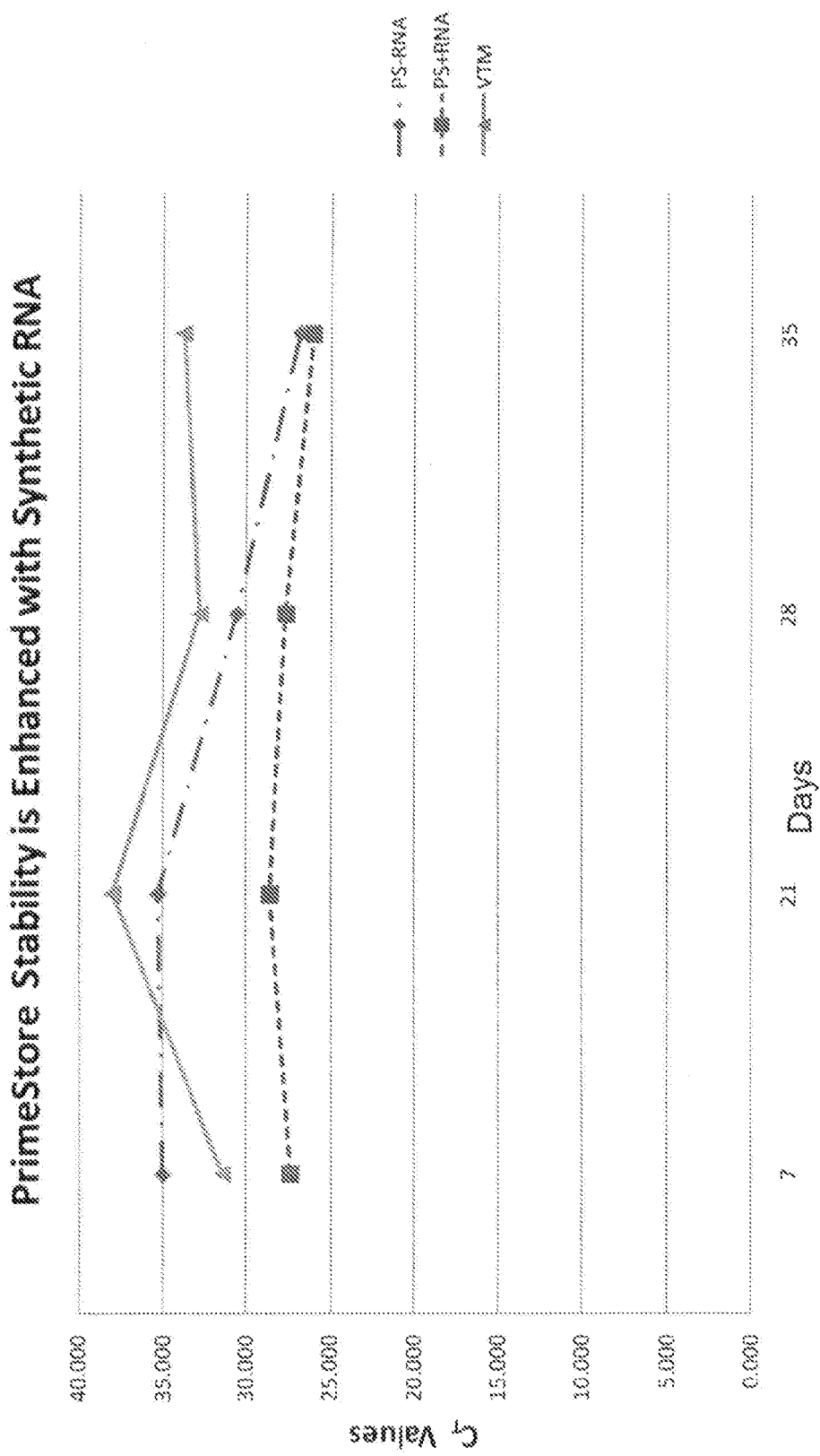

FIG. 18 illustrates that the ability of PSS to stabilize and preserve sample polynucleotides in solution is enhanced by the addition of synthetic ssRNA carrier/IPC nucleic acids to the PSS formulation. In this study, whole influenza A virus was preserved in PSS with (closed squares) or without (closed circles) synthetic ssRNA carrier/IPC augmentation at 37° C. for 35 days. Whole flu virus was also preserved into VTM (closed triangles). RNA was extracted and detected using qRT-PCR. The presence of the synthetic carrier RNA molecule in the formulation resulted in both an enhanced initial extraction (on day 0) of sample polynucleotides, and also a stable preservation of the isolated polynucleotides over extended periods of time (see e.g., day 35).

Figure 19:
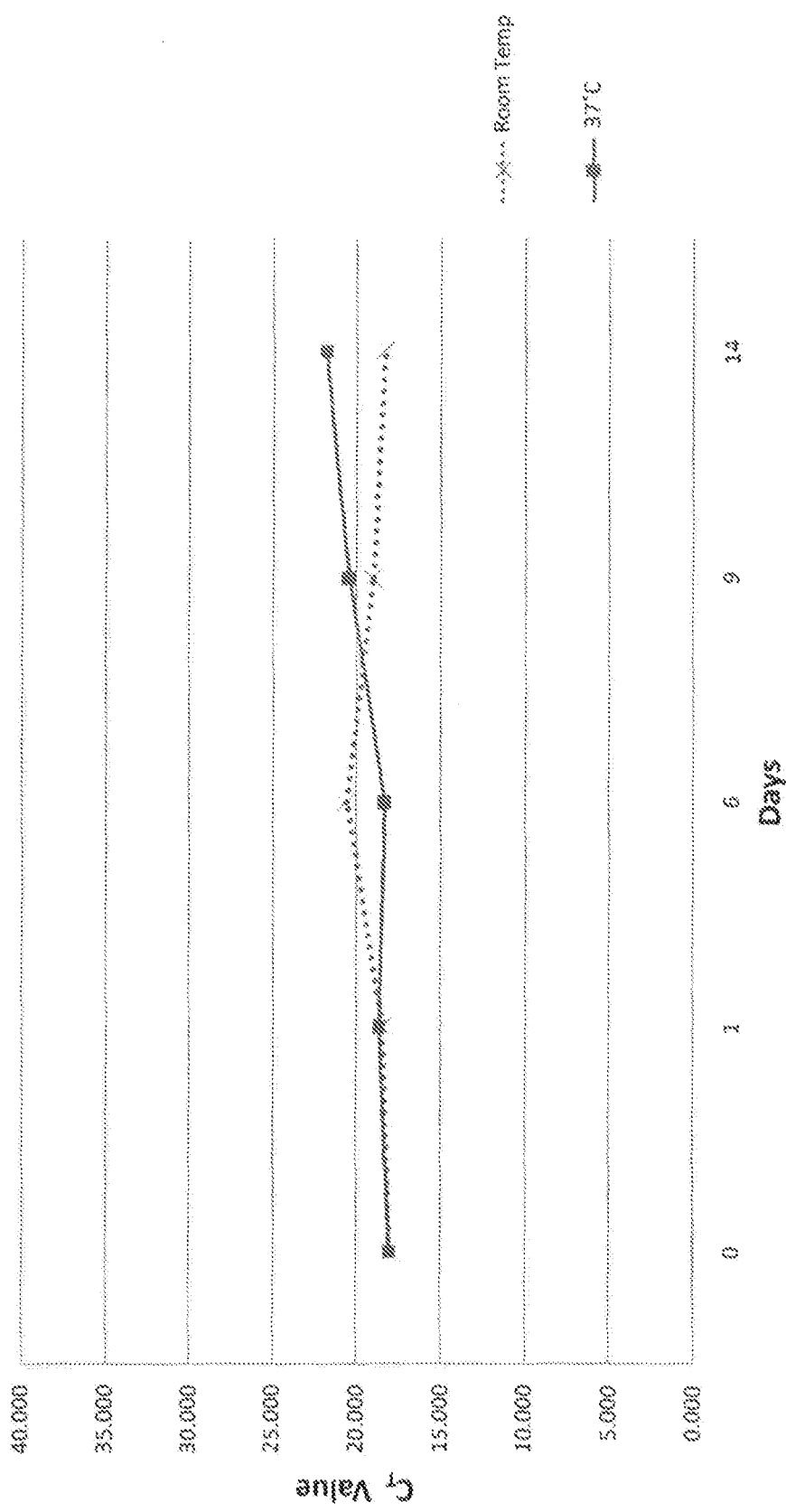

FIG. 19 illustrates the stability of the synthetic ssRNA carrier molecule at room temperature and 37° C. In this study, synthetic RNA (0.1 pg/µl) was added to PSS and stored at room temperature (RT) or 37° C. for 14 days. Stability of the RNA was measured as a function of qRT-PCR using the IPC assay using the Applied Biosystems ABI7500 platform. Synthetic RNA was stable at RT and 37° C. for 14 days with no significant loss in $C_T$ values. The average of duplicate reactions is shown.

DETAILED DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Likewise, it will also be appreciated that while such development efforts may be either complex or time-consuming, they would nevertheless be a routine undertaking for one of ordinary skill in the art having the benefit of the present disclosure.

The extended stabilization, collection, transport, and preservation imparted by the disclosed formulations are particularly advantageous when a sample or specimen is located in a geographical region that is remote from a testing facility. Remote locations, also referred to as field sites, encompass a variety of environments where diagnostic testing is typically not performed. These sites include doctors' offices, triage centers, airports, border crossings, outbreak areas, and a variety of outdoor locations. The disclosed compositions and methods for their use offer particular advantages in locations where there is no access to electricity and/or refrigeration, or where access is inconsistent. Because of the extended stability at room temperature, a sample can be taken from any remote location, for example without limitation at a malarial outbreak site in Africa, and the sample can be shipped to the United States or Europe for diagnostic analysis in a laboratory. Because the disclosed collection formulations are stable at room temperature or below, and preferably even at tropical or subtropical temperatures for a time, they can routinely be taken into the field without worry that the component reagents (such as RNA controls) themselves will degrade until a sample can be analyzed, typically at a remote location from the collection.

The compositions of the invention may be any suitable aqueous formulation as described herein, including but not limited to a solution, suspension (incl. colloidal suspension), slurry, emulsion, homogenate, or the like. A preferred aqueous formulation is a solution, and therefore the term "solution" has been used in the exemplary sense throughout the detailed description of the preferred embodiments to refer to any of the aqueous compositions of the invention.

Important aspects of the present invention concern isolated RNA and DNA segments and recombinant vectors and populations of polynucleotides comprising them, and the creation and use of recombinant methodologies to prepare RNA carrier molecules through the application of conventional molecular biology technologies, including, without limitation, qPCR, qRT-PCR and the like.

The present invention also concerns nucleic acid compositions, including, without limitation, DNA, RNA and PNA, isolatable from one or more biological samples or specimens using the specimen collection/storage/transport media described herein, or the isolated RNA or DNA segments utilized as carrier molecules and/or IPCs.

As used herein, the term "DNA segment" refers to a DNA molecule that has been isolated free of total genomic DNA of a particular species. Therefore, a DNA segment obtained from a biological sample using one of the compositions disclosed herein, refers to one or more DNA segments that have been isolated away from, or purified free from, total mammalian or human genomic DNA. Included within the term "DNA segment", are DNA segments and smaller fragments of such segments, as well as recombinant vectors, including, for example, plasmids, cosmids, phage, viruses, and the like.

Similarly, the term "RNA segment" refers to an RNA molecule that has been isolated free of total cellular RNA of a particular species. Therefore, RNA segments obtained from a biological sample using one of the compositions disclosed herein, refers to one or more RNA segments (either of native or synthetic origin) that have been isolated away from, or purified free from, other RNAs. Included within the term "RNA segment", are RNA segments and smaller fragments of such segments.

A nucleic acid segment comprising an isolated and/or purified polynucleotide refers to a nucleic acid segment isolated substantially away from other naturally occurring genes or protein-encoding sequences that may be present in the biological sample undergoing collection and subsequent analysis.

In particular embodiments, the invention concerns nucleic acid sample collection, storage, and transport media that comprise a first carrier molecule to aid in the isolation and stabilization of nucleic acids obtained from such samples. Preferably, the carrier molecules are single-stranded RNA molecules, although in some circumstances, RNA:RNA, or RNA:DNA duplex molecules may also be utilized.

While the particular molecular mechanism for how the incorporation of exogenous carrier molecules, and RNA molecules in particular, into the specimen collection/storage/transport formulations disclosed herein need not be elucidated for the routine practice of the invention, without being limited by any particular theory, the inventors believe that the presence of exogenously-supplied RNA carrier, molecules in PSS and related formulations described herein aids in the precipitation and stabilization of polynucleotides that are liberated from the cellular material when contacted with PSS, and may also serve as a method for "coating" or "enrobing" the liberated sample nucleic acids in a protective molecular form that is favorable to polynucleotide agglomeration or precipitation.

Regardless of the mechanism of action, the inventors have demonstrated the surprising benefits afforded over conventional polynucleotide isolation solutions in the preparation of high-quality, high-fidelity populations of nucleic acids that are spared the deleterious effects routinely observed in conventional samples that are subjected to degradation and contamination during the collection, isolation, storage, and transport processes.

Carrier molecules and/or IPC-containing sequences may be synthesized in part or in whole, using conventional methodologies known in the art, or may be prepared from recombinant molecular biological methods (including, without limitation, in vitro transcription and/or translation methods, such as PCR amplification), or may be obtained from native biological sources (preferably from non-mammalian sources and sources which are not pathogenic to mammalian species. Alternatively, the carrier RNA molecules of the present invention may be hybrid molecules—containing both natural and synthetic portions operably linked using one or more conventional methods in the molecular genetic and recombinant DNA/RNA arts. In certain applications the RNA carrier molecules may be comprised of one or more transcription initiation sequences, primer or probe binding domains, functionalized binding sites, exo- or endo-nuclease cleavage sites, and/or functional motifs or active sites.

The term "a sequence essentially as set forth in SEQ ID NO:X" means that the sequence substantially corresponds to a portion of SEQ Ib NO:X and has relatively few nucleotides (or amino acids in the case of polypeptide sequences) that are not identical to, or a biologically functional equivalent of, the nucleotides of SEQ ID NO:X. The term "biologically functional equivalent" is well understood in the art, and is further defined in detail herein. Accordingly, sequences that have about 85% to about 90%; or more preferably, about 91% to about 95%; or even more preferably, about 96% to about 99%; of nucleotides that are identical or functionally equivalent to one or more of the nucleotide sequences provided herein are particularly contemplated to be useful in the practice of the invention.

Suitable standard hybridization conditions for the present invention include, for example, hybridization in 50% formamide, 5×Denhardts' solution, 5×SSC, 25 mM sodium phosphate, 0.1% SDS and 100 μg/ml of denatured salmon sperm DNA at 42° C. for 16 h followed by 1 hr sequential washes with 0.1×SSC, 0.1% SDS solution at 60° C. to remove the desired amount of background signal. Lower stringency hybridization conditions for the present invention include, for example, hybridization in 35% formamide, 5×Denhardts' solution, 5×SSC, 25 mM sodium phosphate, 0.1% SDS and 100 μg/ml denatured salmon sperm DNA or E. coli DNA at 42° C. for 16 h followed by sequential washes with 0.8×SSC, 0.1% SDS at 55° C. Those of skill in the art will recognize that conditions can be readily adjusted to obtain the desired level of stringency.

Naturally, the present invention also encompasses DNA segments that are complementary, or essentially complementary, to one or more of the specific sequences set forth herein. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to one or more of the specific nucleic acid segments disclosed herein under relatively stringent conditions such as those described immediately above.

As described above, the probes and primers of the present invention may be of any length. By assigning numeric values to a sequence, for example, the first residue is 1, the second residue is 2, etc., an algorithm defining all primers can be proposed: n to n+y where n is an integer from 1 to the last number of the sequence and y is the length of the primer minus one, where n+y does not exceed the last number of the sequence. Thus, for a 25-mer, the probes correspond to bases 1 to 25, 2 to 26, 3 to 27 . . . and so on. For a 45-mer, the probes correspond to bases 1 to 45, 2 to 46, 3 to 47 . . . and so on. For a 60-mer, the probes correspond to bases 1 to 60, 2 to 61, 3 to 62 . . . and so on.

In certain embodiments, it will be advantageous to employ nucleic acid sequences of the present invention in combination with an appropriate detectable marker (i.e., a "label,") for determining hybridization. A wide variety of appropriate indicator compounds and compositions are known in the art, including, without limitation, fluorescent, radioactive, enzymatic or other ligands, such as avidin/biotin, etc., which are capable of being detected. In particular embodiments, one may desire to employ a fluorescent label or an enzyme tag such as urease, alkaline phosphatase or peroxidase, instead of radioactive or other environmentally less-desirable reagents. In the case of enzyme tags, colorimetric, chromogenic, or fluorigenic indicator substrates are known that can be employed to provide a method for detecting the sample that is visible to the human eye, or by analytical methods such as scintigraphy, fluorimetry, spectrophotometry, and the like, to identify specific hybridization with samples containing one or more complementary or substantially complementary nucleic acid sequences.

In general, it is envisioned that the hybridization probes described herein will be useful both as reagents in solution hybridization, as in PCR, for detection of particular nucleotides, as well as in embodiments employing a solid phase.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual inspection. Alternatively, the detection may involve indirect identification of the product via chemiluminescence, radioactive scintigraphy of incorporated radiolabel or fluorescent label or even via a system using electrical or thermal impulse signals.

A number of template dependent processes are available to amplify the marker sequences present in a given template sample. One of the best-known amplification methods is the polymerase chain reaction (referred to as PCR) which is described in detail in U.S. Pat. Nos. 4,683,195, 4,683,202 and 4,800,159, and each incorporated herein by reference in entirety.

Another method for amplification is the ligase chain reaction ("LCR"), disclosed, e.g., in EPA No. 320 308, and U.S. Pat. No. 4,883,750, each of which is incorporated herein in its entirety by express reference thereto.

An isothermal amplification method, in which restriction endonucleases and ligases are used to achieve the amplification of target molecules that contain nucleotide 5'-[α-thio]- triphosphates in one strand of a restriction site may also be useful in the amplification of nucleic acids in the present invention.

Strand Displacement Amplification (SDA) is another method of carrying out isothermal amplification of nucleic acids that involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Methods based on ligation of two (or more) oligonucleotides in the presence of nucleic acid having the sequence of the resulting "di-oligonucleotide," thereby amplifying the di-oligonucleotide, may also be used in the amplification step of the present invention.

Following any amplification, it may be desirable to separate the amplification product from the template and the excess primer for determining whether specific amplification has occurred. In one embodiment, amplification products are separated by agarose, agarose-acrylamide or polyacrylamide gel electrophoresis using conventional methods that are known to those of ordinary skill in the art.

Polynucleotide and Oligonucleotide Compositions

As used herein, "nucleic acid" or "polynucleotide" compositions include, but are not limited to, those that contain either single-stranded or double-stranded polynucleotides, such as for example, deoxyribonucleic acids (DNA), ribonucleic acids (RNA), peptide nucleic acids (PNA), or any combinations or derivatives thereof (including, e.g., genomic, extragenomic, plasmid, cosmid, recombinant, artificial, and/or synthetic). Such sequences may be coding or non-coding sequences, sense, non-sense, or anti-sense sequences, and may, but need not, be present within one or more populations or pluralities of polynucleotides (either of the present invention, and a polynucleotide may, but need not, be linked to other molecules and/or support materials.

Likewise, polynucleotides of the present invention, and particularly those functioning as carrier polynucleotides or IPC molecules in the disclosed specimen collection/transportation media, need not be identical, or even substantially homologous to the particular sequences employed in the various embodiments of the invention illustrated herein. While the inventors have illustrated the use of particular DNA and RNA control sequences as tools for monitoring the integrity and quality, and preferably, increasing the stability, of polynucleotides collected, transported, or stored in the compositions described herein, such control sequences need not contain the particular nucleotide sequences employed.

In fact, in certain circumstances, polynucleotides useful as internal control sequences in the disclosed collection/transport/storage compositions may comprise any suitable sequence that may be obtained, prepared, modified, or synthesized for such purpose. Moreover, it is preferable that such internal control sequences do not share significant homology or identity with the viral, bacterial, fungal, or other pathogenic species sought to be identified using the disclosed formulations.

Alternatively, polynucleotides suitable as IPCs may be homologous to, or even substantially identical to, one or more of the exemplary IPC sequences disclosed herein, and as such, may be capable of hybridizing to one of the specific IPC sequences disclosed herein (or a sequence that is complementary thereto) under moderately stringent, highly stringent, and/or even very highly stringent hybridization conditions.

The methods for nucleic acid hybridization are considered routine to those of ordinary skill in the molecular biological arts, and as such, a detailed discussion of analytical methods employing them need not be provided herein. However, as a guidance, "moderately stringent" hybridization conditions popularized by Southern et al. are generally considered in the art to include, e.g., pre-washing in a solution containing about 5× standard sodium citrate buffer (SSC), 0.5% sodium dodecyl sulfate (SDS), 1.0 mM ethylenediaminetetraacetic acid (EDTA) (e.g., pH 8.0); hybridizing at a temperature of from about 50° C. to about 60° C. in 5×SSC overnight; followed by washing twice at about 60 to 65° C. for 20 min. with each of 2×, 0.5× and 0.2×SSC containing 0.1% SDS). Likewise, "stringent" hybridization conditions typically include, e.g., pre-washing in a solution containing about 5×SSC, 0.5% SDS, 1.0 mM EDTA (pH 8.0); hybridizing at a temperature of from about 60° C. to about 70° C. in 5×SSC overnight; followed by washing twice at about 65 to 70° C. for 20 min. with each of 2×, 0.5× and 0.2×SSC containing 0.1% SDS). Similarly, representative examples of "highly-stringent" hybridization conditions include, but are not limited to, pre-washing in a solution containing about 5×SSC, 0.5% SDS, 1.0 mM EDTA (pH 8.0); hybridizing at a temperature of from about 70° C. to about 75° C. in 5×SSC overnight; followed by washing twice at about 70° C. to about 75° C. for 20 min. with each of 2×, 0.5× and 0.2×SSC containing 0.1% SDS).

It will also be appreciated by those of ordinary skill in the art that, as a result of the degeneracy of the genetic code, there are many nucleotide sequences that encode a given primary amino acid sequence. Some of these polynucleotides bear minimal homology to the nucleotide sequence of any native gene. Nonetheless, polynucleotides that vary due to differences in codon usage are specifically contemplated by the present invention.

IPCs may be prepared by conventional molecular biology recombination methodologies, or alternatively synthesized in whole or in part by conventional methods known in the art, including chemical synthesis (e.g., solid phase phosphoramidite chemical synthesis) and the like. Modifications in a polynucleotide sequence may also be introduced using standard mutagenesis techniques, such as oligonucleotide-directed site-specific mutagenesis. RNA molecules for IPCs may also be directly synthesized, or alternatively, be prepared by in vitro or in vivo transcription of DNA sequences using suitable systems (such as T3, T7, and SP6 polymerases and the like).

Polynucleotides of the present invention, and particularly those used to prepare IPCs, may be modified to increase stability either in vitro and/or in vivo. Such modifications include, without limitation, the addition of flanking sequences at the 5'-end, 3'-end, or both; the use of phosphorothioate or 2'-o-methyl rather than phosphodiesterase linkages in the backbone; and/or the inclusion of nontraditional bases such as inosine, queosine and wybutosine, as well as acetyl-, methyl-, thio-, or otherwise-modified forms of adenine, cytidine, guanine, thymine and uridine, or any combination thereof.

Nucleotide sequences as described herein may be joined or linked to a variety of other nucleotide sequences using established recombinant techniques. For example, a polynucleotide useful as an IPC may be produced by cloning into any of a variety of cloning vectors, including one or more of plasmids, phagemids, lambda phage derivatives and cosmids. Vectors of particular interest include expression vectors, replication vectors, probe generation vectors, and sequencing vectors. In general, a vector will contain an origin of replication functional in at least one organism, convenient restriction endonuclease sites and one or more selectable markers. Other elements will depend upon the desired use, and will be apparent to those of ordinary skill in the art. Alternatively, IPC sequences may be prepared through one or more template-dependent, or amplicon-directed recombinant production methodologies.

In particular embodiments, the present invention provides polynucleotide compositions that may be added to the disclosed collection/storage/transport media to provide one or more IPCs to monitor the fidelity and integrity of the sampling/storage/and transporting processes employed herein. Such polynucleotide compositions may contain one or more sequence domains to which specific polymerases, oligonucleotides primers, and/or recombinant probes may bind. In illustrative embodiments, exemplary IPCs may be employed, which contain a positive control sequence (PCS) that may be amplified using one or more specific amplification primer sequences, and detected and/or quantitated using one or more oligonucleotides probes that specifically hybridize to at least a first sequence domain of the PCS. In certain embodiments, detection probes may be utilized that employ fluorescent, chemiluminescent, or FRET-specific detection methodologies to detect and/or quantitate the amount of PCS in a given sample. Detection of the PCS in a sample can provide an internal reference standard for monitoring the effectiveness and fidelity of the one-step collection/storage/transport solutions employed herein.

Oligonucleotide primers and probes of the present invention may be designed for the selective amplification and detection of one or more PCS. Such primer sequences are suitable for use in hybridization methods, and in amplification methods such as PCR-based amplification methods (including, for example, real-time PCR analyses, RT-PCR and the like). Likewise, the disclosed oligonucleotide detection probes are suitable for labeling with an appropriate label for detection and quantitation of the products resulting from the amplification of nucleic acids using one or more pairs of the amplification primers disclosed herein.

When labeled with appropriate markers, oligonucleotide detection probes are particularly suited for fluorescence-based detection of the IPC-specific nucleotide sequences contained in the collection/storage medium (including, without limitation, PSS formulations), including, for example, via FRET-based analyses. FRET-labeled detection probes are particularly useful in fluorimetric detection methodologies, including for example, the FRET-based microvolume fluorimetry devices. Use of one or more amplification and detection oligonucleotides is particularly contemplated in the combined real-time PCR/microvolume fluorimetry FRET-based methodologies (real-time PCR-FRET), and particularly in analyses facilitated by the "LightCycler®" instrumentation as developed by Idaho Technology, Inc. (Salt Lake City, Utah, USA), and now manufactured and marketed by Roche Applied Science (Indianapolis, Ind., USA).

Internal Positive Control (IPC) Sequences

In illustrative embodiments, the invention also provides IPC sequences that comprise, consist essentially of, or consists of, nucleic acid sequences that are preferably at least about 80%, at least about 85%, at least about 90%, at least about 95%, at least about 96%, at least about 97%, at least about 98%, or at least about 99% or more identical to any one or more of the sequences disclosed above, and particularly those disclosed in any one of SEQ ID NO:2 through SEQ ID NO:13.

In related embodiments, the invention also provides IPC sequences that are synthesized in vitro using a template amplicon that comprises, consists essentially of, or consists of, nucleic acid sequences that are preferably at least about 80%, at least about 85%, at least about 90%, at least about 95%, at least about 96%, at least about 97%, at least about 98%, or at least about 99% or more identical to an at least 30 contiguous nucleotide sequence from any one or more of the sequences disclosed in SEQ ID NO:1, or SEQ ID NO:14 through SEQ ID NO:23.

Polynucleotide Amplification Kits

The present invention also provides kits for detecting and/or amplifying IPCs, and in particular RNA or DNA IPC sequences contained within one of the formulations disclosed herein, including without limitation, PSS formulations. Such kits typically comprise two or more components necessary for amplifying IPC-specific sequences, and such components may be compounds, reagents, containers and/or equipment. For example, one container within a kit may contain a first primer, while a second container within the kit may comprise a second primer. A third container within the kit may contain a set of hybridization probes, or one or more fluorescent probes for labeling the probes. In addition, the kits of the invention may also comprise instructions for use, e.g., instructions for using the primers in amplification and/or detection reactions as described herein, as well as one or more fluorescent molecules or other reagents as may be necessary, including for example, but not limited to, buffers enzymes, polymerases, RNases and such like.

The invention provides one or more carrier RNA or DNA compositions together with one or more collection/transport/storage solutions (including, without limitation, PSS formulations), or compatible excipients, buffers carriers, diluents, adjuvants, and/or other components, as may be employed in the isolation, detection, amplification, or quantitation of diagnostic tools.

Real-Time PCR-Based Fret Detection

Real-time PCR and FRET methodologies have been well described in the literature (see, for example, U.S. Pat. Nos. 4,996,143, 5,565,322, 5,849,489, 6,162,603, each of which is specifically incorporated herein in its entirety by express reference thereto). The LightCycler® platform represents a significant breakthrough in genetic mutation screening and analysis. This system incorporates a rapid, air-driven thermal cycling instrument that can perform 30 polymerase chain reaction (PCR) cycles in less than 20 minutes. It utilizes an in-line microvolume fluorimeter to detect and quantitate fluorescently-labeled hybridization probes, and provides the data necessary for determination of melting curve analyses. The LightCycler® platform provides innovative instrumentation to facilitate the development of genetic analysis tools, and to provide a rapid, qualitative method for the assay of specific nucleotide sequences, and genetic mutations. Detailed application of the instrumentation in amplification and detection methods may be found on the manufacturer's website, and in product application manuals. This technology has also been described, including for example PCT Intl. Appl. Publ. Nos. WO 97/46707, WO 97/46714 and WO 97/46712 (each of which is specifically incorporated in its entirety by express reference thereto).

Specimen Collection for Clinical Diagnostic Laboratories

Collection is first step in diagnostic platforms or molecular protocols requiring the detection of potentially minute amounts of nucleic acids from pathogens including viruses. To facilitate the dynamic advancements in nucleic acid based detection strategies and their integration into the mainstream diagnostic laboratories there is a colossal need for reliable, robust, and standardized collection systems developed specifically with the intent of being utilized for downstream nucleic acid based detection such as the aforementioned platforms. The invention can alternatively be adapted for transport of nucleic acids from a doctor's office or operating room, or alternatively transported to a regional center, such as a hospital.

A clinical or veterinary specimen or a forensic or environmental sample collection system may include one or more collection tools and one or more reagents for efficiently:

1) obtaining a high yield of suitable specimen beyond what is currently available in the art;

2) inactivating potentially infectious biological pathogens so that they are no longer viable and can be handled; shipped, or transported with minimal fear of pathogen release or contamination; or 3) effectively stabilizing and preserving lysed 'naked' RNA/DNA polymers from hydrolysis or nuclease degradation for prolonged periods at ambient temperatures until samples can be processed at a diagnostic laboratory, and preferably for achieving two or more, or all three, of these goals.

As noted herein, the sample collection/transport/storage solutions of the present invention can provide a number of significant improvements over those available in the prior art. Exemplary benefits include, without limitation, one or more of the following:

- inactivation, killing, and/or lysis of microbes, viruses, or pathogens;
- destruction and/or inactivation of exogenous or endogenous nucleases, including, without limitation, RNase and/or DNase;
- compatibility with a variety of conventional nucleic acid extraction, purification, and amplification systems;
- preservation of RNA and/or DNA integrity within the sample;
- facilitation of transport and shipping at ambient temperatures, even over extended periods of time, or extreme temperature variations; and
- suitability for short—(several hours to several days), intermediate—(several days to several weeks), or long—(several weeks to several months) term storage of the isolated nucleic acids.

The disclosed compositions are particularly well suited for point-of-care, field studies, in-home health care or testing, triage/emergency and casualty assessment(s), mobile forensics, pathology, epidemiological sampling, crime-scene investigation, paternity testing, pre- and post-pregnancy genetic screening, rape/incest testing, family counseling, confidential testing of sexually transmitted diseases (including, without limitation, HIV, syphilis, Chlamydia, gonorrhea, and other venereal diseases and the like). Likewise, the disclosed compositions may also be of particular relevance for monitoring, etiology, and control of epidemic or pandemic diseases in human or animal populations, both domestically and abroad, including the collection and analysis of influenzavirus-containing specimens, particularly for predicting and managing viral "shift and drift," and identifying or managing emerging or ongoing epidemics, pandemics, and the like.

In certain embodiments, a nucleic acid isolated using the methods of the present invention may serve as a template in one or more subsequent molecular biological applications, assays, or techniques, including, without limitation, genetic fingerprinting; amplified fragment length polymorphism (AFLP) PCR; restriction fragment-length polymorphism analysis (RFLP); allele-specific oligonucleotide analysis (ASOA); microsatellite analysis; Southern hybridization; Northern hybridization; variable number of tandem repeats (VNTR) PCR; dot-blot hybridization; polymerase cycling assembly (PCA); nested PCR; quantitative PCR (qPCR); asymmetric PCR; DNA footprinting; single nucleotide polymorphism (SNP) genotyping; reverse-transcription PCR (RT-PCR); multiplex PCR (m-PCR); multiplex ligation-dependent probe amplification (MLPA); ligation-mediated PCR (LmPCR); methylation specific PCR (MPCR); helicase-dependent amplification (HDA); overlap-extension PCR (OE-PCR); whole-genome amplification (WGA); plasmid isolation; allelic amplification; site-directed mutagenesis; high-throughput genetic screening; or the like, or any combination thereof.

In one embodiment, the specimen collection/storage/transport formulations preserve, extend, facilitate, or maintain the stability of at least a first nucleic acid in a population of polynucleotides liberated from the specimen for an extended period of time, and particularly, e.g., for periods of time substantially longer than those afforded by conventional sample collection media.

Preferably, the composition will facilitate the preservation and stabilization of one or more nucleic acid segments from within such an isolated population of polynucleotides for periods of time including, without limitation, at least about 7 days, preferably at least about 14 days, more preferably, at least about 21 days, and more preferably still, at least about 28, 35, 42, 56, 63, or about 70 days or more, without need for refrigerating, or freezing, the collected sample—even when the sample is collected, or stored, under ambient environmental conditions. Such improved specimen preservation properties are particularly desirable when such samples are collected or stored in remote locations, or in temperate, subtropical or tropical climates.

In another embodiment the invention provides for the use of the disclosed compositions to prepare nucleic acids from a sample of biological origin in maintaining the integrity and fidelity of one or more nucleic acids contained within a population of polynucleotides released from the sample for extended periods including, without limitation, for at least about 5 days, at least about 10 days, preferably at least about 15 days, more preferably at least about 20 days, or more preferably still, at least about 25 days or more, without the requirement of storing the sample under refrigerating or freezing conditions.

Nucleic acids obtained in the practice of the disclosed methods are advantageously compatible with a number of conventional molecular and diagnostic isolation, purification, detection, and/or analytic methodologies. The disclosed compositions facilitate recovery storage, and transport of populations of stabilized, substantially non-degraded, polynucleotides for use in a variety of subsequent methodologies, including, without limitation, nucleic acid isolation, purification, amplification, and molecular analytical and/or diagnostic testing, assay, analysis, or characterization, and the like.

Exemplary Commercial Kits of the Present Invention

Figure 5:
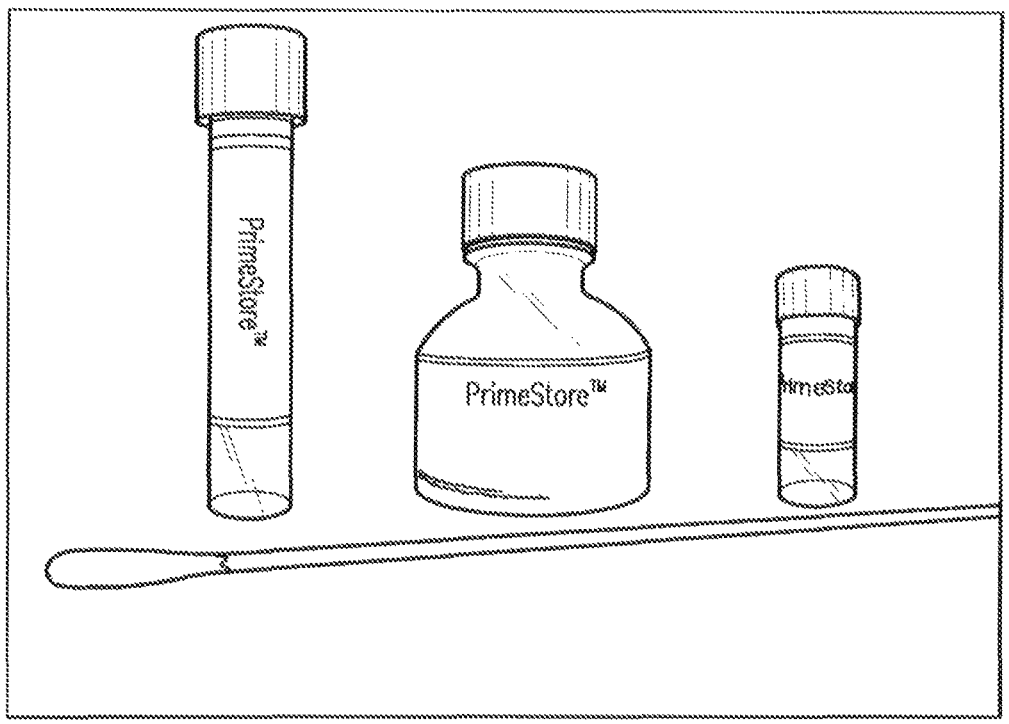
Figure 6:
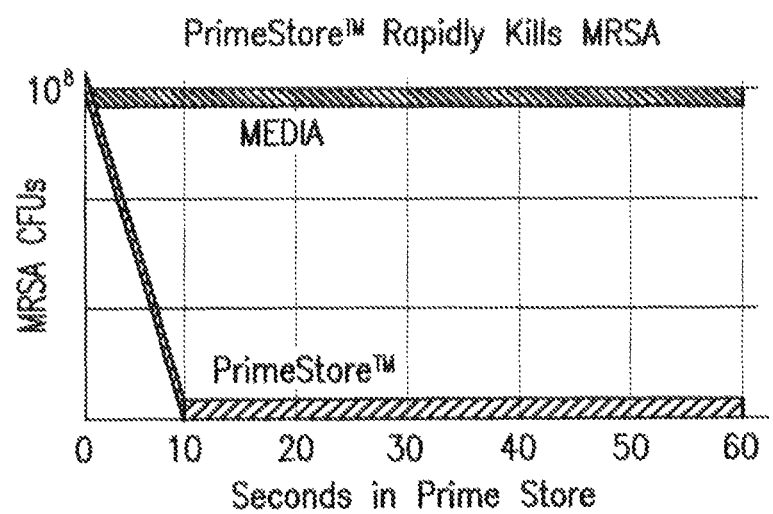

The following outline provides exemplary commercial kits employing the PSS formulations of the present invention (FIG. 5).

Peel-Pouch Collection System

Five-mL tube containing 1.5 mL PrimeStore™ Solution; Collection swab (e.g., FlockedSWABS® [Copan Diagnostics, Inc., Murrieta, Calif., USA]); and instructions for collection and/or processing of samples. (packed, e.g., in 50 pouches/unit) (See FIG. 4A, FIG. 4B, FIG. 4C, FIG. 4D, and FIG. 4E for a schematic demonstration of such systems).

PrimeStore™ Stock Solutions

Once formulated, PrimeStore™ stock solution is stable at 4° C. or below for periods of at least one year or more. Formulated PrimeStore™ solutions have also been shown to be stable at ambient temperature (e.g., about 20-30° C.) for periods of many months.

Once a sample is contacted with a PrimeStore™ formulation as disclosed herein, it can reasonably expected to be stored indefinitely at temperatures of 0° C. or below, at least one year or more under refrigeration (e.g., ≈4° C. and at least 30 days or more at ambient temperature (e.g., about 20-30° C.), without significant loss of nucleic acid composition, fidelity or integrity of the sample. For example, without limitation, the integrity of a population of polynucleotides obtained from the sample is at least substantially maintained, and preferably entirely maintained without detectable degradation, when the composition comprising the sample is stored at a temperature of from about −20° C. to about 40° C., for a period of from about 30 days to about 60 days.

Collection Kits for Environmental Samples

Exemplary commercial packages of the disclosed formulations for the collection of environmental samples include, without limitation, collection vessels containing effective amounts of the storage solution (e.g., 0.1-, 0.2-, 0.5-, 1-, 2-, or 3-mL collection vials each containing 0.1 mL, 0.2 mL, 0.25 mL, 0.5 mL, 0.75 mL, or 1 mL PrimeStore™ solution); and instructions for collection and/or processing of samples. The collection vessels may be sized or packaged in smaller or larger sizes as needed depending on the proposed specimen(s) or collection method(s). In certain applications, it may also be desirable to package individual collection devices into multiple containers (including, without limitation, commercial packs containing e.g., 10 or 20 collection devices/unit package).

Sequence Comparison, Identity, and Homology

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of ordinary skill) or by visual inspection.

The phrase "substantially identical," in the context of two nucleic acids refers to two or more sequences or subsequences that have at least about 90%, preferably 91%, most preferably about 92%, 93%, 94%, 95%, 96%, 97%, 98%, 98.5%, 99%, 99.1%, 99.2%, 99.3%, 99.4%, 99.5%, 99.6%, 99.7%, 99.8%, 99.9% or more nucleotide residue identity, when compared and aligned for maximum correspondence, as measured using a sequence comparison algorithm or by visual inspection. Such "substantially identical" sequences are typically considered "homologous," without reference to actual ancestry.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm can then be used to calculate the percent sequence identity for the test sequence(s) relative to the reference sequence, based on the designated program parameters.

Optimal alignment of sequences for comparison can be conducted, e.g., by the local homology algorithm (see e.g., Smith and Waterman, 1981), by the homology alignment algorithm (see e.g., Needleman and Wunsch, 1970), by the search similarity comparison method (see e.g., Pearson and Lipman, 1988), by computerized implementations of algorithms such as GAP, BESTFIT, FASTA, and TFASTA in the Wisconsin Genetics Software Package, Genetics Computer Group, Madison, Wis., USA, or by visual inspection. One example of an algorithm that is suitable for determining percent sequence identity and sequence similarity is the BLAST algorithm (Altschul et al., 1990) and BLOSUM62 scoring matrix (see, e.g., Henikoff and Henikoff, 1989). Software for performing BLAST analyses is publicly available through the National Center for Biotechnology Information (www.ncbi.nlm.nih.gov/).

In addition to calculating percent sequence identity, the BLAST algorithm also performs a statistical analysis of the similarity between two sequences (see, e.g., Karlin and Altschul, 1993). Another example of a useful sequence alignment algorithm is the PILEUP program, which creates a multiple sequence alignment from a group of related sequences using progressive, pairwise alignments. It can also plot a tree showing the clustering relationships used to create the alignment. PILEUP uses a simplification of the progressive alignment comparison method (see e.g., Feng and Doolittle, 1987), and employs a general alignment matrix similar to that described by Higgins and Sharp (1989).

Exemplary Definitions

Unless defined otherwise, all technical and scientific terms used herein have the same meaning as commonly understood by one of ordinary skill in the art to which this invention belongs. Although any methods and compositions similar or equivalent to those described herein can be used in the practice or testing of the present invention, the preferred methods and compositions are described herein. For purposes of the present invention, the following terms are defined below:

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

As used herein, the term "carrier" is intended to include any solvent(s), dispersion medium, coating(s), diluent(s), buffer(s), isotonic agent(s), solution(s), suspension(s), colloid(s), inert(s) or such like, or a combination thereof that is pharmaceutically acceptable for administration to the relevant animal or acceptable for a diagnostic purpose, as applicable. The use of one or more delivery vehicles for chemical compounds in general, and peptides and epitopes in particular, is well known to those of ordinary skill in the pharmaceutical arts. Except insofar as any conventional media or agent is incompatible with the active ingredient, its use in the diagnostic, prophylactic, and therapeutic compositions is contemplated. One or more supplementary active ingredient(s) may also be incorporated into, or administered in association with, one or more of the disclosed immunogenic compositions.

As used herein, the term "nucleic acid" includes one or more types of: polydeoxyribonucleotides (containing 2-deoxy-D-ribose), polyribonucleotides (containing D-ribose), and any other type of polynucleotide that is an N-glycoside of a purine or pyrimidine base, or modified purine or pyrimidine bases (including abasic sites). The term "nucleic acid," as used herein, also includes polymers of ribonucleosides or deoxyribonucleosides that are covalently bonded, typically by phosphodiester linkages between subunits, but in some cases by phosphorothioates, methylphosphonates, and the like. "Nucleic acids" include single- and double-stranded DNA, as well as single- and double-stranded RNA. Exemplary nucleic acids include, without limitation, gDNA; hnRNA; mRNA; rRNA, tRNA, micro RNA (miRNA), small interfering RNA (siRNA), small nucleolar RNA (snORNA), small nuclear RNA (snRNA), and small temporal RNA (stRNA), and the like, and any combination thereof.

As used herein, the terms "protein," "polypeptide," and "peptide" are used interchangeably, and include molecules that include at least one amide bond linking two or more amino acid residues together. Although used interchangeably, in general, a peptide is a relatively short (e.g., from 2 to about 100 amino acid residues in length) molecule, while a protein or a polypeptide is a relatively longer polymer (e.g., 100 or more residues in length). However, unless specifically defined by a chain length, the terms peptide, polypeptide, and protein are used interchangeably.

As used herein, "sample" includes anything containing or presumed to contain a substance of interest. It thus may be a composition of matter containing nucleic acid, protein, or another biomolecule of interest. The term "sample" can thus encompass a solution, cell, tissue, or population of one of more of the same that includes a population of nucleic acids (genomic DNA, cDNA, RNA, protein, other cellular molecules, etc.). The terms "nucleic acid source," "sample," and "specimen" are used interchangeably herein in a broad sense, and are intended to encompass a variety of biological sources that contain nucleic acids, protein, one or more other biomolecules of interest, or any combination thereof. Exemplary biological samples include, but are not limited to, whole blood, plasma, serum, sputum, urine, stool, white blood cells, red blood cells, buffy coat, swabs (including, without limitation, buccal swabs, throat swabs, vaginal swabs, urethral swabs, cervical swabs, rectal swabs, lesion swabs, abscess swabs, nasopharyngeal swabs, and the like), urine, stool, sputum, tears, mucus, saliva, semen, vaginal fluids, lymphatic fluid, amniotic fluid, spinal or cerebrospinal fluid, peritoneal effusions, pleural effusions, exudates, punctates, epithelial smears, biopsies, bone marrow samples, fluid from cysts or abscess contents, synovial fluid, vitreous or aqueous humor, eye washes or aspirates, pulmonary lavage or lung aspirates, and organs and tissues, including but not limited to, liver, spleen, kidney, lung, intestine, brain, heart, muscle, pancreas, and the like, and any combination thereof. In some embodiments, the sample may be, or be from, an organism that acts as a vector, such as a mosquito, or tick, or other insect(s).

Tissue culture cells, including explanted material, primary cells, secondary cell lines, and the like, as well as lysates, homogenates, extracts, or materials obtained from any cells, are also within the meaning of the term "biological sample," as used herein. Microorganisms (including, without limitation, prokaryotes such as the archaebacteria and eubacteria; cyanobacteria; fungi, yeasts, molds, actinomycetes; spirochetes, and mycoplasmas); viruses (including, without limitation the Orthohepadnaviruses [including, e.g., hepatitis A, B, and C viruses], human papillomavirus, Flaviviruses [including, e.g., Dengue virus], Lyssaviruses [including, e.g., rabies virus], Morbilliviruses [including, e.g., measles virus], Simplexviruses [including, e.g., herpes simplex virus], Polyomaviruses, Rubulaviruses [including, e.g., mumps virus], Rubiviruses [including, e.g., rubella virus], Varicellovirus [including, e.g., chickenpox virus], rotavirus, coronavirus, cytomegalovirus, adenovirus, adeno-associated virus, baculovirus, parvovirus, retrovirus, vaccinia, poxvirus, and the like), algae, protozoans, protists, plants, bryophytes, and the like, and any combination of any of the foregoing, that may be present on or in a biological sample are also within the scope of the invention, as are any materials obtained from clinical or forensic settings that contain one or more nucleic acids are also within the scope of the invention. The ordinary-skilled artisan will also appreciate that lysates, extracts, or materials obtained from any of the above exemplary biological samples are also within the scope of the invention.

As used herein, the term "buffer" includes one or more compositions, or aqueous solutions thereof, that resist fluctuation in the pH when an acid or an alkali is added to the solution or composition that includes the buffer. This resistance to pH change is due to the buffering properties of such solutions, and may be a function of one or more specific compounds included in the composition. Thus, solutions or other compositions exhibiting buffering activity are referred to as buffers or buffer solutions. Buffers generally do not have an unlimited ability to maintain the pH of a solution or composition; rather, they are typically able to maintain the pH within certain ranges, for example from a pH of about 5 to 7.

As used herein, the term "biological molecule" refers to any molecule found within a cell or produced by a living organism, including viruses. This may include, but is not limited to, nucleic acids, proteins, carbohydrates, and lipids. As used herein, a "cell" refers to the smallest structural unit of an organism that is capable of independent functioning and is comprised of cytoplasm and various organelles surrounded by a cell membrane. This may include, but is not limited to, cells that function independently such as bacteria and protists, or cells that live within a larger organism such as leukocytes and erythrocytes. As defined herein, a cell may not have a nucleus, such as a mature human red blood cell.

Samples in the practice of the invention can be used fresh, or can be used after being stored for a period of time, or for an extended period of time, including for example, cryopreserved, frozen, or refrigerated samples and the like, and may include material of clinical, veterinary, environmental or forensic origin, may be isolated from food, beverages, feedstocks, potable water sources, wastewater streams, industrial waste or effluents, natural water sources, soil, airborne sources, pandemic or epidemic populations, epidemiological samples, research materials, pathology specimens, suspected bioterrorism agents, crime scene evidence, and the like.

As used herein, the term "patient" (also interchangeably referred to as "host" or "subject") refers to any host that can serve as a source of one or more of the biological samples or specimens as discussed herein. In certain aspects, the donor will be a vertebrate animal, which is intended to denote any animal species (and preferably, a mammalian species such as a human being). In certain embodiments, a "patient" refers to any animal host, including but not limited to, human and non-human primates, avians, reptiles, amphibians, bovines, canines, caprines, cavines, corvines, epines, equines, felines, hircines, lapines, leporines, lupines, murines, ovines, porcines, racines, vulpines, and the like, including, without limitation, domesticated livestock, herding or migratory animals or birds, exotics or zoological specimens, as well as companion animals, pets, and any animal under the care of a veterinary practitioner. The invention may also be used to monitor disease outbreak, progression, and epidemiological statistics for a variety of global populations, including, without limitation, wasting disease in ungulates, tuberculosis, ebola, SARS, and avian influenzas. In certain embodiments, the samples will preferably be of mammalian origin, and more preferably of human origin.

The term "chaotrope" or "chaotropic agent" as used herein, includes substances that cause disorder in a protein or nucleic acid by, for example, but not limited to, altering the secondary, tertiary, or quaternary structure of a protein or a nucleic acid while leaving the primary structure intact.

The term "e.g.," as used herein, is used merely by way of example, without limitation intended, and should not be construed as referring only those items explicitly enumerated in the specification.

The term "substantially free" or "essentially free," as used herein, typically means that a composition contains less than about 10 weight percent, preferably less than about 5 weight percent, and more preferably less than about 1 weight percent of a compound. In a preferred embodiment, these terms refer to less than about 0.5 weight percent, more preferably less than about 0.1 weight percent or even less than about 0.01 weight percent. The terms encompass a composition being entirely free of a compound or other stated property, as well. With respect to degradation or deterioration, the term "substantial" may also refer to the above-noted weight percentages, such that preventing substantial degradation would refer to less than about 15 weight percent, less than about 10 weight percent, preferably less than about 5 weight percent, etc., being lost to degradation. In other embodiments, these terms refer to mere percentages rather than weight percentages, such as with respect to the term "substantially non-pathogenic" where the term "substantially" refers to leaving less than about 10 percent, less than about 5 percent, etc., of the pathogenic activity.

As used herein, the term "heterologous" is defined in relation to a predetermined referenced nucleic acid sequence. For example, with respect to a structural gene sequence, a heterologous promoter is defined as a promoter that does not naturally occur adjacent to the referenced structural gene, but which is positioned by the hand of man in one or more laboratory manipulations that are routinely employed by those of ordinary skill in the molecular biological arts. Likewise, a heterologous gene or nucleic acid segment is defined as a gene or nucleic acid segment that does not naturally occur adjacent to the referenced sequence, promoter and/or enhancer element(s), etc.

As used herein, the term "homology" refers to a degree of complementarity between two or more polynucleotide or polypeptide sequences. The word "identity" may substitute for the word "homology" when a first nucleic acid or amino acid sequence has the exact same primary sequence as a second nucleic acid or amino acid sequence. Sequence homology and sequence identity can be determined by analyzing two or more sequences using algorithms and computer programs known in the art. Such methods may be used to assess whether a given sequence is identical or homologous to another selected sequence.

As used herein, "homologous" means, when referring to polynucleotides, sequences that have the same essential nucleotide sequence, despite arising from different origins. Typically, homologous nucleic acid sequences are derived from closely related genes or organisms possessing one or more substantially similar genomic sequences. By contrast, an "analogous" polynucleotide is one that shares the same function with a polynucleotide from a different species or organism, but may have a significantly different primary nucleotide sequence that encodes one or more proteins or polypeptides that accomplish similar functions or possess similar biological activity. Analogous polynucleotides may often be derived from two or more organisms that are not closely related (e.g., either genetically or phylogenetically).

The terms "identical" or percent "identity," in the context of two or more nucleic acid or polynucleotide sequences, refer to two or more sequences or subsequences that are the same or have a specified percentage of nucleotides that are the same, when compared and aligned for maximum correspondence over a comparison window, as measured using a sequence comparison algorithm or by manual alignment and visual inspection.

A "primer" or "primer sequence" may include any nucleic acid sequence or segment that selectively hybridizes to a complementary template nucleic acid strand ("target sequence") and functions as an initiation point for the addition of nucleotides to replicate the template strand. Primer sequences of the present invention may be labeled or contain other modifications which allow the detection and/or analysis of amplification products. In addition to serving as initiators for polymerase-mediated duplication of target DNA sequences, primer sequences may also be used for the reverse transcription of template RNAs into corresponding DNAs.

A "target sequence" or "target nucleotide sequence" as used herein includes any nucleotide sequence to which one of said primer sequences hybridizes under conditions that allow an enzyme having polymerase activity to elongate the primer sequence, and thereby replicate the complementary strand.

As used herein, the term "operably linked" refers to a linkage of two or more polynucleotides or two or more nucleic acid sequences in a functional relationship. A nucleic acid is "operably linked" when it is placed into a functional relationship with another nucleic acid sequence. For instance, a promoter or enhancer is operably linked to a coding sequence if it affects the transcription of the coding sequence. "Operably linked" means that the nucleic acid sequences being linked are typically contiguous, or substantially contiguous, and, where necessary to join two protein coding regions, contiguous and in reading frame. Since enhancers generally function when separated from the promoter by several kilobases and intronic sequences may be of variable lengths; however, some polynucleotide elements may be operably linked but not contiguous.

"Transcriptional unit" refers to a polynucleotide sequence that comprises at least a first structural gene operably linked to at least a first cis-acting promoter sequence and optionally linked operably to one or more other cis-acting nucleic acid sequences necessary for efficient transcription of the structural gene sequences, and at least a first distal regulatory element as may be required for the appropriate tissue-specific and developmental transcription of the structural gene sequence operably positioned under the control of the promoter and/or enhancer elements, as well as any additional cis sequences that are necessary for efficient transcription and translation (e.g., polyadenylation site(s), mRNA stability controlling sequence(s), etc.

The phrases "isolated" or "biologically pure" refer to material that is substantially, or essentially, free from components that normally accompany the material as it is found in its native state. Thus, isolated polynucleotides in accordance with the invention preferably do not contain materials normally associated with those polynucleotides in their natural, or in situ, environment.

"Link" or "join" refers to any method known in the art for functionally connecting one or more proteins, peptides, nucleic acids, or polynucleotides, including, without limitation, recombinant fusion, covalent bonding, disulfide bonding, ionic bonding, hydrogen bonding, electrostatic bonding, and the like.

The term "pathogen" is defined herein as any sort of infectious agent, including e.g., viruses, prions, protozoans, parasites, as well as microbes such as bacteria, yeast, molds, fungi, and the like.

As used herein, the term "plasmid" refers to a genetic construct that is composed of genetic material (i.e., nucleic acids). Typically, a plasmid contains an origin of replication that is functional in bacterial host cells, e.g., *Escherichia coli*, and selectable markers for detecting bacterial host cells comprising the plasmid. Plasmids of the present invention may include genetic elements as described herein arranged such that an inserted coding sequence can be transcribed and translated in eukaryotic cells. In addition, the plasmid may include one or more nucleic acids derived from natural or artificial sources.

As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues described herein are preferred to be in the "L" isomeric form. However, residues in the "D" isomeric form may be substituted for any L-amino acid residue provided the desired properties of the polypeptide are retained.

"Protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is preferably intended to refer to all amino acid chain lengths, including those of short peptides of from about 2 to about 20 amino acid residues in length, oligopeptides of from about 10 to about 100 amino acid residues in length, and polypeptides including about 100 amino acid residues or more in length. The term "sequence," when referring to amino acids, relates to all or a portion of the linear N-terminal to C-terminal order of amino acids within a given amino acid chain, e.g., polypeptide or protein; "subsequence" means any consecutive stretch of amino acids within a sequence, e.g., at least 3 consecutive amino acids within a given protein or polypeptide sequence. With reference to nucleotide and polynucleotide chains, "sequence" and "subsequence" have similar meanings relating to the 5' to 3' order of nucleotides.

As used herein, the term "substantially homologous" encompasses two or more biomolecular sequences that are significantly similar to each other at the primary nucleotide sequence level. For example, in the context of two or more nucleic acid sequences, "substantially homologous" can refer to at least about 75%, preferably at least about 80%, and more preferably at least about 85% or at least about 90% identity, and even more preferably at least about 95%, more preferably at least about 97% identical, more preferably at least about 98% identical, more preferably at least about 99% identical, and even more preferably still, at least substantially or entirely 100% identical (i.e., "invariant").

Likewise, as used herein, the term "substantially identical" encompasses two or more biomolecular sequences (and in particular polynucleotide sequences) that exhibit a high degree of identity to each other at the nucleotide level. For example, in the context of two or more nucleic acid sequences, "substantially identical" can refer to sequences that at least about 80%, and more preferably at least about 85% or at least about 90% identical to each other, and even more preferably at least about 95%, more preferably at least about 97% identical, more preferably at least about 98% identical, more preferably at least about 99% identical, and even more preferably still, at least substantially or entirely 100% identical (i.e., "non-degenerate").

The term "recombinant" indicates that the material (e.g., a polynucleotide or a polypeptide) has been artificially or synthetically (non-naturally) altered by human intervention. The alteration can be performed on the material within or removed from, its natural environment or state. Specifically, e.g., a promoter sequence is "recombinant" when it is produced by the expression of a nucleic acid segment engineered by the hand of man. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus," e.g., a recombinant influenza virus, is produced by the expression of a recombinant nucleic acid.

In accordance with the present invention, polynucleotides, nucleic acid segments, nucleic acid sequences, and the like, include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from natural sources, chemically synthesized, modified, or otherwise prepared or synthesized in whole or in part by the hand of man.

Likewise, in accordance with long standing patent law convention, the words "a" and "an" when used in this application, including the claims, denotes "one or more."

EXAMPLES

The following examples are included to demonstrate illustrative embodiments of the invention. It should be appreciated by those of ordinary skill in the art that the techniques disclosed in the examples that follow represent techniques discovered to function well in the practice of the invention, and thus can be considered to constitute preferred modes for its practice. However, those of ordinary skill in the art should, in light of the present disclosure, appreciate that many changes can be made in the specific embodiments which are disclosed and still obtain a like or similar result without departing from the spirit and scope of the invention.

Example 1

Formulation of Exemplary Storage Solutions

The present example provides a general formulation of the PSS (PanFlu) compositions of the present invention. Additional formulations of the PSS compositions are also exemplified in Example 2 through Example 5.

Materials

Guanidine thiocyanate, sodium citrate, Antifoam A® Concentrate, and N-lauroylsarcosine, sodium salt, were all purchased from Sigma Chemical Co. (St. Louis, Mo., USA). Tris(2-carboxyethyl) phosphine hydrochloride (TCEP) was obtained from Soltec Ventures Inc. (Beverly, Mass., USA). 2-amino-2-hydroxymethyl-propane-1,3-diol (TRIS) was obtained from Applied Biosystems/Ambion (Austin, Tex., USA). 2-[2-(Bis(carboxymethyl)amino)ethyl-(carboxymethyl)amino]acetic acid (EDTA) GIBCO® Ultra Pure was obtained from Invitrogen Corp. (Carlsbad, Calif., USA). All other reagents are available commercially from Sigma-Aldrich or USB Corporation.

TABLE 1

FORMULATION RANGES OF EXEMPLARY COMPONENTS FOR THE PREPARATION OF PRIMESTORE ™ COMPOSITIONS

| Compound | Final Concentration Range |
| --- | --- |
| 1. A chaotrope, e.g.: | |
| Guanidine thiocyanate | about 0.5M to about 6M |
| or Guanidine hydrochloride | about 0.5M to about 6M |
| or Guanidine isocyanate | about 0.5M to about 6M |
| 2. An anionic detergent, e.g.: | |
| N-lauroyl sarcosine (inter alia Na salt) | about 0.15% to about 1% (wt./vol.) |
| or Sodium dodecyl sulfate, | same |
| Lithium dodecyl sulfate, | same |
| Sodium glycocholate, | same |
| Sodium deoxycholate, | same |
| Sodium taurodeoxycholate, or | same |
| Sodium cholate | about 0.1% to about 1% (wt./vol.) |
| 3. A reducing agent, e.g.: | |
| TCEP | about 0.5 mM to about 30 mM |
| or β-ME, DTT, formamide, or DMSO | about 0.05M to about 0.3M |
| 4. A chelator, e.g.: | |
| Sodium citrate | about 0.5 mM to about 50 mM |
| or EGTA, HEDTA, DTPA, NTA, APCA, etc. | about 0.01 mM to about 1 mM |
| 5. A buffer (e.g., TRIS, HEPES, Bis-Tris, etc.) | about 1 mM to about 1M |
| 6. An acid (e.g., HCl or citric acid) | q.s. to adjust to a pH of about 6 to 7, preferably 6.4 to 6.8 |
| 7. Nuclease-free water | q.s. to desired final volume |
| Optionally one or more of: | |
| 8. A surfactant/defoaming agent, e.g.: | |
| Antifoam A ® or Tween ® | about 0.0001% to about 0.3% (wt./vol.) |
| 9. An alkanol (e.g., methanol, ethanol, propanol, etc.) | about 1% to about 25% (vol./vol.) |
| 10. carrier/IPC RNA or DNA | about 1 pg to about 1 µg/mL |

Example 2

Formulation of an Exemplary Storage Solution

The present example describes a first exemplary formulation of the compositions of the invention. This formulation has also been alternatively referred to by the inventors as "PrimeStore™ Solution" or "PSS" version 1.

TABLE 2

PREPARATION OF PRIMESTORE ™ COMPOSITION (VER. 1)

| Compound | Final Concentration |
| --- | --- |
| Guanidine thiocyanate | 4M |
| Sodium citrate | 30 mM |
| Sodium dodecyl sulfate | 0.25% (wt./vol.) |
| N-lauroyl sarcosine, sodium salt | 0.25% (wt./vol.) |
| 2-mercaptoethanol (β-ME) | 0.1M |
| Antifoam A | 0.1% (wt/vol.) |

TABLE 2-continued

PREPARATION OF PRIMESTORE ™ COMPOSITION (VER. 1)

| Compound | Final Concentration |
| --- | --- |
| Citric acid | q.s. to adjust pH to 6.5 |
| Nuclease-free water | 11.82 mL |

Example 3

Preparation of a Second Exemplary Storage Solution

The present example describes the preparation of another exemplary storage solution according to the present invention. This formulation has also been alternatively referred to by the inventors as PrimeStore™ version 2.

TABLE 3

PREPARATION OF PRIMESTORE ™ COMPOSITION (VER. 2)

| Compound | Quantity | Final Concentration |
| --- | --- | --- |
| Guanidine thiocyanate | 35.488 gm | 3M |
| TCEP | 0.02867 gm | 1 mM |
| Sodium citrate | 0.2931 gm | 10 mM |
| N-lauroyl sarcosine, sodium salt (NLS) | 0.5 gm | 0.5% |
| Antifoam A (10% solution) | 200 µL | 0.002% |
| TRIS (1M) | 10 mL | 100 mM |
| EDTA (0.5M) | 20 µL | 0.1 mM |
| Hydrochloric acid (HCl) | q.s. to adjust pH to 6.7 | — |
| Nuclease-free water | q.s. to 100 mL | — |

Example 4

Preparation of a Third Exemplary Storage Solution

The present example describes the preparation of another exemplary storage solution according to the present invention. This formulation has also been alternatively referred to by the inventors as PSS version 2.2.

TABLE 4

PREPARATION OF PRIMESTORE ™ COMPOSITION (VER. 2.2)

| Compound | Quantity | Concentration |
|---|---|---|
| Guanidine thiocyanate | 35.488 gm | 2.5M |
| TCEP | 0.02867 gm | 0.5 mM |
| Sodium citrate | 0.2931 gm | 10 mM |
| N-lauroyl sarcosine, sodium salt (NLS) | 0.5 gm | 0.4% |
| Antifoam A (10% solution) | 200 µL | 0.002% |
| TRIS (1M) | 10 mL | 100 mM |
| EDTA (0.5M) | 20 µL | 0.1 mM |
| Ethanol, molecular grade (96-100%) | 23 mL | 23% (vol./vol.) |
| Hydrochloric acid (HCl) | q.s. to adjust pH to 6.7 | — |
| Nuclease-free water | q.s. to 100 mL | — |

Exemplary Protocol for the Preparation of PSS (Ver. 2.2):
1. Add 40 mL of nuclease-free water to a clean beaker with a stir bar.
2. Place beaker on a hot plate/stirrer and adjust temperature to 60-65° C. Set stirring speed to medium.
3. Add 35.488 gm of guanidine thiocyanate slowly to the water allowing it to dissolve as added.
4. Add 0.0287 gm of TCEP to beaker and increase stirrer speed to help dissolve crystals.
5. Add 0.2931 gm of sodium citrate to the beaker.
6. Add 0.5 gm of NLS to the solution. Increase stirrer speed to create a vortex in the beaker. This will pull the NLS into the solution and help dissolve the reagent.
7. Vortex a prepared 10% Antifoam A solution (1 mL Antifoam A Concentrate+9 mL nuclease-free water). Pipette 200 µL of the 10% Antifoam A into the solution.
8. Pipette 10 mL of 1 M TRIS into the solution.
9. Pipette 20 gL of 0.5 M EDTA into the solution.
10. Increase the temperature to bring the solution to 75-80° C. and stir for 3-5 minutes.
11. Remove beaker from heat and allow solution to cool to room temperature (≈22-25° C.).
12. Add 23 mL of ethanol to the solution and mix thoroughly.
13. Adjust pH to 6.9 with HCl.
14. Pour solution into a clean 100 mL graduated cylinder.
15. Add nuclease-free water to bring total volume to 100 mL.
16. Transfer solution to a labeled sterile container. Store at room temperature (≈22-25° C.).

*Note: Preferably, make sure each reagent is completely dissolved before adding the next.

Example 5

Comparison of PrimeStore™ Solution to Conventional Formulations

A sample of homogenized nasal tissue from a cotton rat (Sigmodon hispidus) challenged with influenza A (H3N2) or a human clinical influenza A (H1N1) sample collected as a human clinical nasal wash during the 2006-07 season were placed in PSS (ver. 1) and tested compared to the respective lysis formulation and protocol, and extraction procedure, from three commercially available kits: RNAqueous®-Micro (Ambion, Austin, Tex., USA), QIAamp Viral RNA Mini Kit (Catalogue #52904, Qiagen, Valencia, Calif., USA), and MagMax AI/ND Viral RNA Isolation Kit (Catalogue #AM1929, Ambion). Extraction efficiency was evaluated using the ABI 7500 sequence detection system with the comparative $C_T$ method (see FIG. 2).

Figure 1:
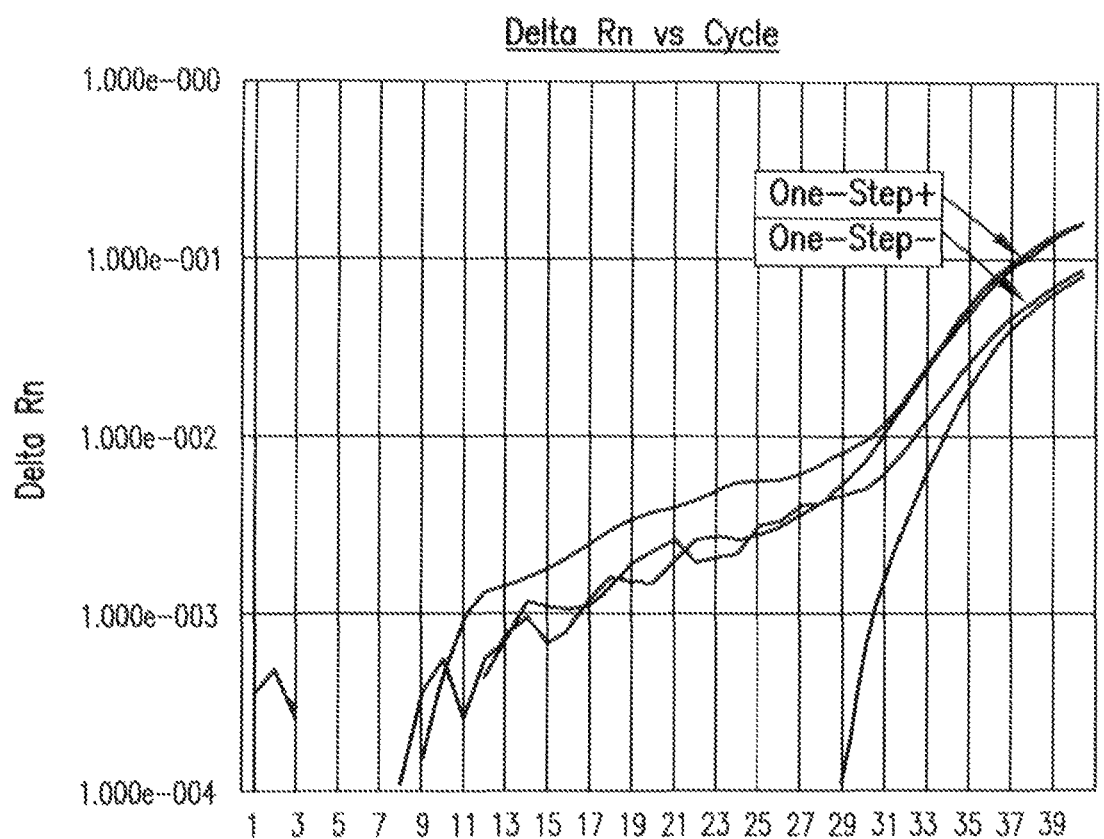
FIG. 1 shows the extraction efficiency of PSS (ver. 1). PSS (ver. 1 [depicted here as "One-step+"]) compared to the lysis solution provided in the RNAqueous®-Micro Kit (Ambion, Catalog #AM1931) using a standard amount of whole influenza A virus. For the comparison, either the one-step formulation or the lysis solution provided in the RNAqueous-Micro Kit was used for viral RNA lyses and then extracted according to manufacturer protocols. Replicate reactions were processed and analyzed by qRT-PCR using, for example, the Applied Biosystems ABI7500 sequence detection system (Life Technologies Corporation, Carlsbad, Calif., USA)
Figure 4A:
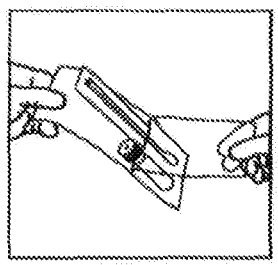
Figure 4B:
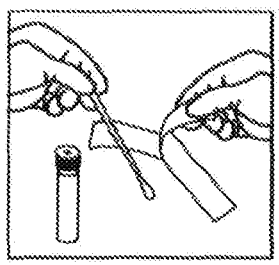
Figure 4C:
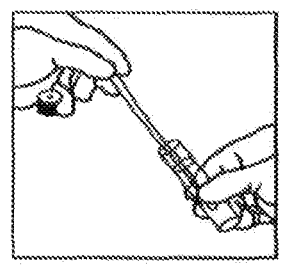
Figure 4D:
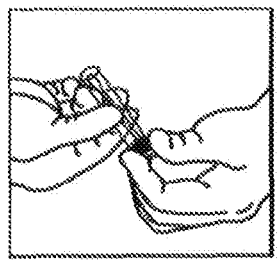
Figure 4E:
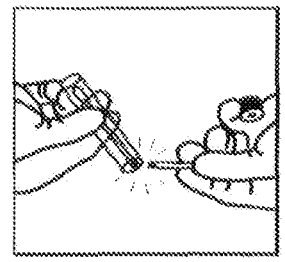

In FIG. 2, "delta Rn" represents the fluorescent reporter signal minus a baseline amount. As shown in FIG. 1 and FIG. 2, the relative $C_T$ scores and viral copies detected were optimal when the fixing formulation was used in place of the respective conventional lysis buffer for each commercial kit. In these two sample types, the compositions of the invention worked better than the two conventional Kits for extraction purposes. The PrimeStore™ Solution (ver. 1) composition was also shown to be readily compatible with commercially available nucleic acid extraction kits. FIG. 1 illustrates RNA extraction results where the version 1 of PSS was used in conjunction with three commercially available kits: Qiagen Viral Mini, Ambion RNAqueous Mini, and Ambion A1/NCD MagMax. As illustrated by FIG. 1, when the lysis buffer of the extraction kit was replaced with the fixing formulation (denoted on the figure as "One-Step+), superior nucleic acid extraction was achieved when compared to extraction using kits according to standard protocol (denoted on the figure as "One-Step-". Extraction efficiency was measured by real time (r) reverse transcription (RT) polymerase chain reaction (PCR) [rRT-PCR].

FIG. 3 shows preservation of naked RNA in PrimeStore™ Solution compared to preservation in a prior solution, with water used as a control. As illustrated in FIG. 3, detection (by fluorescence) occurred at the earliest amplification cycle for RNA stored in PSS (ver. 1) at all time-points assayed.

Example 6

PrimeStore™ Solution for the Collection of Nasal Wash Specimens

A prospective clinical detection study was conducted using nasal wash specimens from: 1) symptomatic pediatric patients and 2) asymptomatic or symptomatic family members. Detection of influenza virus compared nasal wash specimens collected in PrimeStore™ Solution and VTM by qRT-PCR and traditional culture, respectively. Genetic characterization of influenza genes encoding hemagglutinin (HA), neuraminidase (NA), and matrix surface (MA) proteins were performed using select nasal wash specimens preserved in PrimeStore™ Solution to evaluate vaccine effectiveness and drug sensitivity within viral strains.

Influenza is a highly evolving, RNA-based respiratory virus responsible for more than 200,000 hospitalizations and about 36,000 fatalities each year in the United States. Widespread emergence of influenza drift variants among contemporary circulating human viruses prompted a change in all three-vaccine components for the upcoming 2008/09 season. Increased morbidity and mortality during the 2007/08 season included 72 influenza-associated pediatric deaths and continued drug resistance (oseltamivir [TamiFlu®, Roche Laboratories, Inc., Nutley, N.J., USA] and adamantadine) within circulating strains.

Materials and Methods

A total of 100 pediatric (index) patients who met the clinical case criteria for influenza infection and 126 family contacts were enrolled in the study. Nasal washings were placed into PrimeStore™ Solution and Universal VTM and analyzed by rRT-PCR or culture analysis, respectively. rRT-PCR was performed using influenza type (A or B) and subtype (H3, H1, H5) specific primers/probes according to Daum et al. (2007). Further genetic characterization of selected clinical samples preserved in PSS was performed using standard RT-PCR and direct nucleotide sequencing of the hemagglutinin HA, NA, and MA viral proteins.

Results

Of the total samples evaluated (N=226; 100 index, 126 family contacts), 66 (29%) tested positive for influenza virus (45 $H_3N_2$, 2 H1N1 and 19 B) by rRT-PCR. rRT-PCR from nasal washings preserved in PSS detected influenza virus from 11 patients (9 Flu A and 2 Flu B) that were not detected by culture (Table 5 and Table 6). Of these 11 specimens, five were from patients enrolled as family contacts.

Phylogenetic analysis of influenza A and B HA genes exhibited drifting compared to the 2007/08 vaccine strains and revealed a higher genetic homology to the 2008/09 Brisbane vaccine strains. Some genetic differences in viruses were noted among family members, particularly among influenza A (H3N2) strains. MA analysis revealed adamantane resistance in all influenza A H3N2 strains, but sensitivity in both H1N1 viruses. All influenza B strains (n=18) were sensitive to the neuraminidase inhibitor drugs zanamivir (Relenza® GlaxoSmithKline, Research Triangle Park, N.C., USA) and oseltamivir (Tamiflu® Roche) based on the presence of an aspartic acid (D) at amino acid 197 (influenza B numbering) in the NA gene.

qRT-Pcr vs. Traditional Culture Culture Methods qRT-PCR is superior to traditional culture for the detection of influenza virus from original nasal wash specimens preserved in PSS: influenza was detected within 2 hours (c.f 2 to 7 days for conventional culture methods); and the analyses were more sensitive (11 specimens; 9 Flu A and 2 Flu B detected below culture limits). Moreover, the use of molecular diagnostic methods in lieu of conventional organism culture did not propagate potentially infectious viruses, and simultaneously provided the type and subtype of the influenza virus.

Genetic Analysis

Vaccine Relatedness

H3N2 Strains: Analysis of the HA1 gene of the influenza A (H3N2) hemagglutinin (HA) revealed genetic drift including five amino acid differences in all Texas strains compared to the 2007-08 A/Wisconzin/67/2005 vaccine strain. One HA1 mutation noted in all Texas strains (D122N) was a potential glycosylation site. All A/Texas (H3N2) strains exhibited a greater HA homology (99.0-99.7%) to the newly selected 2008-09 A/Brisbane/10/2007 strain.

H1N1 Strains: The hemagglutinin HA1 gene of the 2 influenza A (H1N1) exhibited 7 amino acid changes compared to A/Solomon Island/3/2006 vaccine strain. Four substitutions (R90K, T145V, K210T and E290K) were within known H1 antibody combining sites. Both Texas H1N1 strains exhibited greater HA homology (98.8% and 99.4%) to the newly selected 2008-09 A/Brisbane/59/2007 vaccine strain.

Influenza B strains: Analysis of the HA1. hemagglutinin and neuraminidase genes revealed all Texas strains were of the B/Yamagata lineage and genetically more homologous to the 2008-09 B/Brisbane/5/2007 vaccine strain than the 2007/08 B/Malaysia/2506/2004 vaccine strain.

Family Mutation

Amino acid changes were noted in the NA, HA1, M1 and M2e among family members. The HA1 Hemagglutinin showed the highest mutation of the influenza genes analyzed, with one family exhibiting five amino acid changes.

Analysis of the highly conserved 24 amino acid M2e viral surface proton pump showed some variation within families. One index patient strain contained 3 unique amino acid M2e substitutions that were 'wild-type' within family member strains.

Antiviral Susceptibility

Adamantane: Matrix gene (MA) genetic analysis, specifically a serine-to-asparagine substitution at position 31 (S31N), revealed adamantane resistance in all influenza A (H3N2) strains but sensitivity in both influenza A (H1N1) viruses.

Neuraminidase Inhibitors: All Texas influenza A (H3N2) isolates were shown to be sensitive to oseltamivir through genetic analysis of E119V, R292K, and N294S substitutions in the NA gene. Genetic analysis of the influenza B NA gene revealed that all Texas strains contained an aspartic acid (D) residue at position 197, and are thus likely sensitive to oseltamivir.

The protocols and tests herein can be adapted for other microbes like tuberculosis, malaria, *staphylococcus*, and the like and other pathogens where there is a need to know antimicrobial susceptibility quickly.

Example 7

Influenza Sample Collection Using PrimeStore™ Solutions

The compositions of the present invention provide a single sample collection, transport, and storage reagent that facilitate: 1) procuring high quality nucleic acids from clinical or environmental specimens, 2) inactivation of potentially infectious biological pathogens for safe handling and transport of specimens, and 3) stabilization and preservation of released 'naked' RNA/DNA preventing hydrolysis/nuclease degradation for prolonged periods at ambient temperatures. The results of one such study are presented in the following example. This example illustrates the effectiveness of PSS (ver. 2.2) in killing pathogenic microbe(s).

TABLE 5

Influenza Subtype Detection: rRT-PCR vs. Culture

| | Influenza A | | | Influenza B | | |
| --- | --- | --- | --- | --- | --- | --- |
| Total Flu A Samples (N = 47) | rRT-PCR (N = 47) | Culture (N = 40) | rRT-PCR (N = 19) | Culture (N = 17) | Total Flu B Samples (N = 19) |
| Index Patients (28) | 28/28 (100%) | 23/28 (82%) | 16/16 (100%) | 14/16 (88%) | Index Patients ('6) |
| Family Contacts (19) | 19/19 (100%) | 15/19 (79%) | 3/3 (100%) | 3/3 (100%) | Family Contacts (3) |

TABLE 6

Positive Influenza Detection: rRT-PCR vs. Culture

| Total Samples (N = 226) | Flu Positive (N = 66) | rRT-PCR (N = 66) | Culture (N = 66) |
|---|---|---|---|
| Index Patients (100) | 44/100 | 39/39 (100%) | 37/39 (94%) |
| Family Contacts (126) | 22/126 | 27/27 (100%) | 18/27 (67%) |

Methods qRT-PCR was used to assay influenza A (H5N1) virus nucleic acid preserved in PrimeStore™ Solution. A time-course study at room temperature was carried out to evaluate the integrity of clinical specimens, cloacal samples, and cloned template avian influenza A virus (H5) RNA stored and extracted from PSS, VTM, RNA storage solution, or nuclease-free water. PrimeStore™ Solution extraction efficiency was compared to three commercially available nucleic acid extraction kits. Furthermore, the ability of RNA contained in PSS to resist nuclease degradation was evaluated.

Results

PSS (ver. 2, but lacking ethanol) inactivated microbial agents while preserving released RNA/DNA from clinical material, i.e., nasal washes, throat swabs, or environmental samples. Clinical specimens or environmental samples placed in this solution were stabilized at room temperature for up to 30 days while degradation of nucleic acids occurred in other transport media. PSS is compatible with commercially available RNA isolation kits and produced an increased nucleic acid yield.

Example 8

Killing of MRSA (ATCC33592) in PrimeStore™ Solution

This example illustrates the effectiveness of PSS (ver. 2.2) in killing a bacterial pathogen. Methicillin-resistant *Staphylococcus aureus* (MRSA) strain ATCC33592 was diluted 10-fold and 1000-fold into PSS (ver. 2.2) and quantitated (see FIG. 6).

Experimental Protocol

Day Procedure

0 Transfer MRSA (ATCC33592) from a Culti-loop® (Remel) to 1.5 mL of TSB in a 15-ml conical test tube. Incubate at 37° C. for approximately 15 min. Gently vortex suspension and transfer 100 μL to a blood-agar plate. Incubate the plate overnight at 37° C.

1 Observe heavy and uniform colony growth after 12 hr incubation. Transfer ~10% of colonies to 300 mL of tryptic soy broth (TSB) in a sterile, 1-liter flask. Place flask on shaker at 37° C. and 200 rpm.

After approximately 4-6 hrs' incubation, transfer ~50 mL of bacterial suspension to new 1-liter flask containing 300 mL fresh TSB.

After approximately 4-6 hrs' incubation, transfer ~100 μL of culture into 900 μL of TSB (1:10 control dilution). From this suspension 10 μL were transferred to 990 μL of TSB (1:1000 control dilution).

Transfer 100 μL of culture into 900 μL of PrimeStore™ Solution (1:10 PSS dilution). From this suspension 10 μL were transferred to 990 μL of TSB (1:1000 PSS dilution).

Immediately after transfer into TSB or PrimeStore™ Solution (ver. 2.2), the suspensions were gently vortexed and 100 μL were plated from both dilutions of control and PrimeStore™ suspensions onto blood agar plates. The time-zero time point was actually about two minutes following addition of the bacteria to the TSB or PSS.

The suspensions in TSB and PSS (ver. 2.2) were kept at room temperature.

An additional 100 μL was plated onto blood agar plates at 5, 15, 30, 60, 120 and 240 minutes after the preparation of the suspensions in TSB and PSS.

Bacterial suspensions on the plates were allowed to dry, the plated inverted and the plates incubated overnight at 37° C.

A titration of the shaker culture was also performed by mixing 100 μL of the suspension from the shaker culture with 900 μL of TSB ($10^{-1}$ dilution). Serial 10-fold dilutions were prepared through $10^{-9}$. 100 μL samples were plated onto blood agar from all dilutions except $10^{-1}$.

2 Plates were observed for bacterial colonies. All plates were stored at 4° C. for later observation, if necessary.

Results

The results are presented in Table 7 and Table 8. Briefly, the bacterial suspension contained approximately $4.7\times10^9$ cfu/ml. Thus, the 1:10 dilution contained approximately $4.7\times10^8$ cfu/ml and the 1:1000 dilution contained $4.7\times10^6$ cfu/ml. At all time points, the bacteria suspended in TSB were too numerous to count. At all time points the bacteria suspended in PrimeStore™ Solution and plated onto blood agar plates had no detectable colonies.

TABLE 7

KILLING OF MRSA (ATCC 33592) BY PRIMESTORE ™ SOLUTION (VER. 2.2)

| Incubation Time | In TSB | | In Primestore | |
|---|---|---|---|---|
| (Minutes) | 1:10 | 1:1000 | 1:10 | 1:1000 |
| 0 | TNTC | TNTC | 0 | 0 |
| 5 | TNTC | TNTC | 0 | 0 |
| 15 | TNTC | TNTC | 0 | 0 |
| 30 | TNTC | TNTC | 0 | 0 |
| 60 | TNTC | TNTC | 0 | 0 |
| 120 | TNTC | TNTC | 0 | 0 |
| 240 | TNTC | TNTC | 0 | 0 |

TNTC = too numerous to count.

TABLE 8

TITRATION OF MRSA ATCC33592 FROM SUSPENSION CULTURE

| Dilution | CFU/plate | CFU/ml |
|---|---|---|
| 1.E+01 | TNTC | |
| 1.E+02 | TNTC | |
| 1.E+03 | TNTC | |
| 1.E+04 | TNTC | |
| 1.E+05 | TNTC | |
| 1.E+06 | TNTC | |
| 1.E+07 | 35 | 3.5 × 10^9 |
| 1.E+08 | 6 | 6 × 10^9 |
| 1.E+09 | 0 | |

NOTE:

CFU/ml calculations are corrected to include the plating volume of 0.1 mls

Final Conc: 4.7 × 10^9/ml

TNTC = too numerous to count.

CFU = colony forming units.

An additional study was performed to determine the time of exposure necessary for killing MRSA ATCC33592 when diluted 10-fold into PSS (Ver. 2.2), and to determine the effect of dilution of the bacteria after exposure to PSS, but before plating.

Experimental Protocol
Day Procedure
0 Transfer MRSA (ATCC33592) from TNTC plate from the study described above into 4 mL of TSB. These plates had been stored at 4° C. for approximately 48 hrs. Bacteria were vortexed gently and placed at room temperature for approximately 10 min. before use. 0.1 mL of bacterial suspension was transferred to 0.9 mL PSS and vortexed gently. After approximately 60 sec, the bacteria in PrimeStore™ were again vortexed gently and 0.1 mL of bacterial suspension was transferred into 0.3 mL of TSB (1:4 dilution). 100 µL of bacteria in PrimeStore™ Solution (designated "neat") and from the 1:4 dilution into TSB were plated onto blood agar plates (5% sheep RBCs in TSA). This process was repeated at 5 and 15 min., and then again with dilutions made into TSB instead of PrimeStore™ Solution. The liquid bacterial suspensions on the blood agar plates were allowed to dry at room temperature and then incubated overnight at 37° C.
1 After approximately 16 hrs' incubation, the plates were removed from the incubator and colonies counted.

Results

The bacterial suspension contained an unknown number of colony forming units (cfu) per mL. At all time points the bacteria suspended in tryptic soy broth (TSB) were too numerous to count (TNTC). At all time points, the bacteria suspended in PrimeStore™ compositions and plated onto blood agar plates produced no colonies (Table 9).

TABLE 9

KILLING OF MRSA (ATCC33592) BY PRIMESTORE ™ SOLUTION

| Incubation Time | In TSB | | In TSB | |
|---|---|---|---|---|
| (minutes) | neat | 1:4 | neat | 1:4 |
| 1 | TNTC | TNTC | 0 | 0 |
| 5 | TNTC | TNTC | 0 | 0 |
| 15 | TNTC | TNTC | 0 | 0 |

TNTC = too numerous to count.

Example 9

Additional Studies Evaluating PrimeStore™ Solutions

Figure 7A:
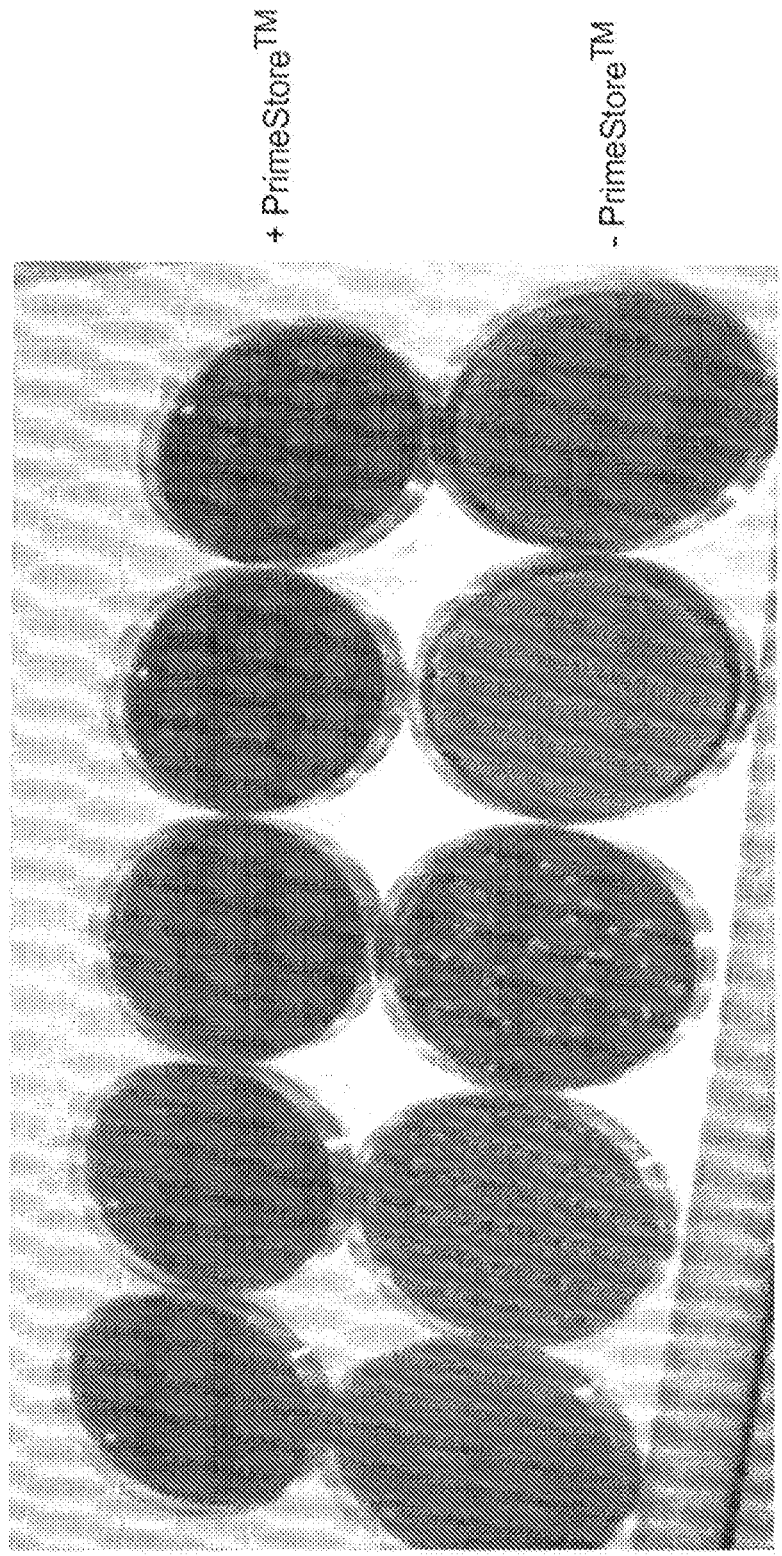
Figure 7B:
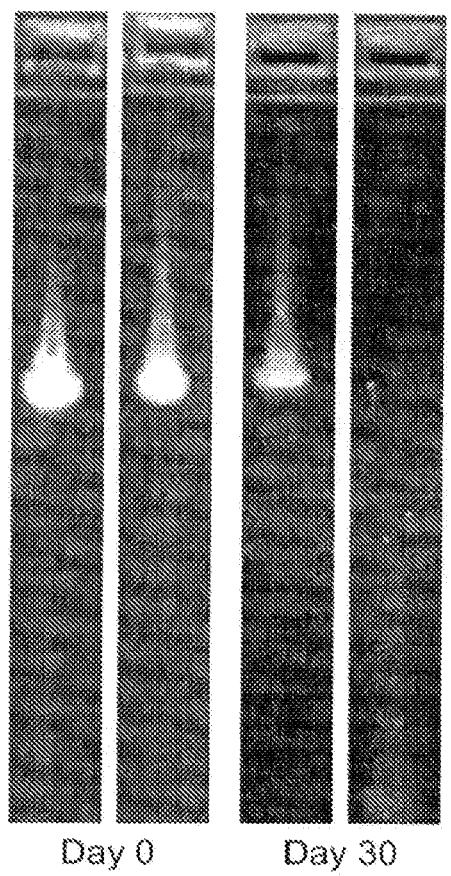
Figure 8A:
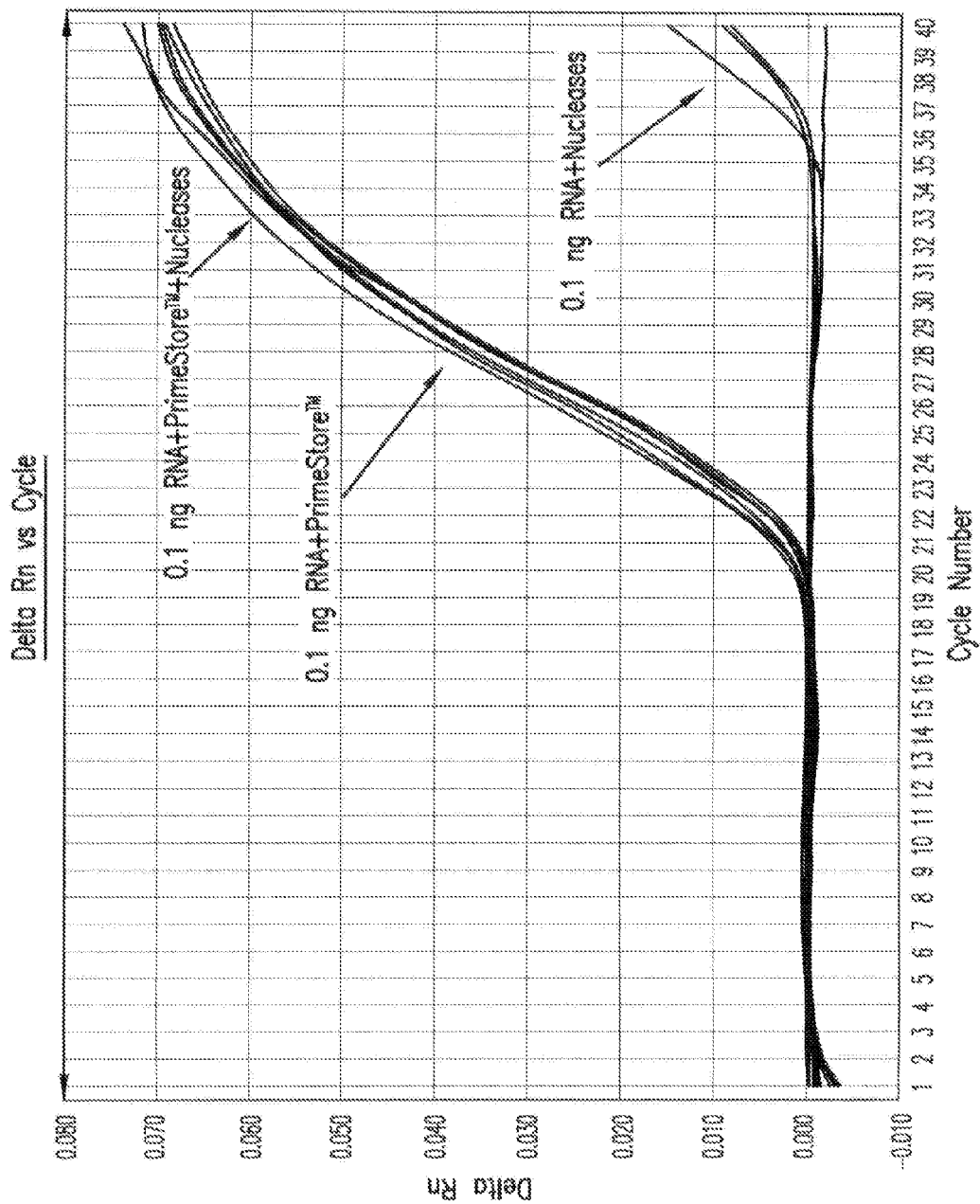
Figure 8B:
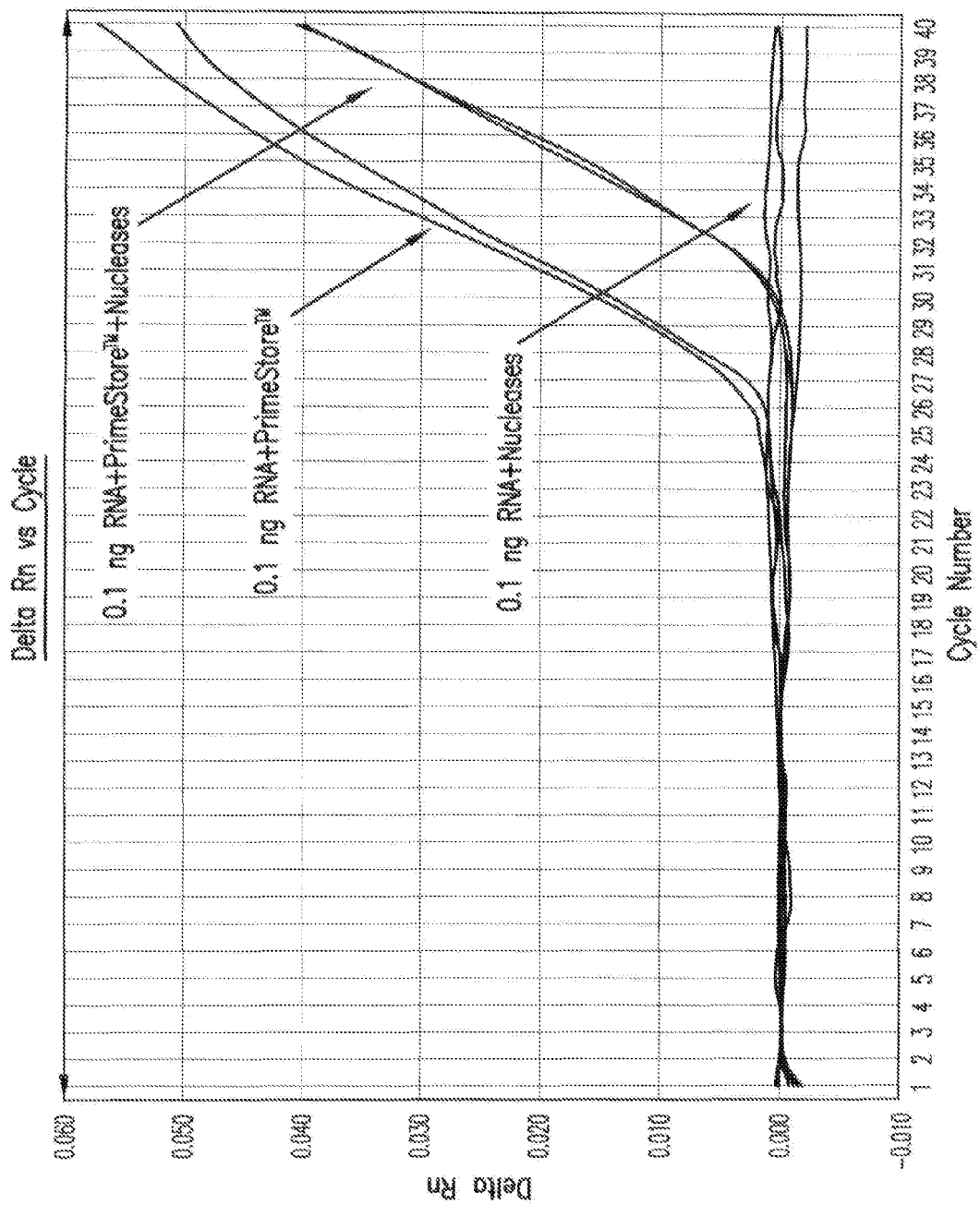
Figure 8C:
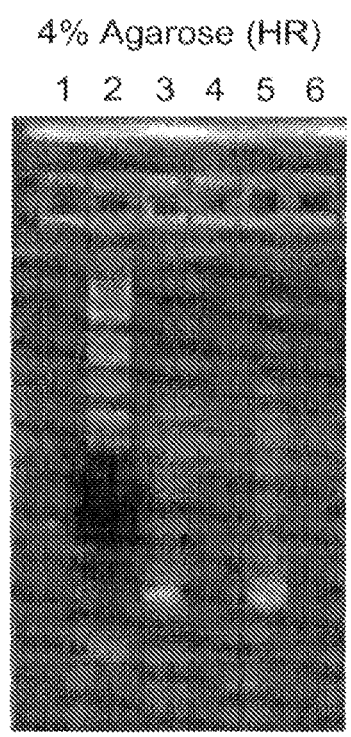
Figure 9:
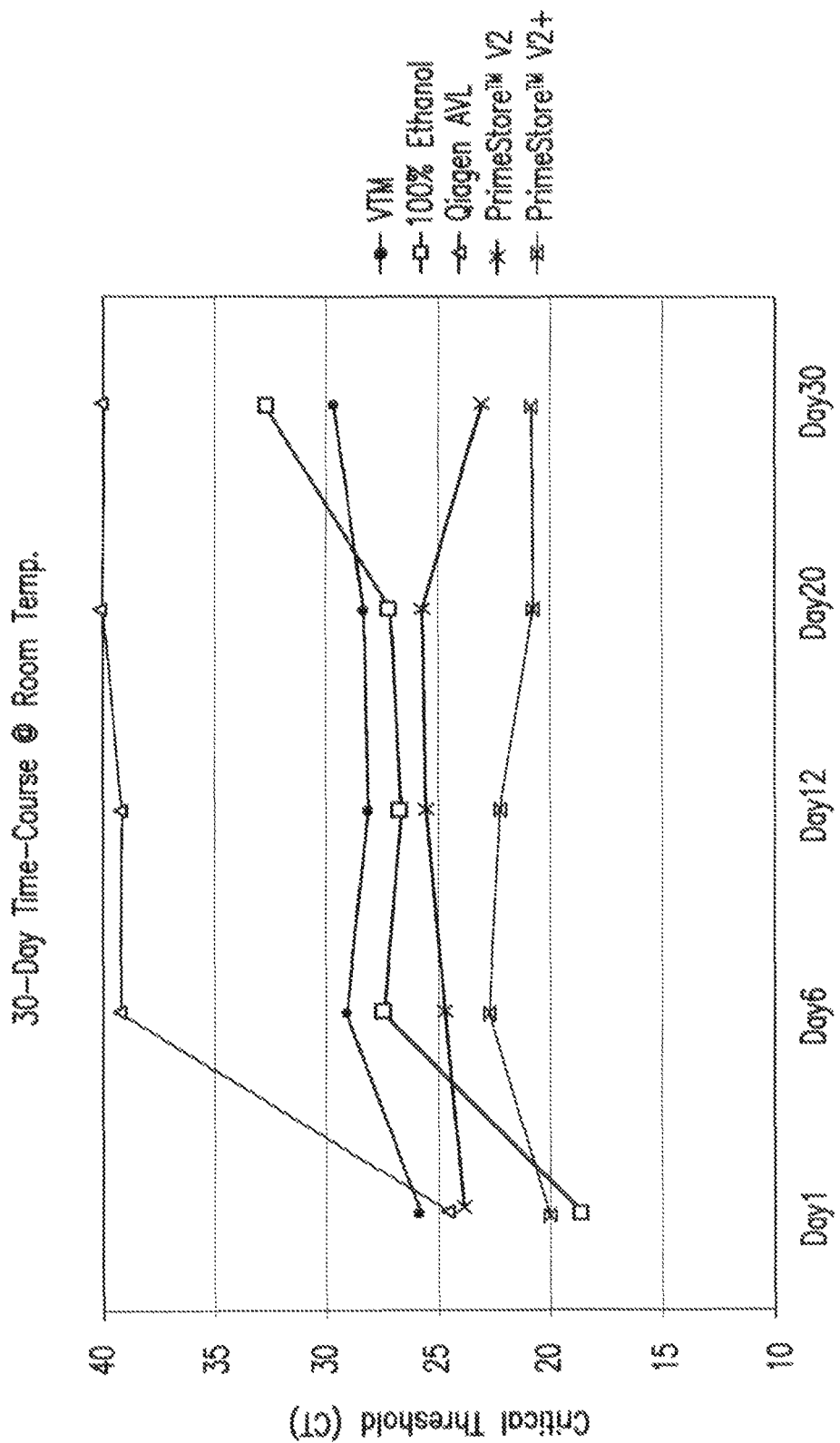
Figure 10:
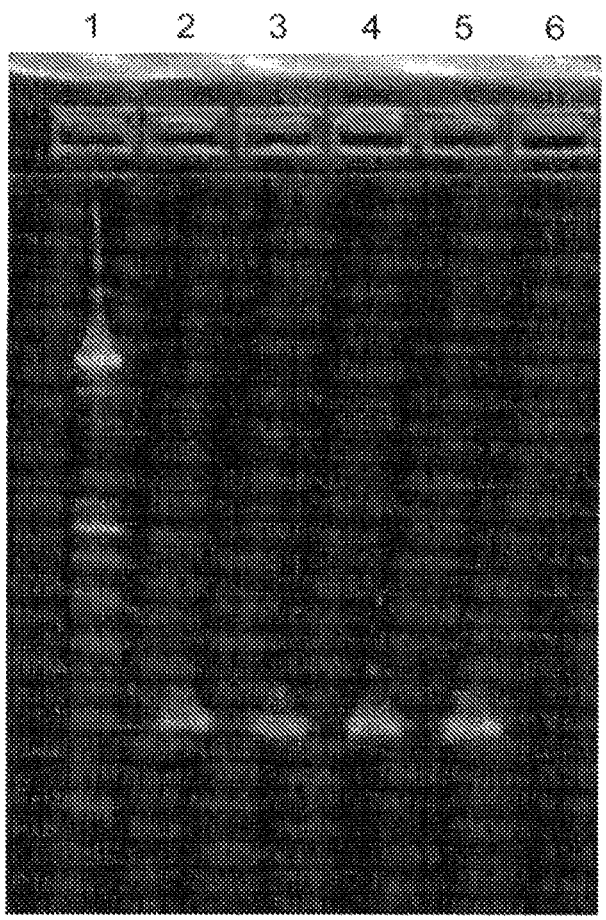
Figure 11:
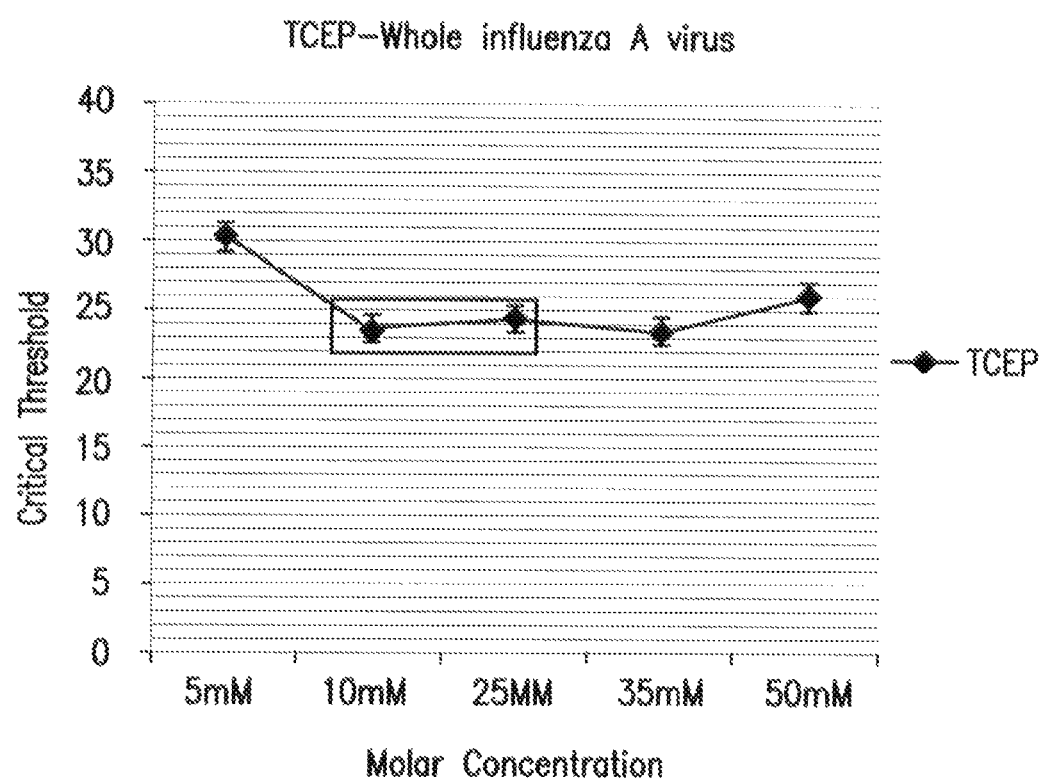
Figure 13A:
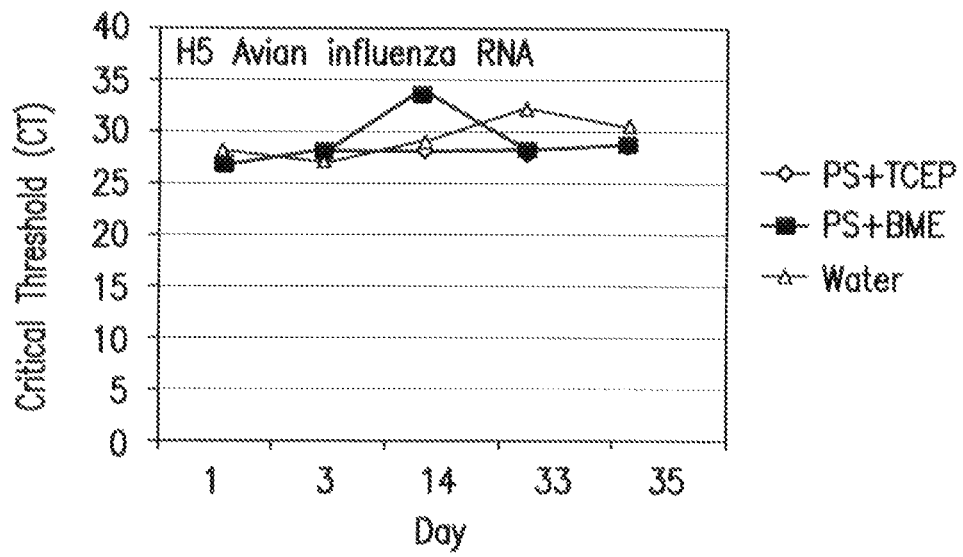
Figure 13B:
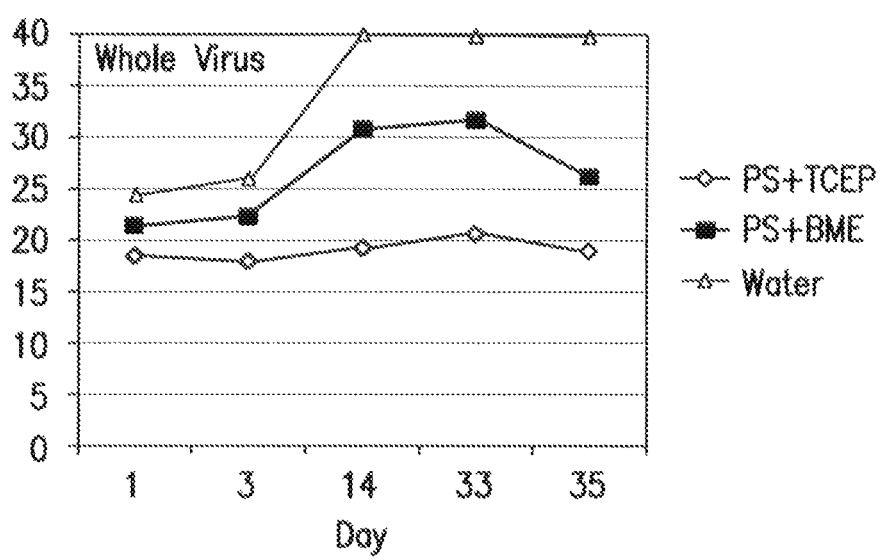
Figure 14A:
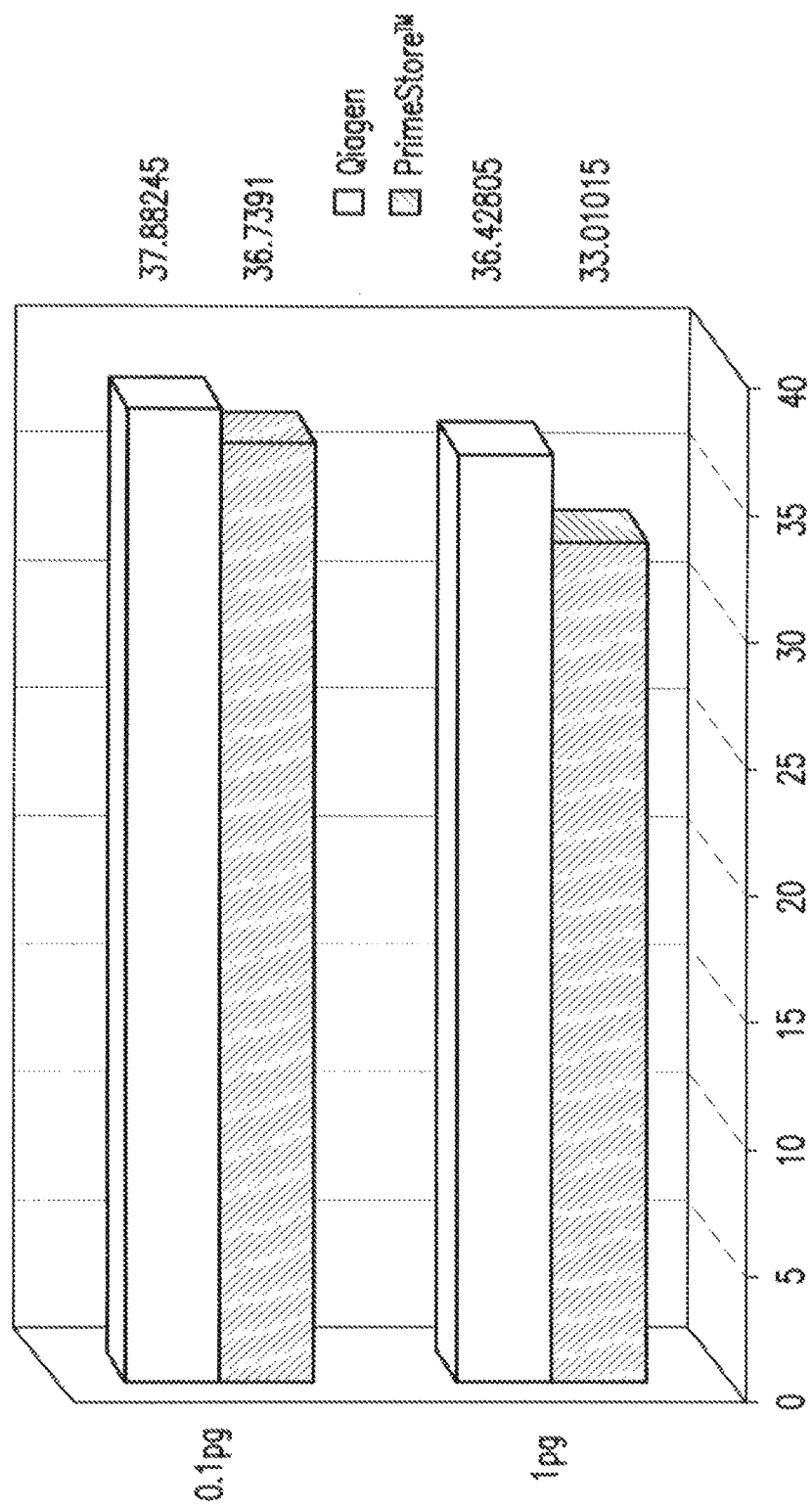

The data in FIG. 7B illustrate the ability of PSS to inactivate microbes. Shown is a study in which chicken cloacal specimens were collected in PSS (Ver. 1). PrimeStore™ Solution inactivated the microbial agents in ≤1 hr. Four original chicken cloacal samples were immersed in PSS or water and subsequently plated on blood agar plates. These results showed that the disclosed composition could quickly kill or inactive microorganisms in the sample.

The data in FIG. 7C illustrate the ability of PSS to inhibit RNA base hydrolysis for 30 days at room temperature. RNA was incubated at room temperature (22-26° C.) in PrimeStore™ (gel lane 1 and 3) and water (gel lane 2 and 4), and subsequently RT-PCR amplified (1500 base pairs) at Day 0 and Day 30. PSS preserved collected RNA, and prevented RNA/DNA degradation at room temperature up to 30 days (see also, e.g., Table 11).

Flu Inhibition Assay

The reagents for this assay include:

Trypsin medium containing: (a) 45 mL Sterile N/C EMEM; (b) 3 mL stock 7.5% Na Bicarbonate (2%); (c) 1.5 mL SPG (1%); (d) 75 µL trypsin (0.05%); (e) 1.5 mL fungizone (1%); and (f) 150 µL gentamicin.

Crystal violet containing: (a) 150 ml glutaric dialdehyde; (b) 2 gm crystal violet; and (c) 2850 mL deionized water Preparation of Serum Samples for Assay Thaw and vortex serum samples: For each sample, label the lid of a corresponding Spin-X™ tube. Combine 450 µL non-complete EMEM with 50 µL serum into a Spin-X™ tube. Warm tubes containing the sera and EMEM in a 56° C. water bath for 30 min. Centrifuge tubes at 8000 RPM for 2 min. at room temperature. Label and place samples into a −20° C. freezer until assayed.

Dilution Plates

Load 160 µL of each neat compound or serum sample into wells A1 through A12. Load the remaining wells with 120 µL trypsin medium. Using a multi-channel pipette, draw 40 µL of neat sample from row A and dilute into the corresponding wells in row B. Repeat dilution for each row, mixing well after each transfer. At row H, after mixing the transfer from row G, draw up 40 µL from each well and discard. Obtain virus stock ($10^6$) from −80° C. freezer and thaw. Dilute virus stock in trypsin media to a $10^3$ dilution. After serial dilutions are completed, transfer 120 µL of influenza virus ($10^4$ $TCID_{50}$ per ml) to all wells in the dilution plate. This results in a total of 240 µL in all wells. Incubate dilution plate(s) at room temperature for 1 hour.

MDCK Cell Plates

Sterilize and place glass reservoir, comb dispenser and tubing inside the fume hood. Inside the hood, connect the tubing to the reservoir and fill nozzle of the comb. Connect the aspirator tube to the vacuum nozzle on the comb. Place the reservoir on an elevated surface and turn on the aspirator. Put PBS into the reservoir (1 L or more may be needed depending on the number of plates). Wash the cell plates 3× with the PBS comb (aspirate the medium, then press the button for roughly 1 second to wash the wells, repeat twice). Using a multi-channel pipette, transfer 50 µL from each well in column 1 of the dilution plate to columns 1 through 4 of the cell plate. Transfer 50 µL from each well in column 2 of the dilution plate to columns 5 through 8 of the cell plate. Transfer 50 µL from each well in column 3 to columns 9 through 12 of the cell plate. Repeat transfer to additional cell plates for remaining samples. Incubate cell plates for 1 hour at 37° C. After incubation period, add 50 µL trypsin medium to all wells of the cell plates. Return plates to incubation chamber, and incubate for 4 days post-infection.

Staining

Add 100 µL, of crystal violet to all wells. Let sit for 1 hour. Rinse plates in cold running water and air dry.

TABLE 10

| 5 mM | 10 mM | 25 mM | 35 mM | 50 mM |
|---|---|---|---|---|
| TITRATION OF TCEP USING WHOLE INFLUENZA A VIRUS | | | | |
| 30.353 | 24.58 | 24.52 | 24.14 | 25.9582 |
| 30.2261 | 22.74 | 24.26 | 22.74 | 26.0337 |
| 30.28955 | 23.66 | 24.39 | 23.44 | 25.99595 |
| 0.089732 | 1.301076 | 0.183848 | 0.989949 | 0.053387 |
| Titration of TCEP Using H5 Avian ssRNA | | | | |
| 27.2 | 25.25 | 25.63 | 27.3 | 28.3039 |
| 26.73 | 24.89 | 25.36 | 27.62 | 26.6854 |
| 26.965 | 25.07 | 25.495 | 27.46 | 27.49465 |
| 0.33234 | 0.254558 | 0.190919 | 0.226274 | 1.144452 |

Time-Course Study of the Long-Term Stability of PrimeStore Compositions

The following data demonstrate the effectiveness of various PrimeStore compositions in preserving nucleic acid integrity over a thirty-day period with samples stored at room temperature. PrimeStore compositions have been compared to water alone, ethanol alone, commercial buffers such as VTM and AVL.

TABLE 11

30-DAY TIME-COURSE COMPARISON STUDY OF VARIOUS COMPOSITIONS

| VTM | Water | EtOH | AVL | PS-V1 (Year old) | PS-V1 (new lot) | PS-V2 | PS-V2.2 (w/EtOH) | |
|---|---|---|---|---|---|---|---|---|
| DAY 1 | | | | | | | | |
| VTM | Water | EtOH | AVL | PS-V1 (year old) | PS-V1 (new lot) | PS-V2 | PS-V2.2 (w/EtOH) | |
| 27.0225 | 26.1403 | 18.4463 | 24.2698 | 24.2607 | 23.9524 | 23.4426 | 20.2102 | |
| 24.42 | 25.6044 | 18.3206 | 24.4789 | 24.3716 | 23.9615 | 23.7387 | 20.063 | |
| 25.72125 | 25.87235 | 18.4463 | 24.37435 | 24.31615 | 23.95695 | 23.59065 | 20.1366 | AVG |
| 1.840245 | 0.378939 | 0.088883 | 0.147856 | 0.0784181 | 0.006435 | 0.209374 | 0.10408612 | STDEV |
| DAY 6 | | | | | | | | |
| 29.1988 | 29.3053 | 27.4058 | 37.9226 | 27.2379 | 27.165 | 24.53 | 22.4887 | |
| 28.6799 | 28.7916 | 27.0781 | 40 | 26.4857 | 26.7658 | 24.4418 | 22.4676 | |
| 28.93935 | 29.04845 | 27.24195 | 38.9613 | 26.8618 | 26.9654 | 24.4859 | 22.47815 | AVG |
| 0.366918 | 0.363241 | 0.231719 | 1.468944 | 0.5318857 | 0.282277 | 0.062367 | 0.01491995 | STDEV |
| DAY 12 | | | | | | | | |
| 27.997 | 28.151 | 26.9011 | 40 | 30.8352 | 31.0478 | 25.8926 | 22.2074 | |
| 28.0062 | 28.2211 | 26.2139 | 38.0439 | 30.4502 | 30.1935 | 25.3037 | 22.0025 | |
| 28.0016 | 28.18605 | 26.5575 | 39.02195 | 30.6427 | 30.62065 | 25.59815 | 22.10495 | AVG |
| 0.006505 | 0.049568 | 0.485924 | 1.383172 | 0.2722361 | 0.604081 | 0.416415 | 0.14488618 | STDEV |
| DAY 20 | | | | | | | | |
| 27.9851 | 28.7713 | 27.1105 | 40 | 30.1844 | 27.193 | 25.7407 | 20.8364 | |
| 28.4067 | 27.7929 | 27.0105 | 40 | 30.2465 | 27.2274 | 25.6213 | 20.2843 | |
| 28.1959 | 28.2821 | 27.0605 | 40 | 30.21545 | 27.2102 | 25.681 | 20.56035 | AVG |
| 0.298116 | 0.691833 | 0.070711 | 0 | 0.0439113 | 0.024324 | 0.084429 | 0.39039365 | STDEV |
| DAY 30 | | | | | | | | |
| 29.23 | 31.9168 | 33.012 | 40 | 29.1993 | 30.2386 | 23.0589 | 20.9348 | |
| 29.9067 | 31.3252 | 32.3001 | 40 | 28.827 | 29.6081 | 22.9662 | 20.4973 | |
| 29.56835 | 31.621 | 32.65605 | 40 | 29.01315 | 29.92335 | 23.01255 | 20.71605 | AVG |
| 0.478499 | 0.418324 | 0.503389 | 0 | 0.2632559 | 0.445831 | 0.065549 | 0.30935922 | STDEV |

PS-V1 (year old) = One-year old PSS (ver. 1).
PS-V1 (new lot) = Fresh PSS (ver. 2).
PS-V2 = Fresh PSS (ver 2) (without ethanol).
PS-V2.2 (w/EtOH) = Fresh PSS (ver. 2.2) (i.e., with ethanol).

Example 10

Storage Solutions Containing IPCs

As noted herein, in certain embodiments it is desirable to include a nucleic acid carrier molecule and/or an IPC sequence to aid in preparation, stabilization, and quantitation of the isolated polynucleotides.

In one embodiments, the inventors have employed a single-stranded RNA molecule that comprises the sequence of SEQ ID NO:2 which contains the following sequence:

(SEQ ID NO: 2)
5'-CCCUUAGCAGCACGUCAGUCAGGGAGCCAAUUUCAGAGCUCAGCGAG

ACAGUUUUAUAGGCAUGGCAUCAGCUACGCUCGCUCAGGCUAGUCAGGUC

CAAAGUUUCAGUU-3'

Figure 15A:
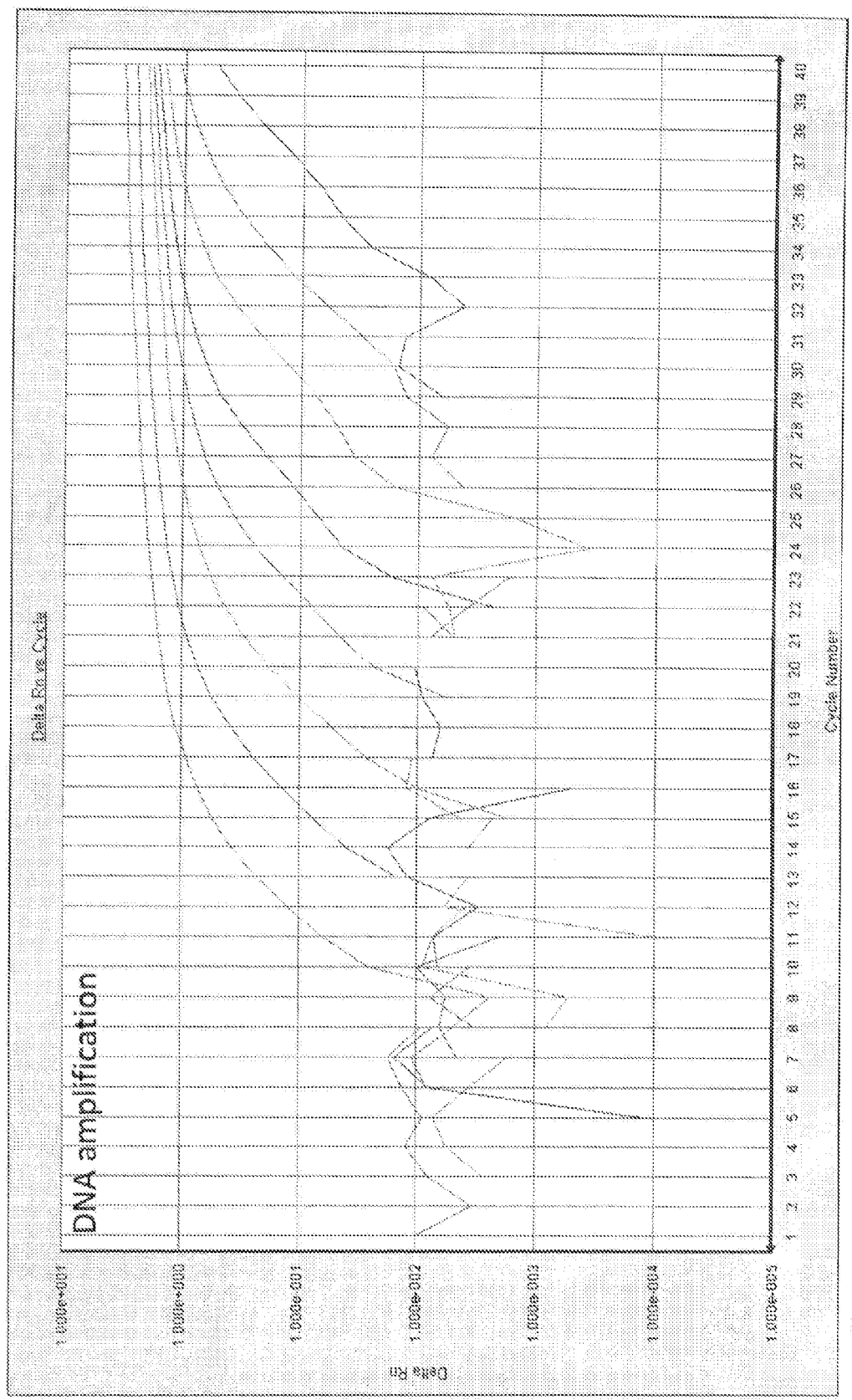
Figure 15B:
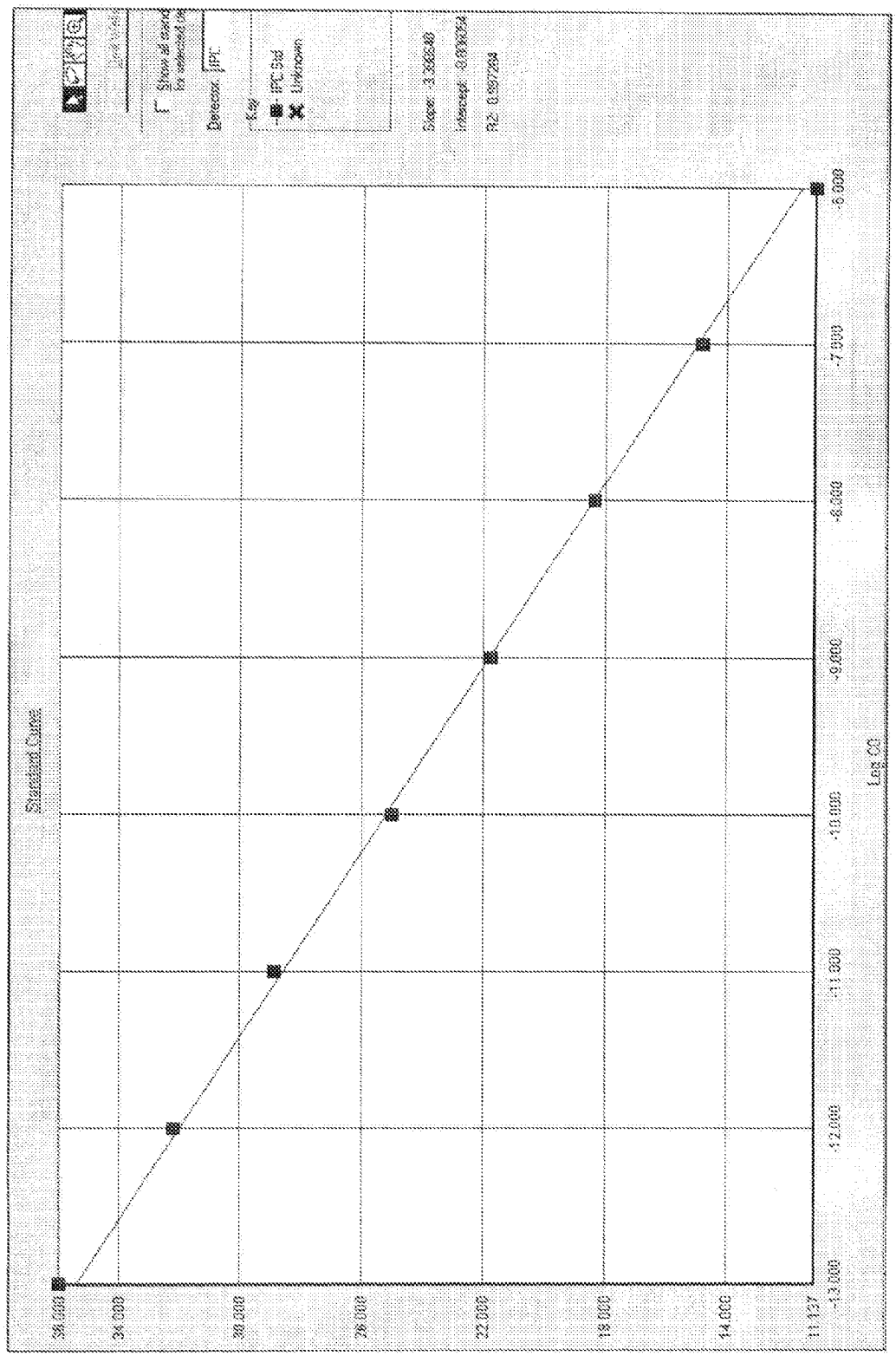
Figure 16A:
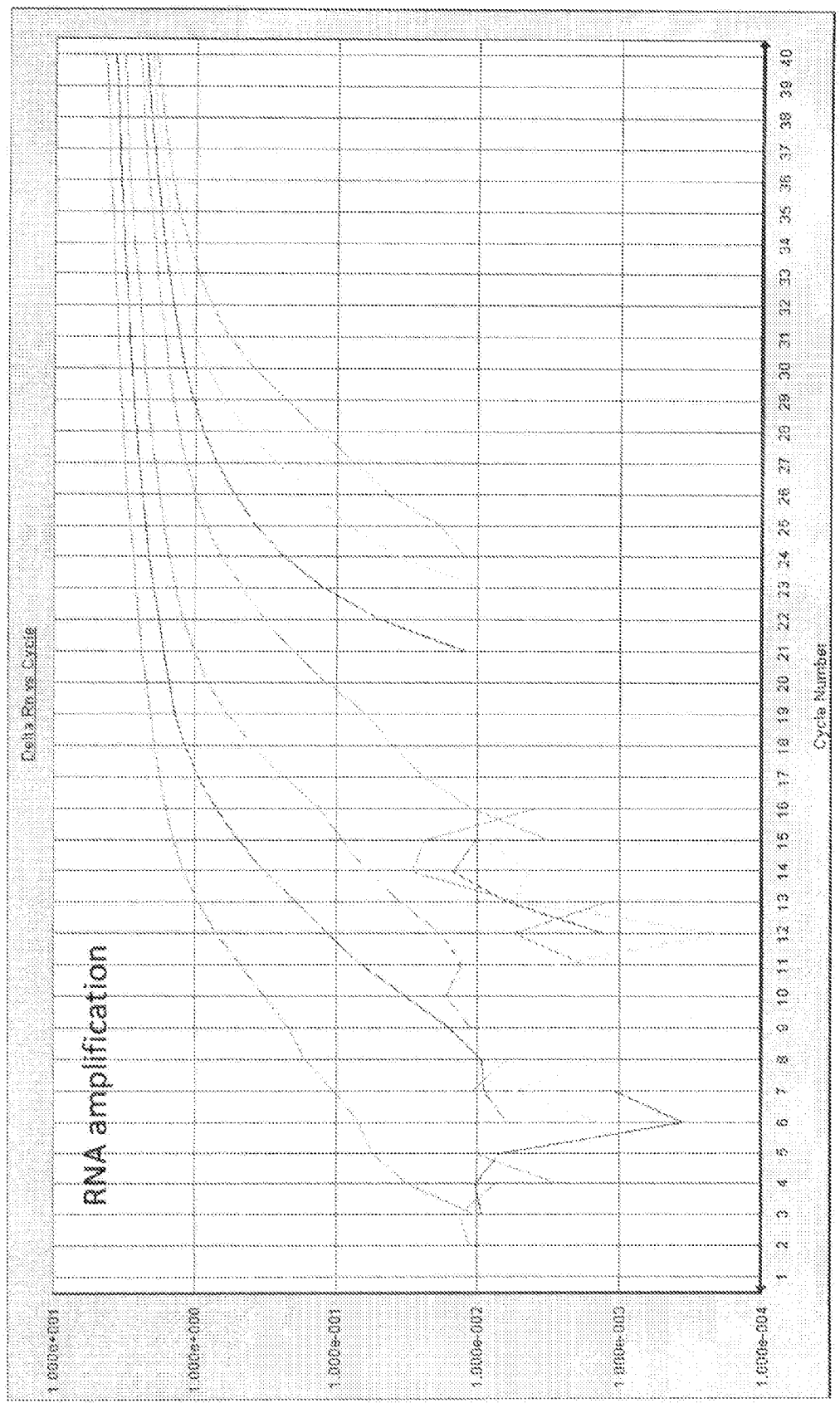
Figure 16B:
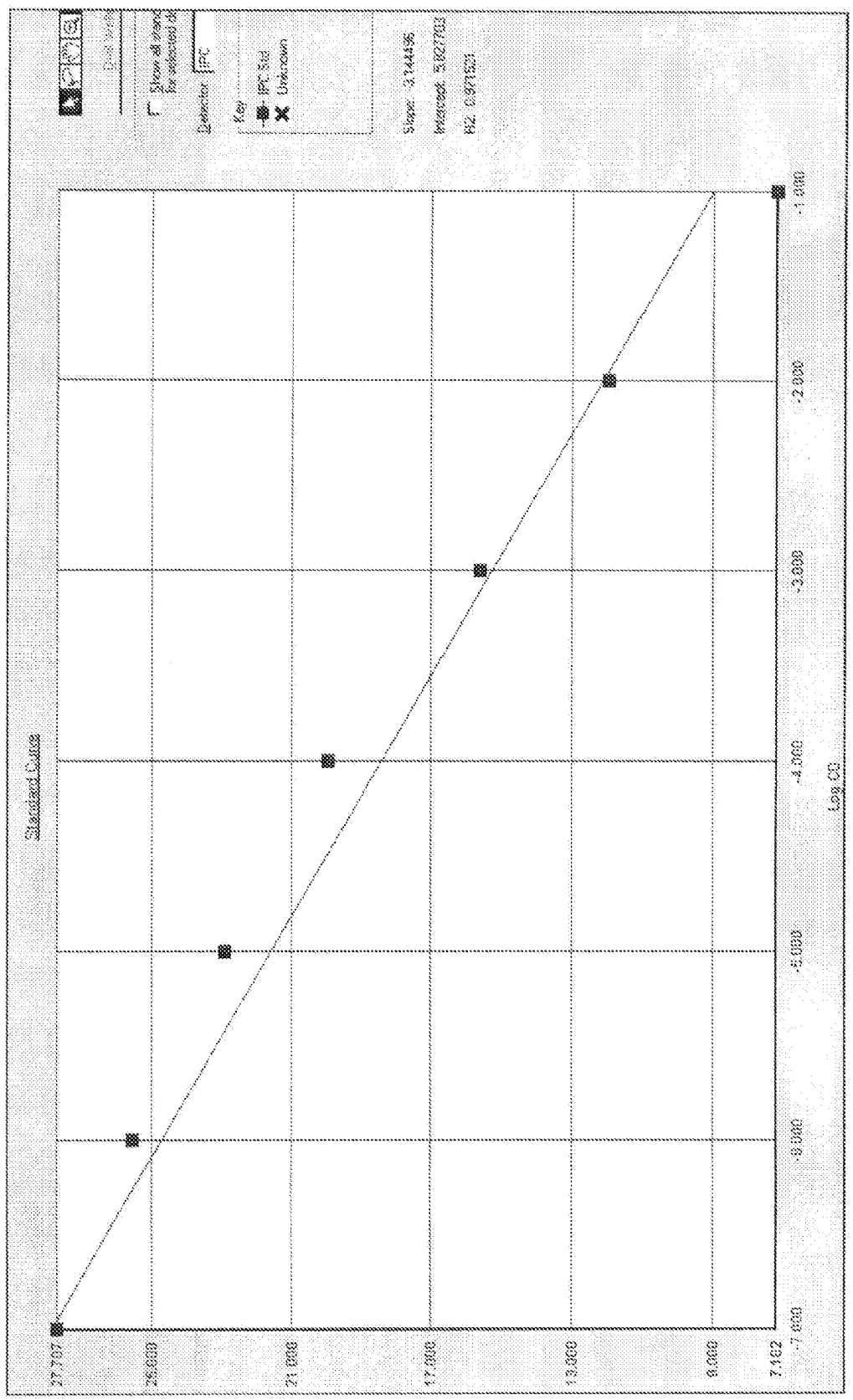

Data presented in FIG. 15A to FIG. 19 demonstrate the effectiveness of such IPC molecules in stabilizing the isolated population of polynucleotides, and acting as an assayable control sequence. In particular, FIG. 15A and FIG. 15B illustrate the real-time PCR amplification of a single stranded DNA using an assay specific for the detection of the IPC. Likewise, FIG. 16A and FIG. 16B illustrate a similar qRT-PCR amplification of the 130-nt ssRNA.

Figure 17:
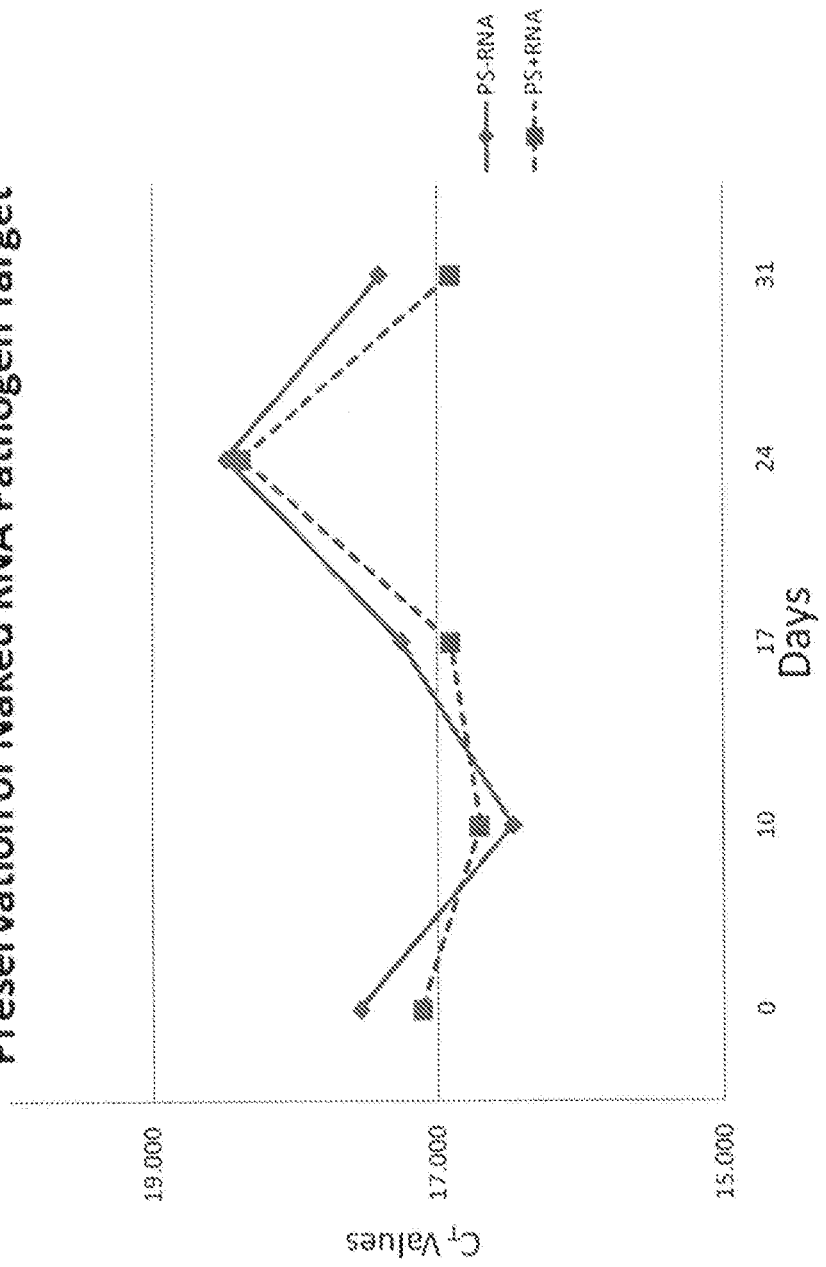

The data in FIG. 17 demonstrated that a PSS containing a synthetic RNA enhanced the preservation of a naked RNA pathogen target. In that study, a naked influenza A RNA template was added to a human nasal wash specimen, and then stored in PSS that either contained, or lacked the synthetic RNA. The results demonstrated that the presence of the synthetic RNA facilitated enhanced initial extraction of, and long-term preservation of the target sample.

Similarly, the data in FIG. 18 demonstrated that the stability of PrimeStore™ solution was enhanced by the addition of a synthetic carrier RNA. In this study, whole influenza A virus was preserved in PSS that either contained, or lacked, the synthetic RNA. The results demonstrated that the synthetic RNA enhanced initial extraction of, and long-term preservation of the target polynucleotide.

Finally, the data in FIG. 19 demonstrated the stability of synthetic RNA at room temperature and human body temperature (37° C.). In this study, the synthetic RNA carrier molecule was added to PSS, and stored for two weeks at either temperature. Stability of the RNA was measured by qRT-PCR. The synthetic carrier RNA was stable at both room temperature and at 37° C. for at least two weeks without significant decline in $C_T$ values.

It is important to note that IPCs useful in the practice of the present invention need not include one of the illustrative sequences described herein, nor do the IPCs even need be substantially homologous to any of the IPC sequences enclosed herein. To illustrate this point, the following sequences represent variants of SEQ ID NO:2 that are also functional as carrier RNA/IPC sequences, despite having sequence degeneracy:

(SEQ ID NO: 3)
5'-CUUAGCAGCACGUCAGUCAGGGAGCCAAUUCAGAGCUCAGCGAGACA

GUUUAUAGCAUGGCAUCAGCUACGCUCGCUCAGGCUAGUCAGGUCCAAAG

UUUCAGU-3'.

(SEQ ID NO: 4)
5'-UUAGCAGCACGUCAGUCAGGGAGCCAAUCAGAGCUCAGCGAGACAGU

UAUAGGCAUGGCAUCAGCUACGCUCGCUCAGGCUAGUCAGGUCCAAAGUU

UCA-3'.

(SEQ ID NO: 5)
5'-CCUAGCAGCACGUCAGUCAGGGAGCCAUUCAGAGCUCAGCGAGACAG

UUAUAGGCAUGGCAUCAGCUACGCUCGCUCAGGCUAGUCAGGUCCAAGUU

CAG-3'.

(SEQ ID NO: 6)
5'-AGCAGCACGUCAGUCAGGGAGCCAAUUCAGAGCUCAGCGAGACAGU

AUUUAGGCAUGCAUCAGCUACGCUCGCUCAGCCUAGUCACGUCCAAUGUA

UCAGU-3'.

(SEQ ID NO: 7)
5'-CUAGCAGCAGUCAGCAGGGAGCCAAUUUCAGAUCAGCGAGACAGUUU

AUAGCCGCAUGCCAUCAGCUACGCUCGCUUCAGCUAGUCAGUCAAGUUUU

CAGU-3'.

(SEQ ID NO: 8)
5'-UAGCAGCACGUCAGUCAGGGAGCCAAUUCAGAGCUCAGCGAGACAGU

UAGGCAUGCCAUCAACUACGCUCGCUCAGCCUAGUCACGUCCAAGUUCAG

AA-3'.

(SEQ ID NO: 9)
5'-CCUAGCAGCACGUCGUCAGGAGCCAAUUCAGAGCUCAGGAGACAGUU

UAUAGCAUGCAUCAGCUAGCUCGCUCAGCUAGUCAGUCAAGUUCAGUU-

3'.

(SEQ ID NO: 10)
5'-CUUACGCAGCACCGGUCAGUAUUCGCGGAGCCUAUUCAGAGCUCAGC

GAGACAGUUAUAGCAUGCAUCAGCUACCCUCGCUCAGGCUGUCAGGUCAG

UUCGAUU-3'.

(SEQ ID NO: 11)
5'-UAGCAGCACGUCAGUCAGAGCAUCAGAGCUCAGCGAGACAGAAUUAA

AGCCCAUGCAUCAGCUGCUGCUCAGCUAGUCAGUCCAAGUCCAGCU-3'.

(SEQ ID NO: 12)
5'-CCCUUAGCAGCACGUCAGUCAGGGAGCCAAUUUCAGAGCUCAGCAGU

UAUAGGCAUGGCAUCAGCUACGCUCGCAGUAGUCAGGUCCAAAGUUCAG

U-3'.

(SEQ ID NO: 13)
5'-CAGCACGUCAGUCAGAGCAUCAGAGCUCAGCGAGACAGUAUAGGCAU

GCAUCAGCACGCUCUCAGGCUAGUCAGCUCGAAAGUCAGAAU-3'.

Example 11

In Vitro Transcription of ssRNA IPC Sequences

As noted above, the IPCs of the invention may be directly chemically synthesized using conventional methods, or alternatively, prepared using recombinant DNA technology. The present example provides an example of the latter method, and exemplifies preparation of a dsDNA amplicon using PCR and in vitro RNA transcription assays. Using such recombinant techniques, an oligonucleotide is produced for adding to PSS as a stable, IPC that acts as a normalizer for qPCR of pathogen-specific sequences. The 141-nucleotide (nt) sequence is depicted 5' to 3' and shows: 1) T7 RNA transcription start (single underline) site, 2) internal forward and reverse primers (double underline), and 3) real-time internal probe sequence (bold). RNA is synthesis by PCR amplification using T7 forward (single underline) and IPC reverse (double underline) primers and transcribed in vitro using the Green T7 transcription start site. The resultant single stranded RNA polymer is 130-nt in length, and the IPC sequence is located (bound by the forward and reverse primers) within the RNA transcript.

(SEQ ID NO: 1)
5'-ATCGTAT<u>TAATACGACTCACTATAGGG</u>AATCGTC<u>GTGCAGTCAGTCCCTCGGTTA</u>AAG

TCTCGAGTCGCTCTGTCAAAATATCCGTACCGTAGTCGATGCGAGCGAGTCC<u>GATCAG

TCCAG GTTTCAAAAGTCAAA</u>TGACTA-3'.

The specifications for the illustrative DNA sequence employed in this study are as follows:

The total number of DNA nucleotides is 141, while the total number of RNA nucleotides is 130.

| | |
|---|---|
| % A = 26.95 | (38 nucleotides) |
| % G = 22.70 | (32 nucleotides) |
| % T = 26.24 | (37 nucleotides) |
| % C = 24.11 | (34 nucleotides) |

G+C content:

| | |
|---|---|
| % A + T = 53.19 | (75 nucleotides) |
| % C + G = 46.81 | (66 nucleotides) |

Base Count: 38 (A), 34 (C), 32 (G), and 37 (T).

The primers and probe sequences for the illustrative IPC assay is located within the synthetic DNA/RNA polymer (shown below). The resulting amplification is 100-bp in length. The primers and probe assay were designed to operate using a two-step thermocycling protocol consisting of one cycle at 50° C. for 20 min and 95° C. for 5 min for reverse transcription and hot start activation, respectively. This is then followed by 40 cycles of 95° C. for 15 sec and 60° C. for 30 sec.

```
                                                 (SEQ ID NO: 24)
Forward primer: 5'-GTGCAGTCAGTCCCTCGGTTA-3'.

(SEQ ID NO: 25)
Reverse primer: 5'-TTGACTTTGAAACCTGGACTGATC-3'.

(SEQ ID NO: 26)
Probe: 5'-(FAM)-AAATATCCGTACCGTAGTCG-(MGB)-3'.
```

TABLE 12

PANEL OF NUCLEIC ACIDS USED TO EVALUATE CROSS-REACTIVITY OF IPC QPCR ASSAY

| Viruses | Bacteria | Other |
|---|---|---|
| Influenza A (H3) | S. pyogenes | Total human DNA |
| Influenza A (H1) | S. aureus | Total human RNA |
| Influenza B | B. pertussis | |
| Parainfluenza 1, 2, 3, 4 | S. pneumoniae | |
| CMV (HHV5) | N. gonorrhoeae | |
| Herpes (HHV1) | H. influenzae B | |
| Adenovirus 4, 7 | E. coli | |
| Echovirus | | |
| RSV | | |
| Enterovirus | | |

As noted above, it is desirable to formulate an IPC sequence that is both non-genomic, and that does not significantly hybridize to a mammalian genome, or to the genome of pathogenic species of interest.

To that end, the IPC produced in vitro by PCR amplification from SEQ ID NO:1, was screened against a panel of total genomic sequences from a number of viral and bacterial species, as well as total human RNA and DNA. Table 12 lists the species screened; none cross-hybridized to the IPC sequence indicating its desirability as a "nonsense" control sequence that lacked significant homology to any of the tested organisms.

As noted above, the IPCs of the present invention need not be prepared from the precise illustrative DNA amplicon disclosed herein as SEQ ID NO:1. Additional examples of DNA sequences useful in the in vitro preparation of suitable carrier RNA molecules include, without limitation, one or more of the following sequences. In each instance, the polymerase transcription site (here, the T7 transcription site) is shown in single underline, while the sequences of exemplary forward and reverse PCR primer binding domains are shown in double underline. Exemplary sequence domains to which suitable labeled molecular probes are bound are shown in bold.

```
                                                 (SEQ ID NO: 14)
5'-X_n TAT TAATACGACTCACTATAGGGX_n GTGCAGTCAGTCCCTCGGTT

AAAGTCTCGAGTCGCTCTGTCA AAATATCCGTACCGTAGTCG ATGCGAGC

GAGTCC GATCAGTCCAGGTTTCAAAGTCAA X_n -3',
``` wherein X is any nucleotide and n is any integer from 0 to about 500.

```
                                                 (SEQ ID NO: 15)
5'-ATCGTAT TAATACGACTCACTATAGGG AATCGTC GTGCAGTCAGTCCCTCGGTTA AA

GTCTCGAGTCGCTCTGTCA AAATATCCGTACCGTAGTCG ATGCGAGCGAGTCC GATC

AGTCCAGGTTTCAAAGTCAA ATGACTA-3'.

(SEQ ID NO: 16)
5'-ATCGTAT TAATACGACTCACTATAGGG AATCGTC GTGCAGTCAGTCCCTCGGTTA AA

GTCTCGAGTCGCT CTGTCAAAATATCCGTACCGTAGTCGATG CGAGCGAGTCCGA TC

AGTCCAGGTTTCAAAGTCAA ATGACTA-3'.

(SEQ ID NO: 17)
5'-ATCGTAT TAATACGACTCACTATAGGG AATCGTCGTG CAGTCAGTCCCTCGGTTA AA

GTCTCGAGTCGCTCTGTCA AAATATCCGTACCGTAGTCG ATGCGAGCGAG TCCGATC

AGTCCAGGTTTCAAAGTC AAATGACTA-3'.

(SEQ ID NO: 18)
5'-ATAT TAATACGACTCACTATAGGGA GTGCAGTCAGTCCCTCGGTTA AAGTCTCGAGT

CGCTCTGTCA AAATATCCGTACCGTAGTCG ATGCGAGCGAGTCC GATCAGTCCAGGT

TTCAAAGTCAA AT-3'.

(SEQ ID NO: 19)
5'-ATAT TAATACGACTCACTATAGGGA GTGCAGTCAGTCCCTCGGTTA AAGTCTCGAGT

CGCTCTGTCA AAATATCCGTACCGTAGTCG ATGCGAGCGAGTCC GATCAGTCCAGGT

TTCAAAGTCAA AT-3'.

(SEQ ID NO: 20)
5'-ATAT TAATACGACTCACTATAGGGA GTGCAGTCAGTCCCTCGGTTA AAGTCTCGAGT

CGCTCTGTCA AAATATCCGTACCGTAGTCG ATGCGAGCGAGTCCGA TCAGTCCAGGT

TTCAAAGTCAA AT-3'.
```

-continued (SEQ ID NO: 21)
5'-TAT<u>TAATACGACTCACTATAGGG</u><u>GTGCAGTCAGTCCCTCGGTTA</u>AAGTCTCGAGTCG
CTCTGTCAAAATATCCGTACCGTAGTCGATGCGAGCGAGTCC<u>GATCAGTCCAGGTTT</u>
<u>CAAAGTCAA</u>-3'.

(SEQ ID NO: 22)
5'-TAT<u>TAATACGACTCACTATAGGG</u>GTG<u>CAGTCAGTCCCTCGGTTAAAG</u>TCTCGAGTCG
CTCTGTCAAAATATCCGTACCGTAGTCGATGCGAGCGAGT<u>CCGATCAGTCCAGGTTT</u>
<u>CAAAGTCAA</u>-3'.

(SEQ ID NO: 23)
5'-TAT<u>TAATACGACTCACTATAGGG</u>GTGCAGTCAGTCCCTCGGTTAAAGTCTCGAGTCG
CTCTGTCAAAATATCCGTACCGTAGTCGATGCGAGCGA<u>GTCCGATCAGTCCAGGTTT</u>
<u>CAAAGTCA</u>A-3'.

All of the compositions and methods disclosed and claimed herein can be made and executed without undue experimentation in light of the present disclosure. While the compositions and methods of this invention have been described in terms of exemplary embodiments, it will be apparent to those of ordinary skill in the art that variations may be applied to the composition, methods and in the steps or in the sequence of steps of the method described herein without departing from the concept, spirit and scope of the invention. More specifically, it will be apparent that certain agents that are both chemically- and physiologically-related may be substituted for the agents described herein while the same or similar results would be achieved. All such similar substitutes and modifications apparent to those of ordinary skill in the art are deemed to be within the spirit, scope and concept of the invention as defined by the appended claims. Accordingly, the exclusive rights sought to be patented are as described in the claims below.

What is claimed is:

1. A one-step method of maintaining the integrity of a biological sample for nucleic acid testing in solution, comprising providing an aqueous mixture at a pH of about 6 to 7 that contains:
    a control nucleic acid sequence,
    one or more chaotropes;
    one or more detergents;
    one or more reducing agents;
    one or more chelators; and
    one or more buffers,
    collectively and in an amount sufficient to denature proteins, inactivate nucleases, kill pathogens, and release nucleic acid from an organism or cell contained within the biological sample when contacted with the biological sample in solution, wherein:
    upon contact with the biological sample in solution, the released nucleic acid and the control nucleic sequence acid are each detectable in solution by nucleic acid testing for at least 7 days when stored at a temperature of greater than 4° C. and the control nucleic acid sequence is distinguishable from the released nucleic acid; and
    the control nucleic acid sequence and the released nucleic acid in solution are detectable by a single nucleic acid testing.

2. The method of claim 1, wherein the control nucleic acid sequence does not hybridize to released nucleic acid under stringent hybridization conditions.

3. The method of claim 2, wherein the control nucleic acid sequence does not ordinarily occur within a mammalian genome, or a genome of a bacterium, fungus, protozoan, or virus that is pathogenic to a mammal.

4. The method of claim 3, wherein the control nucleic acid sequence is synthetic and from about 40 to about 900 nucleotides in length.

5. The method of claim 4, wherein the control nucleic acid is present in the mixture at a concentration of about 1 pg to 1 μg/ml of mixture.

6. The method of claim 5, wherein the control nucleic acid is a calibration control for the nucleic acid testing.

7. The method of claim 1, wherein the nucleic acid testing is PCR analysis.

8. The method of claim 7, wherein the control nucleic acid sequence and the released nucleic acid are detectable by a single PCR analysis.

9. The method of claim 1, wherein the pH of the mixture is from about 6.2 to 6.9.

10. The method of claim 1, wherein the released nucleic acid and the control nucleic sequence acid are each detectable by nucleic acid testing for at least 14 days.

11. The method of claim 10, wherein the released nucleic acid and the control nucleic acid sequence are each detectable by nucleic acid testing for at least 21 days.

12. The method of claim 1, wherein the released nucleic acid and the control nucleic sequence acid are each detectable by nucleic acid testing for at least 7 days when the temperature is about 10° C. or greater.

13. The method of claim 12, wherein the released nucleic acid and the control nucleic sequence acid are each detectable by nucleic acid testing for at least 7 days when the temperature is about 14° C. or greater.

14. The method of claim 12, wherein the released nucleic acid and the control nucleic sequence acid are each detectable by nucleic acid testing for at least 21 days when the temperature is about 10° C. or greater.

15. The method of claim 1, wherein the one or more chaotropes are present in an amount from about 0.5 M to about 6 M; the one or more detergents are present in an amount from about 0.1% to about 1% (wt./vol.); the one or more reducing agents are present in an amount from about 0.5 mM to about 0.3 M; the one or more chelators are present in an amount from about 0.01 mM to about 1 mM; and the one or more buffers are present in an amount from about 1 mM to about 1 M.

16. The method of claim 15, wherein:
the one or more chaotropes comprise guanidine thiocyanate, guanidine isocyanate, guanidine hydrochloride, or any combination thereof;
the one or more detergents comprise sodium dodecyl sulfate, lithium dodecyl sulfate, sodium taurodeoxycholate, sodium taurocholate, sodium glycocholate, sodium deoxycholate, sodium cholate, sodium alkylbenzene sulfonate, N-lauroyl sarcosine, or any combination thereof;
the one or more reducing agents comprise 2-mercaptoethanol, tris(2-carboxyethyl) phosphine, dithiothreitol, dimethylsulfoxide, or any combination thereof; the one or more chelators comprise ethylene glycol tetra acetic acid, hydroxyethylethylenediaminetriacetic acid, diethylene triamine penta acetic acid, N,N-bis(carboxymethyl)glycine, ethylenediaminetetraacetic, citrate anhydrous, sodium citrate, calcium citrate, ammonium citrate, ammonium bicitrate, citric acid, diammonium citrate, ferric ammonium citrate, lithium citrate, or any combination thereof; and
the one or more buffers comprise tris(hydroxymethyl) aminomethane, citrate, 2-(N-morpholino)ethanesulfonic acid, N,N-Bis(2-hydroxyethyl)-2-aminoethanesulfonic acid, 1,3-bis(tris(hydroxymethyl)methyl amino)propane, 4-(2-hydroxyethyl)-1-piperazine ethanesulfonic acid, 3-(N-morpholino) propanesulfonic acid, bicarbonate, phosphate, or any combination thereof.

17. The method of claim 1, wherein the mixture further comprises:
one or more surfactants or defoaming agents at about 0.0001% to about 0.3% (wt./vol.); and;
one or more short-chain alkanols at about 1% to 25% (vol./vol.).

18. The method of claim 17, wherein the one or more surfactants or defoaming agents is selected from the group consisting of a silicone polymer, a polysorbate, and any combination thereof; and the one or more short-chain alkanols is selected from the group consisting of methanol, ethanol, propanol, butanol, pentanol, hexanol, and any combination thereof.

19. The method of claim 18, wherein the mixture comprises:
about 4 M guanidine thiocyanate; about 30 mM sodium citrate; about 0.25% (wt./vol.) sodium dodecyl sulfate; about 0.25% (wt./vol.) N-lauroyl sarcosine, sodium salt; about 0.1 M 2-mercaptoethanol; and about 0.1% silicone polymer (wt./vol.); or
about 3 M guanidine thiocyanate; about 1 mM TCEP; about 10 mM sodium citrate; about 0.5% N-lauroyl sarcosine; about 0.0002% silicone polymer; about 100 mM 2-amino-2-hydroxymethyl-propane-1,3-diol (TRIS); and about 0.1 mM EDTA; or
about 1 M to about 4 M guanidine thiocyanate; about 0.5 mM to 10 mM TCEP; about 1 mM to 100 mM sodium citrate; about 0.1% to about 1% SDS or NLS; about 0.001% to about 0.0001% of a silicone polymer, about 10 mM to about 500 mM TRIS, about 0.1 mM to about 1 mM APCA, EDTA, EGTA, HEDTA, DTPA, NTA, or citrate; and about 10% to about 25% ethanol (vol./vol.); or
about 3 M guanidine thiocyanate; 1 mM TCEP; about 10 mM sodium citrate; about 0.5% N-lauroyl sarcosine, sodium salt; about 0.0002% of a silicone polymer; about 100 mM TRIS; about 0.1 mM EDTA; and about 10% to about 25% ethanol (vol./vol.).

20. The method of claim 1, wherein 5% or less of the released nucleic acid is degraded after the at least 7 days.

21. The method of claim 1, further comprising contacting the biological sample with the mixture.

22. The method of claim 21, further comprising performing nucleic acid testing of the released nucleic acid and the control nucleic acid sequence.

23. The method of claim 22, wherein the control nucleic acid sequence comprises:
a first sequence domain that specifically binds to a labeled probe of about 12 to about 35 nucleotides in length that is specific for detection of the control nucleic acid sequence;
a second sequence domain that specifically binds to a forward PCR amplification primer of about 15 to about 35 nucleotides in length; and
a third sequence domain that specifically binds to a reverse PCR amplification primer of about 15 to about 35 nucleotides in length, wherein the second and third sequence domains are operably positioned to facilitate a PCR-directed amplification of at least a first portion of the control nucleic acid sequence from the forward and reverse primers under conditions effective to amplify the at least a first portion.

24. A one-step method of maintaining the integrity of a biological sample in solution for nucleic acid testing, comprising:
providing an aqueous mixture at a pH of about 6 to 7 that contains:
a control nucleic acid sequence,
one or more chaotropes;
one or more detergents;
one or more reducing agents;
one or more chelators; and
one or more buffers,
contacting the biological sample in solution to an amount of the mixture that is sufficient to denature proteins, inactivate nucleases, kill pathogens, and release nucleic acid from an organism or cell contained within the biological sample,
wherein the released nucleic acid and the control nucleic sequence acid are each detectable in solution by nucleic acid testing for at least 7 days when stored at a temperature of greater than 10° C. and the control nucleic acid sequence is distinguishable from the released nucleic acid, and
wherein the control nucleic acid sequence and the released nucleic acid are detectable by a single nucleic acid testing.

25. The method of claim 24, wherein the mixture further comprises:
one or more surfactants or defoaming agents at about 0.0001% to about 0.3% (wt./vol.); and;
one or more short-chain alkanols at about 1% to 25% (vol./vol.).

26. The method of claim 24, wherein the released nucleic acid comprises a sequence identifiable as derived from influenza virus.

27. The method of claim 24, wherein the released nucleic acid comprises a sequence identifiable as derived from tuberculosis bacteria.

28. The method of claim 24, wherein the contacting is performed in one vessel and, after contact, the biological sample is non-infectious for transport.

29. The method of claim 24, wherein, after the contacting, the biological sample does not require refrigeration before the nucleic acid testing.

30. The method of claim 24, further comprising:
performing the nucleic acid testing on the released nucleic acid and determining the presence or absence of a pathogen in the biological sample.

31. The method of claim 30, wherein the nucleic acid testing is a single PCR analysis.

32. The method of claim 30, wherein the pathogen is virus or bacteria.

33. The method of claim 32, wherein the virus or bacteria is influenza virus or tuberculosis bacteria.

34. A one-step method of maintaining the integrity of a biological sample in solution for nucleic acid testing to determine the presence or absence of a pathogen, comprising:
providing an aqueous mixture at a pH of about 6 to 7 that contains:
a control nucleic acid sequence, one or more chaotropes;
one or more detergents;
one or more reducing agents;
one or more chelators; and
one or more buffers,
contacting in one step the biological sample in solution to an amount of the mixture that is sufficient to denature proteins, inactivate nucleases, kill pathogens, and release nucleic acid from an organism or cell contained within the biological sample, wherein the released nucleic acid and the control nucleic sequence acid are each detectable in solution by nucleic acid testing for at least 2 days when stored at a temperature of greater than 10° C. and the control nucleic acid sequence is distinguishable from the released nucleic acid; and
performing nucleic acid testing on the released nucleic acid and the control nucleic acid sequence, wherein the nucleic acid testing is a PCR analysis;
determining the amount of released nucleic acid present in the sample from the amount of control nucleic acid sequence present in the mixture; and
determining the presence or absence of the pathogen in the biological sample.

35. The method of claim 34, wherein the mixture further comprises:
one or more surfactants or defoaming agents at about 0.0001% to about 0.3% (wt./vol.); and;
one or more short-chain alkanols at about 1% to 25% (vol./vol.).

36. The method of claim 34, further comprising transporting the contacted biological sample before performing nucleic acid testing wherein the contacted biological sample is non-infectious for transportation.

37. The method of claim 34, wherein the released nucleic acid is present at 0.1 pg and detectable at a $C_T$ value of about 36.

38. The method of claim 34, wherein the released nucleic acid is present at 1 pg and detectable at a $C_T$ value of about 33.

39. The method of claim 34, wherein the released nucleic acid is detectable at a $C_T$ value that is reduced by at least 5% as compared to the $C_T$ value obtained in the absence of the mixture.

40. The method of claim 39, wherein the released nucleic acid is detectable at a $C_T$ value that is reduced by at least 10% as compared to the $C_T$ value obtained in the absence of the mixture.

* * * * *